United States Patent
Owens et al.

(10) Patent No.: US 9,770,349 B2
(45) Date of Patent: Sep. 26, 2017

(54) NANOPOROUS STENTS WITH ENHANCED CELLULAR ADHESION AND REDUCED NEOINTIMAL FORMATION

(75) Inventors: Gary Owens, Earlysville, VA (US); Whye-Kei Lye, Charlottesville, VA (US); Michael Reed, Charlottesville, VA (US); Joshua Spradlin, Charlottesville, VA (US); Brian Wamhoff, Charlottesville, VA (US); Matthew Hudson, Charlottesville, VA (US); Kareen Looi, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 2672 days.

(21) Appl. No.: 11/753,134

(22) Filed: May 24, 2007

(65) Prior Publication Data

US 2008/0086198 A1    Apr. 10, 2008

Related U.S. Application Data

(63) Continuation-in-part of application No. 11/200,655, filed on Aug. 10, 2005, now abandoned, which is a
(Continued)

(51) Int. Cl.
*A61F 2/82*    (2013.01)
*A61F 2/91*    (2013.01)

(52) U.S. Cl.
CPC .......... *A61F 2/91* (2013.01); *A61F 2/82* (2013.01); *A61F 2240/001* (2013.01); *A61F 2250/0058* (2013.01)

(58) Field of Classification Search
CPC .............. A61F 2/82; A61F 2240/001; A61F 2250/0058
(Continued)

(56) References Cited

U.S. PATENT DOCUMENTS

| 2,021,520 A | 11/1935 | Reichmann |
| 3,190,749 A | 6/1965 | Fleming |

(Continued)

FOREIGN PATENT DOCUMENTS

| EP | 0392738 | 10/1990 |
| EP | 0706376 | 4/1996 |

(Continued)

OTHER PUBLICATIONS

Forty et al. "A Micromorphological Study of the Dissolution of Silver-Gold Alloys in Nitric Acid" Philosophical Magazine A, 1980, vol. 42, No. 3, 295-318.
(Continued)

*Primary Examiner* — Paul Prebilic

(57) ABSTRACT

The present invention relates generally to medical devices containing nanoporous surfaces and methods for making same. More specifically, the invention relates to implantable vascular stents or other biomedical devices having at least one dealloyed nanoporous layer that promotes improved cellular adhesion properties that promote healing and long term biocompatibility. In the case of stents, the nanoporous layer promotes re-endothelialization at sites of stent implantation vasculature, improves overall healing, and reduces inflammation and intimal disease progression. The nanoporous layer may be optionally loaded with one or more therapeutic agent to further improve the function of the implanted stent and further augment clinical efficacy.

11 Claims, 22 Drawing Sheets

Related U.S. Application Data continuation-in-part of application No. 10/918,853, filed on Aug. 13, 2004, now abandoned, which is a continuation-in-part of application No. 10/713,244, filed on Nov. 13, 2003, now Pat. No. 7,294,409.

(60) Provisional application No. 60/809,465, filed on May 31, 2006, provisional application No. 60/602,542, filed on Aug. 18, 2004, provisional application No. 60/613,165, filed on Sep. 24, 2004, provisional application No. 60/664,376, filed on Mar. 23, 2005, provisional application No. 60/699,302, filed on Jul. 14, 2005, provisional application No. 60/426,106, filed on Nov. 13, 2002.

(58) Field of Classification Search
USPC .................................. 623/1.15, 1.42–1.48
See application file for complete search history.

(56) References Cited

U.S. PATENT DOCUMENTS

| | | | |
|---|---|---|---|
| 3,338,805 A | 8/1967 | Pochily et al. | |
| 3,923,969 A | 12/1975 | Baukal et al. | |
| 3,948,254 A | 4/1976 | Zaffaroni | |
| 3,993,072 A | 11/1976 | Zaffaroni | |
| 4,218,255 A | 8/1980 | Bajpai et al. | |
| 4,459,252 A | 7/1984 | MacGregor | |
| 4,977,038 A | 12/1990 | Sieradszki et al. | |
| 5,246,689 A | 9/1993 | Beck et al. | |
| 5,340,614 A | 8/1994 | Perman et al. | |
| 5,508,060 A | 4/1996 | Perman et al. | |
| 5,569,198 A | 10/1996 | Racchini | |
| 5,769,884 A | 6/1998 | Solovay | |
| 5,843,172 A | 12/1998 | Yan | |
| 5,843,289 A | 12/1998 | Lee et al. | |
| 5,947,893 A | 9/1999 | Agrawal et al. | |
| 5,972,027 A | 10/1999 | Johnson | |
| 5,980,551 A | 11/1999 | Summers et al. | |
| 5,985,307 A | 11/1999 | Hanson et al. | |
| 6,019,784 A | 2/2000 | Hines | |
| 6,027,863 A | 2/2000 | Donadio, III | |
| 6,093,498 A | 7/2000 | Baldi | |
| 6,096,070 A * | 8/2000 | Ragheb et al. | 623/1.39 |
| 6,107,004 A | 8/2000 | Donadio, III | |
| 6,183,255 B1 | 2/2001 | Oshida | |
| 6,203,732 B1 | 3/2001 | Clubb et al. | |
| 6,240,616 B1 | 6/2001 | Yan | |
| 6,273,913 B1 | 8/2001 | Wright et al. | |
| 6,379,381 B1 | 4/2002 | Hossainy et al. | |
| 6,506,437 B1 | 1/2003 | Harish et al. | |
| 6,527,938 B2 | 3/2003 | Bales et al. | |
| 6,709,379 B1 | 3/2004 | Brandau et al. | |
| 6,712,845 B2 | 3/2004 | Hossainy | |
| 6,758,859 B1 | 7/2004 | Dang et al. | |
| 6,797,311 B2 | 9/2004 | Loomis et al. | |
| 6,805,898 B1 | 10/2004 | Wu et al. | |
| 6,939,376 B2 | 9/2005 | Shulze et al. | |
| 7,244,830 B2 * | 7/2007 | Chaikof et al. | 536/18.7 |
| 7,682,387 B2 * | 3/2010 | Shulze et al. | 623/1.42 |
| 2002/0032414 A1 | 3/2002 | Ragheb et al. | |
| 2002/0052650 A1 | 5/2002 | Rourke et al. | |
| 2002/0090725 A1 * | 7/2002 | Simpson et al. | 435/402 |
| 2002/0133224 A1 | 9/2002 | Bajgar et al. | |
| 2002/0187260 A1 * | 12/2002 | Sheppard et al. | 427/248.1 |
| 2002/0198601 A1 | 12/2002 | Bales et al. | |
| 2003/0023303 A1 * | 1/2003 | Palmaz et al. | 623/2.18 |
| 2003/0033007 A1 * | 2/2003 | Sirhan et al. | 623/1.42 |
| 2003/0060873 A1 | 3/2003 | Gertner et al. | |
| 2003/0083646 A1 * | 5/2003 | Sirhan et al. | 604/891.1 |
| 2003/0170287 A1 * | 9/2003 | Prescott | 424/423 |
| 2003/0186522 A1 | 10/2003 | Duan et al. | |
| 2004/0000046 A1 | 1/2004 | Stinson | |
| 2004/0002755 A1 * | 1/2004 | Fischell et al. | 623/1.42 |
| 2004/0005723 A1 | 1/2004 | Empedocles et al. | |
| 2004/0026684 A1 | 2/2004 | Empedocles | |
| 2004/0039438 A1 | 2/2004 | Alt | |
| 2004/0073298 A1 | 4/2004 | Hossainy | |
| 2004/0095658 A1 | 5/2004 | Buretea et al. | |
| 2004/0118448 A1 | 6/2004 | Scher et al. | |
| 2004/0136866 A1 | 7/2004 | Pontis et al. | |
| 2004/0146560 A1 | 7/2004 | Whiteford et al. | |
| 2004/0148015 A1 | 7/2004 | Lye et al. | |
| 2005/0070989 A1 | 3/2005 | Lye et al. | |
| 2005/0079200 A1 | 4/2005 | Rathenow et al. | |
| 2005/0106212 A1 | 5/2005 | Gertner et al. | |
| 2005/0209688 A1 | 9/2005 | Falotico et al. | |
| 2006/0134218 A1 * | 6/2006 | Abul-Khoudoud et al. | 424/486 |
| 2010/0286763 A1 * | 11/2010 | Alt | 623/1.42 |

FOREIGN PATENT DOCUMENTS

| | | |
|---|---|---|
| EP | 1319416 | 6/2003 |
| WO | WO00/01322 | 1/2000 |
| WO | WO00/25841 | 5/2000 |
| WO | WO00/48660 | 8/2000 |
| WO | WO03/045582 | 6/2003 |

OTHER PUBLICATIONS

Martinez, et al. "Kinetics of the Dissolution of Pure Silver and Silver-Gold Alloys in Nitric Acid Solution" Metallurigical Transactions B, vol. 24B, pp. 827-837, Oct. 1993.

Heublein et al., "Biocorrosion of Magnesium Alloys: A New Principle in Cardiovascular Implant Technology," 1989, Heart 651 (2003).

DiMario et al., "Drug-Eluting Bioabsorbable Magnesium Stent" 17 J. Interven. Cardiol. 391 (2004).

Edelman et al., "Gold Coated NIR Stents in Porcine Coronary Arteries" Circulation 2001 103:429-434.

Park, JY at el., "Platelet Interactions With Titanium: Modulation of Platelet Activity by Surface Topography" Biomaterials 22 (2001) 2671-2682.

Simamora et al., "Solubilization of Rapamycin" Int. J. Pharmaceutics 213: 25-29, 2001.

Li et al., "Ductile-Brittle Transition in Random Porous Au," Physical Review Letters, vol. 68, No. 8, pp. 1168-1171, Feb. 24, 1992.

Ateya, et al., "The Effects of Potentional and Kinetic Parameters on the Formation of Passivating Nobel Metal Rich Surface Layers During the Selective Dissolution of Binary Alloys" Corrosion Science, vol. 38, No. 8, pp. 1245-1267. 1996.

Eriebacher et al., "Evolution of Nanoporosity in Dealloying" Nature, vol. 410, pp. 450-452, Mar. 22, 2001.

Simmonds et al., "The Observation of a Threshold in the De-Alloying of Sputter-Deposited $Pt_xAl_{1-x}$ Alloy Thing Films," Corrosion Science, vol. 40, No. 1, pp. CY 43-CY 48, 1998.

Tulimieri et al., "Ordering of Helium Mixtures in Porous Gold" Phys. Rev. Lett. vol. 82, No. 1, pp. 1210124, Jan. 4, 1999.

Li et al., "Synthesis of Porous Ni—Ti Shape-Memory Alloys by Self-Propagating High-Temperature Synthesis: Reaction Mechanism and Anisotrophy in Pore Structure" Acta Mater. 48, pp. 3895-3904, 2000.

Pugh et al., "Formation of Nanoporous Platinum by Selective Dissolution of Cu from $Cu_{0.75}Pt_{0.25}$," J. Mater. Res., vol. 18, No. 1, Jan. 2003.

Newman et al., "Alloy Corrosion" MRS Bulletin 74(7), Jul. 24, 1999.

M. Grimwade, "The Surface Enrichment of Carat Gold Alloys—Depletion Gilding" Gold Technology, Issue 26, pp. 16-23, Jul. 1999.

Gertner et al., "Drug Delivery from Electrochemically Deposited Thin Metal Films" Electrochemical and Solid-State Letters, 6 (4), pp. J4-J6, 2003.

Stein et al., "Dealloying Studies with Electrodeposited Zinc-Nickel Alloy Films" Electrochimica Acta, vol. 43, Nos. 1-2, pp. 223-226, 1998.

Schroers, et al., "Amorphous Metallic Foam" Applied Physics Letters, vol. 82, No. 3, pp. 370-372, Jan. 20, 2003.

(56) References Cited

OTHER PUBLICATIONS

Wieneke et al., "Synergistic Effects of a Novel Nanoporous Stent Coating and Tacrolimus on Intima Proliferation in Rabbits" Catheterization and Cardiovascular Interventions, 60:pp. 399-407, 2003.
Ji et al., "Fabrication of Nanoporous Gold Nanowires" Applied Physics Letters, vol. 81, No. 23, pp. 4437-4439, Dec. 2, 2002.
Kazeminezhad et al., "Alloys by Precision Electrodeposition" Applied Physics Letters, vol. 78, No. 7, pp. 1014-1016, Feb. 12, 2001.
Sieradzki et al., "The Dealloying Critical Potential" Journal of the Electrochemical Society, 149(8), pp. B370-B377, 2002.
Itokazu et al., "Local Drug Delivery System Using Ceramics: Vacuum Method for Impregnating a Chemoterapeutic Agent Into a Porous Hydroxyapatite Block," Journal of Material Science: Materials of Medicine, vol. 10, No. 4, pp. 249-252, Apr. 1999.

\* cited by examiner

Poor Re-endothelialization on L605 bare metal.    Complete Re-Endothelialization on CES Bare Metal                CES + Sirolimus under 35 U.S.C.
NANOPOROUS STENTS WITH ENHANCED CELLULAR ADHESION AND REDUCED NEOINTIMAL FORMATION

CROSS-REFERENCE TO RELATED APPLICATIONS

The present application claims priority under 35 U.S.C. §119(e) to U.S. Provisional Application No. 60/809,465 filed on May 31, 2006, and is also a continuation-in-part of U.S. application Ser. No. 11/200,655 filed Aug. 10, 2005, now abandoned which 1) claims priority under 35 U.S.C. §119(e) to U.S. Provisional Application No. 60/602,542 filed on Aug. 18, 2004, U.S. Provisional Application No. 60/613,165 filed on Sep. 24, 2004, U.S. Provisional Application No. 60/664,376 filed on Mar. 23, 2005, and U.S. Provisional Application Ser. No. 60/699,302 filed Jul. 14, 2005, and 2) is a continuation-in-part of U.S. application Ser. No. 10/918,853 filed on Aug. 13, 2004, now abandoned which is a continuation-in-part of U.S. application Ser. No. 10/713,244 filed on Nov. 13, 2003, now U.S. Pat. No. 7,294,409 which claims priority under 35 U.S.C. §119(e) to U.S. Provisional Application No. 60/426,106 filed on Nov. 13, 2002, the disclosures of which are incorporated by reference herein in their entirety.

BACKGROUND OF THE INVENTION

Field of the Invention

The present invention relates generally to medical devices with porous layers and methods for making the same. More specifically, the invention relates to implantable medical devices having at least one porous layer, methods for making such devices and loading the porous layer with therapeutic agents. The porous layer may be used as a bonding interface for other coatings applied to the medical device, including drug-eluting coatings. The porous layer may have a random pore structure or an oriented or directional pore structure. The invention also relates to implantable medical devices having at least one porous layer that do not require loading with a therapeutic agent.

Description of the Related Art

Implantable medical devices are increasingly being used to deliver one or more therapeutic agents to a site within a body. Such agents may provide their own benefits to treatment and/or may enhance the efficacy of the implantable device. For example, much research has been conducted into the use of drug eluting stents for use in percutaneous transluminal coronary angioplasty (PTCA) procedures. Although some implantable devices are simply coated with one or more therapeutic agents, other devices include means for containing, attaching or otherwise holding therapeutic agents to provide the agents at a treatment location over a longer duration, in a controlled release manner, or the like.

Porous materials, for example, are commonly used in medical implants as reservoirs for the retention of therapeutic agents. Materials that have been used for this purpose include ceramics such as hydroxyapatites and porous alumina, as well as sintered metal powders. Polymeric materials such as poly(ethylene glycol)/poly(L-lactic acid) (PLGA) have also been used for this purpose.

SUMMARY OF THE INVENTION

It is desirable to modify medical devices, particularly coronary stents, in order to confer on these devices the ability to carry and elute therapeutic agents. To date, materials such as hydroxyapatites, porous alumina, sintered metal powders and polymers have been used for this purpose. Each has had its limitation. Polymer coatings, for example, have limitations related to coating adhesion, mechanical properties, inflammatory properties, and material biocompatibility, while porous alumina has severe issues with regard to mechanical integrity. The preferred embodiments of the invention related to nanoporous metallic surface modification as an alternative means of enabling targeted delivery of therapeutic agents from medical devices. The said surface modification results in one or more layers of porous metal on the surface of the medical device. The porous layers are then loaded with the therapeutic agent of choice, or a combination of such agents.

Some embodiments of the invention are geared toward producing a strongly adherent and mechanically robust biocompatible porous layer(s), while simplifying device manufacture and loading of therapeutic agents. The porous layer(s) are generated by the process of dealloying in which a sacrificial material is selectively removed from a precursor alloy on the medical device. The said precursor alloy may be formed by thin film deposition processes. The dealloying process can be effected both chemically and thermally, both methods of which are described in this invention. The morphology of the porous layer, e.g. pore size, thickness and tortuosity can be adjusted at point of manufacture to accommodate the need for different elution profiles as may be required by the medical application at hand. Within the same medical application, e.g. the treatment of coronary restenosis, different morphologies may be desired to accommodate different elution profiles for different therapeutic agents. The invention also comprises unique loading methods which, independently or in conjunction with the ability to vary morphology, allow one or more therapeutic agents to be loaded into the porous layers to achieve desired elution profiles. Some of the loading methods allow deposition of dilute or extremely dense crystalline forms of therapeutic agents within the porous structure thereby allowing a wide range of control over initial payloads within a relatively thin layer.

In addition, the porous layer(s) can be loaded with or bonded to drug-carrying polymers, such as those used currently with the Cypher stent, with the intent to improve the adhesion of said polymer(s) i.e. when the polymer flows into the porous layer(s), it solidifies to form a rooting or anchoring system. Alternatively, the porous layer(s) can be loaded with one or more therapeutic agents, prior to the application of a drug-free topcoat polymer to moderate elution kinetics. In one embodiment, biodegradable polymers are applied as a topcoat and through selection of polymer solvents with varying solubility properties for the therapeutic agents, one can achieve controlled mixing of the therapeutic agent with the polymer, as well as control the extent of penetration of the polymer-drug mixture into the porous layer.

One embodiment of the invention relates to implantable vascular stents or other biomedical devices having at least one nanoporous layer that promotes improved cellular adhesion properties that promote healing and long term biocompatibility. In the case of stents, the nanoporous layer promotes re-endothelialization at sites of stent implantation vasculature, improves overall healing, and reduces inflammation and intimal disease progression. The nanoporous layer may be optionally loaded with one or more therapeutic agent to further improve the function of the implanted stent and further augment clinical efficacy.

In another embodiment, a medical device for insertion into a body is provided, comprising a medical device having a porous surface exhibiting reduced neointimal formation compared to the same medical device lacking the porous surface. The porous surface may be a nanoporous surface and/or a dealloyed surface. The medical device may be a stent or a coronary stent. The medical device may exhibit a reduced percentage area of stenosis compared to the same medical device lacking the porous surface. The medical device may lack an elutable therapeutic agent or contain at least one therapeutic agent. The at least one therapeutic agent is selected from a group consisting of: actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, GLEEVEC (imatinib mesylate), wortmannin, PDGF inhibitors, AG1295 (6,7-Dimethyl-2-phenylquinoxaline), rho kinase inhibitors, Y27632 ((+)-(R)-trans-4-(1-aminoethyl)-N-(4-pyridyl)cyclohexanecarbonxamide dihydrochloride), calcium channel blockers, sphingosine phosphate inhibitors, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD34 antibodies, mycophenolic acid, Vitamin E, omega-3 fatty acids, tempamine, and docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radioisotope, a prodrug, antibody fragments, antibodies, live cells, therapeutic drug delivery microspheres or microbeads, gene therapy agents, viral vectors and plasmid DNA vectors.

In one embodiment of the invention, a stent for insertion into a body structure is provided. The stent comprises a tubular member having a first end and a second end, a lumen extending along a longitudinal axis between the first end and the second end, an outer or ablumenal surface and an inner or lumenal surface, and at least one porous layer where the porous layer comprises an interstitial structure and an interstitial space. The interstitial space is generally configured by the removal of at least one sacrificial material from a mixture comprising at least one sacrificial material with one or more structural materials that comprise the interstitial structure of the porous layer. The porous layer may be adapted to receive and release at least one therapeutic agent. The stent may also further comprise a therapeutic agent within at least a portion of the interstitial space. In one embodiment, the interstitial space is generally configured by a dealloying process. In one embodiment of the invention, at least a portion of the porous layer extends between the outer surface and the lumenal surface.

In one embodiment, the porous layer is adapted to bond to a drug eluting coating. The porous layer may have an average thickness of about 0.1 microns to about 1000 microns, and preferably about 0.1 microns to about 10 microns. The porous layer may have an average pore size of about 1 nanometer to about 100 microns. In other embodiments, the average pore size is about 10 nanometers to about 100 microns. The porous layer may have an average porosity of about 1% to about 99%, typically about 25% to about 75%, and preferably about 50% to about 70%. Most preferably, the porous layer has an average porosity of about 40% to about 60%. The stent may further comprise a non-metallic drug eluting coating bonded to at least a portion of the porous layer. The porous layer may be a metallic porous layer. The porous layer may be nanoporous. The drug eluting coating may be a polymeric or hydrogel drug eluting coating. The drug of the drug eluting coating may be selected from a group comprising actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, GLEEVEC (imatinib mesylate), wortmannin, PDGF inhibitors, AG1295 (6,7-Dimethyl-2-phenylquinoxaline), rho kinase inhibitors, Y27632 ((+)-(R)-trans-4-(1-aminoethyl)-N-(4-pyridyl)cyclohexanecarbonxamide dihydrochloride), calcium channel blockers, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD34 antibodies, mycophenolic acid, Vitamin E, omega-3 fatty acids, tempamine, and docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, a rifamycin including rifabutin, rifampin and rifapentine, an anti-convulsant including carbamazepine, phenobarbital and phenyloin, an anti-HIV agent including efavirenz and nevirapine, and an herbal agent including St. John's Wort, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radio-isotope, a prodrug, antibody fragments, antibodies, live cells, therapeutic drug delivery microspheres or microbeads, gene therapy agents, viral vectors and plasmid DNA vectors.

In one embodiment, the average pore size of the porous layer is within the range of about 1 nanometers to about 1,000 nanometers. In other embodiments, the average pore size of the porous layer is within the range of about 1 nanometers to about 100 nanometers and preferably within the range of about 1 nanometers to about 20 nanometers. In one embodiment of the invention, the structural material comprises gold and the average pore size of the porous layer is within the range of about 5 nanometers to about 500 nanometers.

The average thickness of porous layer in one embodiment is within the range of about 2 nanometers to about 5 mm. In another embodiment, the average thickness is within the range of about 5 nanometers to about 5 micrometers and preferably within the range of about 5 nanometers to about 50 nanometers. In still another embodiment, the average thickness of the porous layer is about 10 nanometers. In another embodiment of the invention, the average thickness is in the range of about 0.5 µm to 5 µm, and preferably about 0.1 µm. In another embodiment of the invention, the average thickness is in the range of about 0.5 um to 5 um, and preferably about 1 um to about 2 um.

In one embodiment, the interstitial volume per volume of porous layer is between about 10% and about 90%. The porous layer may have a substantially nonuniform interstitial volume per volume of porous layer. In some embodiments, the nonuniformity of the interstitial volume per volume of porous layer is graded. In other embodiments, the nonuniformity of the interstitial volume per volume of porous layer is abrupt. In one embodiment, the stent comprises a first zone having a first average interstitial volume per volume of porous layer and a second zone having a second average interstitial volume per volume of porous layer.

In some embodiments, the porous layer has a nonuniform pore size. The stent may comprise a first zone having a first average pore size and a second zone having a second average pore size. The pore size may transition gradually between the first zone and the second zone.

The porous layer may also have a nonuniform layer thickness. The stent may comprise a first thickness at a first point and a second thickness at a second point. The layer of thickness may transition gradually between the first point and the second point. In one embodiment, the porous layer has a substantially nonuniform pore size along the longitudinal axis of the tubular member. In one embodiment, the porous layer has a substantially nonuniform pore size circumferentially around the tubular member. In one embodiment, the porous layer has a nonuniform layer thickness along the longitudinal axis of the tubular member and in one embodiment, the porous layer has a nonuniform layer thickness around the circumference of the tubular member. The interstitial volume per volume of porous layer may also be nonuniform along the longitudinal axis of the tubular member and also nonuniform around the circumference of the tubular member.

In another embodiment, the stent further comprises at least one therapeutic agent that is at least partially contained within the interstitial space of the porous layer. The therapeutic agent is selected from the group comprising actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, GLEEVEC (imatinib mesylate), wortmannin, PDGF inhibitors, AG1295 (6,7-Dimethyl-2-phenylquinoxaline), rho kinase inhibitors, Y27632 ((+)-(R)-trans-4-(1-aminoethyl)-N-(4-pyridyl)cyclohexanecarbonxamide dihydrochloride), calcium channel blockers, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD34 antibodies, mycophenolic acid, Vitamin E, omega-3 fatty acids, tempamine, and docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, a rifamycin including rifabutin, rifampin and rifapentine, an anti-convulsant including carbamazepine, phenobarbital and phenyloin, an anti-HIV agent including efavirenz and nevirapine, and an herbal agent including St. John's Wort, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radio-isotope, a prodrug, antibody fragments, antibodies, live cells, therapeutic drug delivery microspheres or microbeads, gene therapy agents, viral vectors and plasmid DNA vectors.

In some embodiments, at least a portion of the ablumenal surface of the tubular member comprises a first porous layer and at a least portion of the lumenal surface of the tubular member comprises a second porous layer. In some embodiments, at least a portion of the interstitial space of the first porous layer is preferably filled with a therapeutic agent selected from the group comprising actinomycin-D, batimistat, c-myc antisense, dexamethasone, paclitaxel, taxanes, sirolimus, tacrolimus and everolimus. The second porous layer may be preferably filled with a therapeutic agent selected from the group comprising actinomycin-D, batimistat, c-myc antisense, dexamethasone, paclitaxel, taxanes, sirolimus, tacrolimus and everolimus, unfractionated heparin, low-molecular weight heparin, enoxaprin, synthetic polysaccharides, ticlopinin, dipyridamole, clopidogrel, fondaparinux, streptokinase, urokinase, r-urokinase, r-prourokinase, rt-PA, APSAC, TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD34 antibodies, mycophenolic acid, Vitamin E, omega-3 fatty acids, tempamine, and docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, a rifamycin including rifabutin, rifampin and rifapentine, an anti-convulsant including carbamazepine, phenobarbital and phenyloin, an anti-HIV agent including efavirenz and nevirapine, and an herbal agent including St. John's Wort, and bivalirudin.

In one embodiment of the invention, the porous layer further comprises at least one elution rate altering material within or about at least a portion of the interstitial space of the porous layer. The stent may further comprise at least one therapeutic agent within at least a portion of the interstitial space. In some embodiments, the elution rate altering material is distinct from the therapeutic agent. In other embodiments, the elution rate altering material is mixed with the therapeutic agent. The elution rate altering material may comprise a diffusion barrier or a biodegradable material or a polymer or hydrogel. In one embodiment, the porous layer further comprises a first elution rate altering layer, a first therapeutic agent, a second elution rate altering layer and a second therapeutic agent where the first elution rate altering layer comprises a first elution rate altering material and the second elution rate altering layer comprises a second elution rate altering material. The first elution rate altering material may be different from the second elution rate altering material. The first therapeutic agent may be different from the second therapeutic agent. The first elution rate altering layer may have an average thickness different from the average thickness of the second elution rate altering material.

In one embodiment of the invention, at least one sacrificial material is nonmetallic. At least one sacrificial material may be selected from the group consisting of glass, polystyrene, plastics, alumina, salts, proteins, carbohydrates, and oils. In one embodiment, at least one structural material is nonmetallic. At least one structural material may be selected from a list comprising silicon dioxide, silicon nitride, silicon, polystyrene, sodium chloride, and polyethylene. In some embodiments of the invention, the stent comprises a first a porous layer and a second porous layer where at least a portion of the first porous layer is positioned between at least a portion of the second porous layer and a portion of the tubular member. In some embodiments, the interstitial space is configured generally by the removal of at least two sacrificial materials from a mixture comprising at least two sacrificial materials and at least one structural material with the structural material forming at least a portion of the interstitial structural of the porous layer. The interstitial structure may comprise at least one material selected from the group consisting of gold, silver, nitinol, steel, chromium, iron, nickel, copper, aluminum, titanium, tantalum, cobalt, tungsten, palladium, vanadium, platinum, niobium, a salt, and an oxide particle. The interstitial space may be configured by removing at least one sacrificial material with a dealloying process. The interstitial space may also be configured by removing at least one sacrificial material with a high-pressure evaporation. In some embodiments of the stent, the therapeutic agent is loaded onto the stent through exposure to a solution containing the therapeutic agent. In some embodiments, the therapeutic agent is loaded onto the stent in an environment less than 760 torr. In some embodiments, the solution comprises a solvent. The solvent may have a high solubility product for the therapeutic agent but a vapor pressure less than water. The therapeutic agent may be loaded onto the stent while the solvent resorbs at least some of the gaseous material within the interstitial space. The gaseous material may comprise the vapor form of the solvent. The therapeutic agent may be loaded onto the stent in a super cooled environment or by use of sequential load-dry steps with supersaturated solutions of the therapeutic agent.

In one embodiment of the invention, a therapy-eluting medical device is provided. The device comprises at least one component of a medical device having at least one therapy-eluting surface comprising an interstitial structure and an interstitial space where the interstitial space is configured generally by the removal of at least a portion of one sacrificial material from a mixture comprising at least one sacrificial material in one or more structural materials that comprise the interstitial structure of the porous layer and where the therapy-eluting medical device is adapted to receive and release at least one therapeutic agent. The medical device may be a stent, a vascular graft, an orthopedic device, an implantable sensor housing, an artificial valve, a contraceptive device, an inter-uterine device, a subcutaneous hormonal implant, a wire coil, a neural coil, a vascular coil for treatment of an aneurysm, a suture, a staple, a guidewire or a catheter.

In one embodiment of the invention, a therapy-eluting medical device is provided. The device comprises at least one component of a medical device having at least one therapy-eluting surface comprising an interstitial structure and interstitial space where the interstitial structure and the interstitial space are configured from a precursor matrix with a directional grain structure, where the configuration is generally determined by the removal of at least a portion of the precursor matrix with respect to the directional grain structure and where the therapy-eluting medical surface is adapted to receive and release at least one therapeutic agent. The medical device may be a stent, a vascular graph, an orthopedic device, an implantable sensor housing, an artificial valve, a contraceptive device, an inter-uterine device, a subcutaneous hormonal implant, a wire coil, a neural coil, a vascular coil for treatment of an aneurysm, a suture, a staple, a guidewire or a catheter. The removal of at least a portion of the precursor matrix is performed by at least one etchant. The configuration may be additionally modified by a secondary etchant. The secondary etchant may be an isotropic etchant or an anisotropic etchant.

In one embodiment of the invention, a therapy-eluting medical device is provided. The device comprises at least one component of a medical device having at least one therapy-eluting surface comprising an interstitial structure and an interstitial space where the interstitial space is configured generally by the removal of at least a portion of one sacrificial material from a mixture comprising at least one sacrificial material in one or more structural materials that comprise the interstitial structure of the porous layer and where the therapy-eluting medical device is adapted to receive and release at least one therapeutic agent. The medical device may be a stent, a vascular graph, an orthopedic device, an implantable sensor housing, an artificial valve, a contraceptive device, an inter-uterine device, a subcutaneous hormonal implant, a wire coil, a neural coil, a vascular coil for treatment of an aneurysm, a suture, a staple, a guidewire or a catheter.

In one embodiment of the invention, a therapy-eluting medical device is provided. The device comprises at least one component of a medical device having at least one porous coating interface comprising an interstitial layer and an interstitial space, wherein the interstitial layer is configured generally by the removal of at least a portion of one sacrificial material from a mixture comprising at least one sacrificial material and one or more structural materials that comprise the interstitial structure of the porous coating interface, and a drug eluting coating bonded to at least a portion of the porous coating interface. The porous coating interface may be a metallic porous coating interface. The porous coating interface may be nanoporous. The porous coating interface may have an average thickness of about 0.1 microns to about 1000 microns, and preferably about 0.1 microns to about 10 microns. The porous coating interface may have an average pore size of about 1 nanometer to about 100 microns. In other embodiments, the average pore size is about 10 nanometers to about 100 microns. In still other embodiments, the average pore size is about 0.1 to about 50 nanometers. The porous layer may have an average porosity of about 1% to about 99%, typically about 25% to about 75%, and preferably about 50% to about 70%. In one embodiment, the porous layer has an average porosity of about 40% to about 70%. The drug eluting coating may be a polymeric or hydrogel drug eluting coating. The drug of the drug eluting coating may be selected from a group comprising actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, GLEEVEC (imatinib mesylate), wortmannin, PDGF inhibitors, AG1295 (6,7-Dimethyl-2-phenylquinoxaline), rho kinase inhibitors, Y27632 ((+)-(R)-trans-4-(1-aminoethyl)-N-(4-pyridyl)cyclohexanecarbonxamide dihydrochloride), calcium channel blockers, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD34 antibodies, mycophenolic acid, Vitamin E, omega-3 fatty acids, tempamine, and docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, a rifamycin including rifabutin, rifampin and rifapentine, an anti-convulsant including carbamazepine, phenobarbital and phenyloin, an anti-HIV agent including efavirenz and nevirapine, and also herbal agent including St. John's Wort, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radio-isotope, a prodrug, antibody fragments, antibodies, live cells, therapeutic drug delivery microspheres or microbeads, gene therapy agents, viral vectors and plasmid DNA vectors.

In another embodiment of the invention, a polymer coated drug delivery stent is provided. The stent comprises a tubular metal stent body, a porous layer on the body and a drug delivery layer having a first side which extends into the porous layer and a second, exposed side for releasing a drug. In another embodiment, the stent comprises a tubular metal stent body, a porous layer on the body, a tie layer which is mechanically bonded to the porous layer and a drug delivery layer bonded to the tie layer.

In another embodiment, the device comprises at least one component of a medical device having at least one therapy-eluting surface comprising a interstitial structure and an interstitial space wherein the interstitial structure and the interstitial space are configured from a precursor matrix with a directional grain structure, wherein the configuration is generally determined by the removal of at least a portion of the precursor matrix with respect to the directional grain structure. The porous layer may be adapted to absorb a range of substances. In another embodiment, the porous layer is adapted to facilitate tissue ingrowth over the porous layer. The tissue ingrowth may result from promotion of cell anchoring. A unique aspect of one embodiment of the invention is that the porous layer contains nanopores of size to promote cell and tissue anchoring but below the scale known to activate adverse cellular responses including platelet or leucocyte activation. In some embodiments, the preferred average pore size for promoting cell and tissue anchoring are about 1 nm to about 3000 nm, and preferably about 20 nm to about 200 nm, or about 10 nm to about 100 nm. In some embodiments, porous layers having a peak to valley roughness of less than about 3 microns may be associated with improved cell and tissue anchoring to the porous biomedical device. In other embodiments, a porous zone having a peak-to-valley roughness of less than about 2 microns, or preferably less then 0.5 microns are used to improve cell and tissue anchoring. The porous layer may also be adapted to facilitate bonding of a polymeric coating to the porous layer.

In one embodiment, a method of making a drug delivery stent is provided. The method comprises the steps of providing a stent having a porous surface and applying a drug delivery layer to the porous surface under conditions which cause a portion of the drug delivery layer to advance into the porous surface to provide a bond between the porous surface and the drug delivery layer. In another embodiment, the method comprises the steps of bonding a tie layer to the porous surface and bonding a drug delivery layer to the tie layer.

In another embodiment, a method of reducing the risk of delamination between a stent and a polymeric drug delivery layer during balloon expansions of the stent is provided, comprising the steps of providing the stent with a porous surface and bonding the drug delivery layer to the porous surface. The drug delivery layer may be bonded directly to the stent, or bonded to a tie layer which is bonded to the stent. In another embodiment, the method comprises providing a stent having a drug delivery layer, radially dilating the stent and retaining the drug delivery layer on the stent by a plurality of links between the drug delivery layer and pores in the stent.

In one embodiment of the invention, a therapy-eluting medical device is provided. The device comprises at least one component of a medical device having at least one porous surface comprising a interstitial structural in an interstitial space wherein the interstitial space is configured generally by the removal of at least a portion of one sacrificial material from a mixture comprising at least one sacrificial material in one more structural materials that comprise the interstitial structure of the porous layer. The porous layer may be adapted to absorb a range of substances. In another embodiment, the porous layer adapted to facilitate tissue ingrowth over the porous layer.

In one embodiment, a method for manufacturing a medical device with at least one nonpolymeric porous layer is provided. The method comprises the steps of providing at least a component of a medical device having at least one surface and depositing a layer of material onto a least a portion of the surface. The layer of material comprises at least one sacrificial component and at least one structural component where at least one component is not a polymer or a therapeutic agent. In one embodiment, the depositing step comprises high-pressure sputtering of the material. The depositing step may also comprise directed vapor deposition or sintering. The material may comprise a powder or beads. The method may further comprise the step of removing at least a portion of at least one sacrificial component to form an interstitial space. The removing step may comprise applying a solvent to at least a portion of at least one sacrificial component. The removing step may also comprise applying a solvent/therapeutic agent combination to at least a portion of at least one sacrificial component. The method may further comprise applying a magnetic field to at least a portion of the component of the medical device to at least partially orient at least one component of the layer of the material. The method may also further comprise varying the intensity or direction of the magnetic field during the depositing step. The method may also further comprise the steps of removing at least one sacrificial material from the layer of mix materials to form a porous layer. In some embodiments, the porous layer has a metallic structure.

In one embodiment, a method for manufacturing a medical device with at least one porous layer is provided. The method comprises the steps of providing at least a component of a medical device having at least one surface and depositing a material onto a least a portion of the surface using a high pressure to form a layer having a directional grain and removing at least a portion of the deposited material with respect to the directional grain to form an interstitial space. The layer of deposited material may comprise at least one sacrificial component and at least one structural component. In one embodiment, the removing step comprises applying an etchant. The etchant may be selected from the group comprising nitric acid, sulphuric acid, hydrofluoric acid, hydrochloric acid, ammonium fluoroide, sodium hydroxide, potassium hydroxide, or ferric chloride. The etchant is preferably nitric acid. The method may further comprise modifying the interstitial space with a secondary etchant. The secondary etchant may be an isotropic etchant or an anisotropic etchant. The removing step may also comprise applying a solvent/therapeutic agent combination to at least a portion of at least one sacrificial component. The method may further comprise the step of applying a magnetic field to at least a portion of the component of the medical device to at least partially orient the depositing of the material with respect to the medical device. The intensity or direction of the magnetic field may be varied during the depositing step. The method may also further comprise the step of removing at least one sacrificial material from the layer of mix materials to form a porous layer. In some embodiments, the porous layer has a metallic structure. The depositing step may be performed by sputtering, thermal evaporation, electron-beam evaporation, laser ablation, chemical vapor deposition, and ion beam sputtering.

In one embodiment, a method of loading a porous medical device with a therapeutic agent is provided. The method comprises the steps of providing at least a component of a medical device having a dealloyed porous zone. The dealloyed porous zone comprises an interstitial structure and an interstitial space and filling at least a portion of the interstitial space with at least one therapeutic agent. The filling step may be performed by placing at least a portion of the interstitial space of the medical device into a solution containing the therapeutic agent, spraying a solution containing the therapeutic agent onto at least a portion of the interstitial space of the medical device, placing at least a portion of the interstitial space of the medical device into a flow of a solution containing a therapeutic agent, or placing at least a portion of the interstitial space of the medical device into a loading vessel and filling the vessel with a solution containing the therapeutic agent. In one embodiment, the loading vessel is designed to minimize the drug loading solution required for loading the biomedical device. The method may further comprise the step of preparing the interstitial space for filling with the therapeutic agent. The preparing step may also comprise evacuating at least a portion of any gaseous material from at least a portion of the interstitial space. The filling step may be performed in a sub-atmospheric environment or a vacuum environment. The preparing step may comprise evacuating gaseous material from at least a portion of the interstitial space by exposing at least a portion of the interstitial space to a sub-atmospheric pressure. The preparing step may comprise applying an electrical charge to the interstitial structure or exposing at least a portion of the interstitial structure to a gaseous material. This gaseous material may comprise a solvent soluble gaseous material to facilitate removal of trapped gas. The therapeutic agent of the filling step may also be provided in a gaseous material soluble solvent. In the form of a gaseous material soluble solvent, the therapeutic agent causes "prewetting" of the porous structure with the gas phase of the drug loading solvent and thereby facilitates the loading process. The method may further comprise reabsorbing at least a portion of the gaseous material into the gaseous material soluble solvent. The therapeutic agent may also comprise a therapeutic substance and a carrier. The method may further comprise precipitating the therapeutic substance in the interstitial space. The precipitating step may be performed by removal of at least a portion of the carrier from the interstitial space. The carrier may comprise a substance selected from the group consisting of an alcohol, water, ketone, a lipid, and an ester. The carrier may also comprise a solvent where the solvent is selected from a group comprising de-ionized water, ethanol, methanol, DMSO, acetone, benzyl alcohol, and chloroform. The solvent may have sufficient solubility product for the therapeutic agent but a vapor pressure less than water. The filling step may be performed at a vapor pressure generally between the vapor pressure of the solvent but less than water. The method may further comprise exposing at least a portion of the interstitial space of the medical device to an aqueous solution with a low solubility product for the therapeutic agent. In some embodiments, the exposing step is performed after the filling step. The method may further comprise the step of exposing the device to a below ambient pressure environment for the filling step. The below ambient pressure environment may be below 760 torr, below about 380 torr, below about 190 torr, below about 100 torr, below about 60 torr, or below about 30 torr. At least a portion of the below ambient pressure environment may be achieved through supercooling the environment. The latter also permits the use of lower pressures to facilitate loading steps by reducing the solvent vapor pressure. After prewetting the porous structure at low temperature, the device may be mechanically immersed into drug-loading solvent while at low pressure, then the pressure is gradually increased to force drug loading solution into the porous layer. Alternatively, or in addition, the method may comprise the step of exposing the device to an above-ambient pressure environment for at least a portion of the filling step. The method may further comprise the step of loading a propellant into the interstitial space. This loading step may be performed before the filling step. The method may further comprise determining the amount of therapeutic agent filling the interstitial space, changing the amount of therapeutic agent filling the interstitial space or on the surface of the nanoporous coating. The filling step may be performed at the point of use or at the point of manufacture.

In another embodiment, a method of loading a porous medical device with a therapeutic agent is provided. The method comprises the steps of providing at least a component of a medical device having a nanoporous zone where the nanoporous zone comprises an interstitial structure and an interstitial space, displacing any gaseous material within the interstitial space with a vapor form of a first solvent and filling at least a portion of the interstitial space with at least one therapeutic agent. The filling step may be performed in a subatmospheric environment or a vacuum environment. The method may further comprise the step of preparing the interstitial space for filling with the therapeutic agent. The preparing step may also comprise evacuating gaseous material from at least a portion of the interstitial space by exposing at least a portion of the interstitial space to sub-atmospheric pressure. The preparing step may comprise applying electrical charge to the interstitial structure or exposing at least a portion of the interstitial structure to a gaseous material including the gaseous or vapor phase of the solvent in which a therapeutic agent is dissolved or other gases that have a high degree of solubility in the loading solvent. The first solvent may be ethanol, methanol, or other loading solvent that can be vaporized under conditions compatible with integrity/viability of the therapeutic agent. The method may further comprise condensing the vapor form of the first solvent to a liquid form and mixing the condensed liquid form of the first solvent with an exogenously applied liquid form of the first solvent. The therapeutic agent may also comprise a therapeutic substance and a carrier. The therapeutic agent may be loaded onto the medical device by use of sequential load-dry steps with supersaturated solutions of the therapeutic agent. The method may further comprise precipitating the therapeutic substance in the interstitial space. The precipitating step may be performed by removal of at least a portion of the carrier from the interstitial space. The carrier may also comprise a second solvent. The second solvent may be miscible with the liquid form of the first solvent. The second solvent may be selected from a group comprising de-ionized water, ethanol, methanol, DMSO, acetone and chloroform. The second solvent may have sufficient solubility product for the therapeutic agent but a vapor pressure less than water. The filling step may be performed at a vapor pressure generally between the vapor pressure of the solvent but less than water. The method may further comprise exposing at least a portion of the interstitial space of the medical device to an aqueous solution with a low solubility product for the therapeutic agent. In some embodiments, the exposing step is performed after the filling step. The method may further comprise the step of exposing the device to a below ambient pressure environment for the filling step. The below ambient pressure environment may be below 760 torr, below about 380 torr, below about 190 torr, below about 100 torr, below about 60 torr, or below about 30 torr. At least a portion of the below ambient pressure environment may be achieved through supercooling the environment to reduce the vapor pressure of the first solvent used for loading the therapeutic agent. Alternatively, or in addition, the method may comprise the step of exposing the device to an above-ambient pressure environment for at least a portion of the filling step. The method may further comprise the step of loading a propellant into the interstitial space. This loading step may be performed before the filling step. The method may further comprise determining the amount of therapeutic agent filling the interstitial space, changing the amount of therapeutic agent filling the interstitial space or on the surface of the nanoporous coating. The filling step may be performed at the point of use or at the point of manufacture.

In one embodiment of the invention, a method of treating a patient is provided. The method comprises the steps of providing a medical device with a nanoporous component loaded with a therapeutic agent placing the medical device at a treatment site and releasing at least a portion of the therapeutic agent from the porous component under active pressure. The active pressure may be generated by a propellant loaded into the porous component. The releasing step of at least a portion of the therapeutic agent may be performed by the therapeutic agent loaded into the porous component at a pressure higher than physiologic pressure or at a pressure of at least 180 mm Hg, 250 mm Hg or at least 300 mm Hg.

In another embodiment, a method of treating a patient is provided. The method comprises the steps of providing a medical device with a directional nanoporous component loaded with a therapeutic agent placing the medical device at a treatment site and releasing at least a portion of the therapeutic agent from the directional nanoporous component under active pressure. The active pressure may be generated by a propellant loaded into the nanoporous component. The releasing step of at least a portion of the nanoporous agent may be performed by the therapeutic agent loaded into the nanoporous component at a pressure higher than physiologic pressure or at a pressure of at least 180 mm Hg, 250 mm Hg or at least 300 mm Hg.

In one embodiment, a method of treating a patient is provided. The method comprises the steps of providing a medical device with a porous component loaded with a pro-drug placing the medical device at a treatment site releasing at least a portion of the pro-drug from the porous component and reacting the prodrug generally within the treatment site to form an active drug. The treatment site may be a coronary artery or a portion of the biliary tree. Reacting step may be performed by white blood cells, myeloperoxidase released by white blood cells, macrophages or by renin located in the vascular wall. In some embodiments, the reacting step is performed with a reactant loaded into the medical device. The method may further comprise removing at least a portion of the any surface deposited therapeutic agent. The method may further comprise batch washing the component with a solvent with known solubility for the therapeutic agent or the solvent of the batch washing may be a defined volume of solvent. The method may further comprise altering the amount of therapeutic agent by exposing the component to controlled airstreams or air blasts. The method may be also be performed using high velocity airstreams or air blasts or by controlled mechanical wiping or by washing with one or more solvents with known solubility for the therapeutic agent or agents. Washing step may be performed with a defined volume of at least one solvent.

In one embodiment, a device for loading porous medical devices with a therapeutic agent is provided. The device comprises a vacuum chamber, a vacuum pump attached to the vacuum chamber, a therapeutic reagent housing, a flow controller attached to the therapeutic reagent housing and porous device holder within the vacuum chamber. In some embodiments, the device further comprises a loading device designed to minimize the volume of drug loading solutions preferably for implementing the loading methods described herein. The flow controller may be a controllable pump generally between the therapeutic reagent housing and the porous device holder. In one embodiment, the flow controller comprises a hinge generally attached to one end of the therapeutic reagent and a releasable housing support generally attached to the other end of the therapeutic reagent housing. In one embodiment, the loading device is configured to minimize the volume of loading solution required to load a given biomedical device. In another embodiment, the loading device is designed to optimize the flow of loading solvent to promote uniformity of loading to each device in a multidevice loading system. A preferred design is one that optimizes all loading parameters including drug quantities, loading volumes, and uniformity of loading between devices.

In one embodiment, a polymer coated drug delivery stent is provided. The stent comprises a tubular metal stent body, a porous layer on the body and a drug delivery layer having a first side which extends into the porous layer and a second, exposed side for releasing the drug. The porous layer may be a nanoporous layer. The porous layer may also be generally configured by the removal of at least one sacrificial material from a matrix comprising at least one sacrificial material with one or more structural materials that comprise the porous layer. In one embodiment, the porous layer may be a nanoporous layer. The porous layer may have an average pore size of about 1 nanometer to about 1000 nanometers. In one embodiment, the porous layer is generally configured by the removal of at least one sacrificial material from a matrix comprising at least one sacrificial material with one or more structural materials that comprises the porous layer. In another embodiment, a tie layer is mechanically bonded to the porous layer and the drug delivery layer bonded to the tie layer.

In another embodiment, a stent for insertion into a body structure is provided. The stent comprises a tubular member having a first end and a second end, a lumen extending along a longitudinal axis between the first end and the second end, an outer surface, an inner lumenal surface and at least one porous layer, the porous layer comprising an interstitial structure and an interstitial space, wherein the interstitial space is generally configured by the removal of at least a portion of at least one sacrificial material by a thermal dealloying process from a mixture comprising at least one sacrificial material with one or more structural materials that comprise the interstitial structure of the porous layer and wherein the porous layer is adapted to receive and release at least one therapeutic agent. At least one sacrificial material may be selected for its boiling point and/or vapor pressure. The thermal dealloying process comprises the application of a heat source. The heat source may be a light source such as a laser, infrared light source, or ultraviolet light source. The heat source may also be an inductive heat source or ultrasound heat source. In some embodiments, at least one sacrificial material comprises a form of magnesium. The application of a heat source may be performed in a vacuum of about $10^{-5}$ torr or less, $10^{-6}$ torr or less, $10^{-9}$ torr or less. The heat source may be capable of heating a portion of the mixture to at least about 400° C., at least about 500° C., or at least about 600° C. The porous of the pores of the porous layer may be modified by the application of an etchant to the porous layer. The etchant may have anisotropic or isotropic properties.

In one embodiment, a therapy-eluting medical device is provided. The device comprises at least one component of a medical device having at least one therapy-eluting surface comprising an interstitial structure and an interstitial space, wherein the interstitial space is configured generally by the removal of at least a portion of one sacrificial material by a thermal dealloying process from a mixture comprising at least one sacrificial material and one or more structural materials that comprise the interstitial structure of the porous layer; and wherein the therapy-eluting surface is adapted to receive and release at least one therapeutic agent.

In one embodiment, a method of making a drug delivery stent is provided. The method comprises the steps of providing a stent having a porous surface, applying a drug delivery layer to the porous surface under conditions which cause a portion of the drug delivery layer to advance into the porous surface to provide a bond between the porous surface and the drug delivery layer. The porous layer may be a nanoporous layer. The porous layer may have an average pore size of about 1 nanometer to about 1000 nanometers. In one embodiment, the porous layer is generally configured by the removal of at least one sacrificial material from a matrix comprising at least one sacrificial material with one or more structural materials that comprises the porous layer.

In one embodiment, a method of making a drug delivery stent is provided. The method comprises the steps of providing a stent having a porous surface, bonding a tie layer to the porous surface and bonding a drug delivery layer to the tie layer. The porous layer may be a nanoporous layer. The porous layer may have an average pore size of about 1 nanometer to about 1000 nanometers. In one embodiment, the porous layer is generally configured by the removal of at least one sacrificial material from a matrix comprising at least one sacrificial material with one or more structural materials that comprises the porous layer.

In another embodiment, a method for manufacturing a medical device with at least one non-polymeric porous layer is provided, comprising the steps of providing at least a component of a medical device having at least one surface; and depositing a layer of a material onto at least a portion of the surface; the layer of material comprising at least one sacrificial component and at least one structural component and at least one component is not a polymer or therapeutic agent; and thermally removing at least a portion of at least one sacrificial component to form an interstitial space. The method may further comprise increasing the interstitial space with an etchant. The etchant may have isotropic properties or anisotropic properties. The thermally removing step may be performed in a vacuum. The thermally removing step may be performed in using a laser.

In another embodiment of the invention, a stent for insertion into a body structure is provided, comprising a tubular member having a first end and a second end, a lumen extending along a longitudinal axis between the first end and the second end, an outer surface, an inner lumenal surface; and at least one porous layer, the porous layer comprising an interstitial structure and an interstitial space wherein the interstitial space is generally configured by the removal of at least a portion of at least one sacrificial material from a mixture comprising at least one sacrificial material with one or more structural materials that comprise the interstitial structure of the porous layer and removal of interstitial structure with an etchant and wherein the porous layer is adapted to receive and release at least one therapeutic agent. The etchant may be an isotropic etchant or an anisotropic etchant.

In one embodiment, a method of reducing the risk of delamination between a stent and a polymeric drug delivery layer during balloon expansion of the stent is provided. The method comprises providing the stent with a porous surface and bonding the drug delivery layer to the porous surface. The porous layer may be a nanoporous layer. The porous layer may have an average pore size of about 1 nanometer to about 1000 nanometers. In one embodiment, the porous layer is generally configured by the removal of at least one sacrificial material from a matrix comprising at least one sacrificial material with one or more structural materials that comprises the porous layer. The drug delivery layer may be bonded directly to the stent, or to the tie layer which is bonded to the stent.

In one embodiment, a method of reducing the risk of de-lamination between a stent and a polymeric drug delivery layer during balloon expansion of the stent is provided. The method comprises providing a stent having a drug delivery layer, radially dilating the stent; and retaining the drug delivery layer on the stent by a plurality of links between the drug delivery layer and pores in the stent. The pores may be nanopores. The pores may have an average pore size of about 1 nanometer to about 1000 nanometers.

In one embodiment, a method of loading multiple therapeutic agents onto a medical device is provided. The method comprises providing a medical device with a porous surface, loading a first therapeutic agent into the porous surface, and bonding a first coating onto at least a portion of the porous surface, wherein the first coating comprises at least one polymer and a second therapeutic agent. The porous surface may be dealloyed. The porous surface may also be a nanoporous surface. The method may further comprise bonding a second coating to at least a portion of the porous surface, wherein the second coating comprises at least one polymer and a second therapeutic agent. The second coating may also be bonded to at least a portion of the first coating.

In one embodiment of the invention, an implantable medical device comprises at least one directional porous layer having an interstitial structure and an interstitial space. In one embodiment, the directional porous layer comprises a metallic precursor matrix with a directional grain structure that is sputtered onto the tubular member and is at least partially configured by at least some preferential removal of the matrix with respect to the grain structure of the metallic precursor matrix. The porous layer may be adapted to receive and release at least one therapeutic agent. The metallic precursor matrix comprises at least one structural material and at least one sacrificial material. In one embodiment, the filamentary porous layer further comprises a metallic precursor matrix that is at least partially configured by the removal of at least some of the at least one sacrificial material. In one embodiment of the invention, the metallic precursor matrix comprises one or more subcomponent materials selected from a list comprising L605 alloy, gold, silver, nitinol, steel, chromium, iron, nickel, copper, aluminum, titanium, tantalum, cobalt, tungsten, palladium, vanadium, platinum, niobium, magnesium, a salt, oxide particle, silicon dioxide, polystyrene, and polyethylene. In one embodiment, the metallic precursor matrix preferably comprises L605 alloy. The stent may further comprise a therapeutic agent within at least a portion of the porous layer. The removal of matrix may be performed by at least one etchant. The etchant may have isotropic and/or anisotropic properties.

In one embodiment, a device for treating a patient is provided. The device comprises a medical device comprising a porous layer, the porous layer having a porous volume, a first therapeutic agent within the porous layer in a concentration of at least 5 times the concentration as calculated by the porous volume of the porous layer multiplied by the highest concentration of the first therapeutic agent in a solvent solution. Sometimes, the first therapeutic agent within the porous layer has a concentration of at least 10 times the concentration as calculated by the porous volume of the porous layer multiplied by the highest concentration of the first therapeutic agent in a solvent solution, or at least 25 times, or even at least 50 times the concentration as calculated by the porous volume of the porous layer multiplied by the highest concentration of the first therapeutic agent in a solvent solution. The device may further comprise a second therapeutic agent within the porous layer in a concentration of at least 5 times the concentration as calculated by the porous volume of the porous layer multiplied by the highest concentration of the second therapeutic agent in a solvent solution.

In another embodiment, a method of treating a patient is provided. The method comprises the steps of providing a medical device with a dealloyed porous component and placing the medical device at a treatment site. The dealloyed porous component need not contain a therapeutic agent. The porous component may also be configured for enhanced tissue ingrowth, for reduced friction with adjacent tissue when implanted in a lumen, for enhanced anchoring of the tubular member within a lumen, for enhanced cellular adhesion, for reduced mechanical interactions with surrounding tissue, for reduced mechanical interactions with surrounding tissue, to comprise a degradable form of a metal configured to affect surrounding tissue, and/or to promote tissue healing.

In one embodiment, a stent for insertion into a body structure is provided, comprising a tubular member comprising: a first end and a second end, a lumen extending along a longitudinal axis between the first end and the second end, an ablumenal surface, a lumenal surface; a first porous layer, the first porous layer comprising a first surface, a first interstitial structure and a first interstitial space; wherein the porous layer has a tortuosity factor of greater than about 1.1, an average thickness of less than 10 microns and a peak-valley surface roughness of less than about 2 microns. In some embodiments, the porous layer has a tortuosity factor of greater than about 1.6. The tubular member may further comprise a second porous layer, the second porous layer comprising a second surface, a second interstitial structure and a second interstitial space, or a second porous layer, the second porous layer comprising a second interstitial structure, a second interstitial space, and a first porous layer interface between the first porous layer and the second porous layer. The tubular member may exhibit improved radio-opacity compared a similar tubular member lacking the first porous layer. The average thickness of the first porous layer may be less than about 5 microns. The tortuosity factor of the first porous layer may be measured in a porous space comprising at least four pores. The first interstitial space may optionally have an angular component, may be located on the outer surface of the tubular member, may be located on the inner surface of the tubular member, may further comprise at least one therapeutic agent within at least a portion of the interstitial space, may be a metallic porous layer, and/or may be a nanoporous layer. In some embodiments, the nanoporous layer has an average pore diameter of less than about 200 nm, or sometimes less than about 5 nm. In some embodiments, the therapeutic agents within at least a portion of the first interstitial space are selected from a group comprising: actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, GLEEVEC (imatinib mesylate), wortmannin, PDGF inhibitors, AG1295 (6,7-Dimethyl-2-phenylquinoxaline), rho kinase inhibitors, Y27632 ((+)-(R)-trans-4-(1-aminoethyl)-N-(4-pyridyl)cyclohexanecarboxaminde dihydrochloride), calcium channel blockers, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD34 antibodies, mycophenolic acid, Vitamin E, omega-3 fatty acids, tempamine, and docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radio-isotope, a prodrug, antibody fragments, antibodies, live cells, therapeutic drug delivery microspheres or microbeads, gene therapy agents, viral vectors and plasmid DNA vectors. The first porous layer may further comprise at least one metabolic agent within at least a portion of the interstitial space for altering the metabolization of the at least one therapeutic agent. In some embodiments, at least one metabolic agent is a cytochrome P450 inhibitor, and sometimes the at least one metabolic agent is ritonavir. The stent may optionally further comprise a polymeric coating bonded to at least a portion of the outer surface of the porous layer. The polymeric coating may be a drug eluting coating, and may be an elution rate-controlling coating. In some instances, the polymeric coating comprises a material selected from a group consisting of: polyurethanes, silicones, polyesters, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxymethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Other coating materials may include lactone-based copolyesters, polyanhydrides, polyaminoacids, polysaccharides, polyphosphazenes, poly(ether-ester) copolymers, and blends of such polymers, poly (ethylene) vinylacetate, poly(hydroxy)ethylmethylmethacrylate, polyvinal pyrrolidone; polytetrafluoroethylene, cellulose esters, elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers, EVAL, poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydride, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinylidene halides (such as polyvinylidene fluoride and polyvinylidene chloride), polyvinyl ethers (such as polyvinyl methyl-ether), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as NYLON 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellulose nitrate, cellulose propionate, cellulose ethers, carboxymethyl cellulose, CELLOPHANE, PEG, PEG-acrylate or methacrylate, silk-elastin protein block-copolymer, and mixtures thereof.

In one embodiment, a device for insertion into a body is provided, comprising a biocompatible device with a porous surface having a tortuosity factor of greater than about 1.1, an average thickness of less than 10 microns and a peak-valley surface roughness of less than about 2 microns. In some embodiments, the porous surface has a tortuosity factor of greater than about 1.6. The device may also further comprising at least one therapeutic agent at least partially contained with the porous surface, and/or a means for controlling elution of the therapeutic agent from the porous surface.

In one embodiment, a method for treating a mammal is provided, comprising providing an implantable device comprising a porous surface with an outer surface, an interstitial space, a tortuosity factor of greater than about 1.1, an average thickness of less than 10 microns and a peak-valley surface roughness of less than about 2 microns; and implanting the implantable device into a location in the body. The location in the body may be a blood vessel, a portion of the gastrointestinal tract, a portion of the genitourinary tract, at least partially in a bone, at least partially subcutaneous, an airway, intramuscular, intraocular, intracranial or intrahepatic. The method may further comprise a therapeutic agent occupying at least a portion of the interstitial space, and also optionally eluting the therapeutic agent. The implantable device may further comprise a polymeric topcoat on outer surface of the porous surface, and sometimes a polymeric elution-rate controlling topcoat on outer surface of the porous surface. The implantable device of the method may further comprise a second therapeutic agent occupying at least a portion of the interstitial space.

In one embodiment, a method for treating a mammal is provided, comprising providing a nanoporous implantable device with a means for enhancing tissue healing; and implanting the implantable device into a space in the body.

In another embodiment, a method for treating a mammal is provided, comprising providing a nanoporous implantable device with a means for reduced mechanical slippage and friction with surrounding tissue; and implanting the implantable device into a location in the body.

In one embodiment, a polymer coated drug delivery stent is provided, comprising a tubular metal stent body; a porous layer on the body, wherein the pores of the porous layer have an angular component; a tie layer which is mechanically bonded to the porous layer; and a drug delivery layer bonded to the tie layer. The porous layer may be a nanoporous layer. In some embodiments, the average pore size is about 1 nanometer to about 1000 nanometers. The porous layer may be generally configured by the removal of at least one sacrificial material from a matrix comprising at least one sacrificial material with one or more structural materials that comprise the porous layer.

In one embodiment, a method of making a drug delivery stent is provided, comprising the steps of providing a stent having a porous surface, wherein the pores of the porous surface have an angular component; and applying a drug delivery layer to the porous surface under conditions which cause a portion of the drug delivery layer to advance into the porous surface to provide a bond between the porous surface and the drug delivery layer. The porous surface may be a nanoporous surface and/or may have an average pore size of about 1 nanometer to about 1000 nanometers. The porous surface may be generally configured by the removal of at least one sacrificial material from a matrix comprising at least one sacrificial material with one or more structural materials that comprise the porous surface.

In one embodiment, a method of making a drug delivery stent is provided, comprising the steps of providing a stent having a porous surface, wherein the pores of the porous surface have an angular component; bonding a tie layer to the porous surface; and bonding a drug delivery layer to the tie layer. The porous surface may be a nanoporous surface, and/or may have an average pore size of about 1 nanometer to about 1000 nanometers. The porous surface may be generally configured by the removal of at least one sacrificial material from a matrix comprising at least one sacrificial material with one or more structural materials that comprise the porous surface.

In one embodiment, a method of reducing the risk of delamination between a stent and a polymeric drug delivery layer during balloon expansion of the stent is provided, comprising the steps of providing the stent with a porous surface, wherein the pores of the porous surface have an angular component; and bonding the drug delivery layer to the porous surface. The porous surface may be a nanoporous surface, and/or may have an average pore size of about 1 nanometer to about 1000 nanometers. The porous surface may be generally configured by the removal of at least one sacrificial material from a matrix comprising at least one sacrificial material with one or more structural materials that comprise the porous surface. In some embodiments, drug delivery layer is bonded directly to the stent, or to a tie layer which is bonded to the stent.

In one embodiment, a method of reducing the risk of delamination between a stent and a polymeric drug delivery layer during balloon expansion of the stent is provided, comprising the steps of providing a stent having a drug delivery layer; radially dilating the stent; and retaining the drug delivery layer on the stent by a plurality of links between the drug delivery layer and pores in the stent; wherein the pores of the stent have an angular component. The pores may be nanopores. The pores may have an average pore size of about 1 nanometer to about 1000 nanometers. The pores may be generally configured by the removal of at least one sacrificial material from a matrix comprising at least one sacrificial material with one or more structural materials that comprise at least a portion of the stent.

In one embodiment, a method of bonding a polymer coating to a biomedical device with nanoporous layer is provided, comprising providing a polymeric coating material; selecting a solvent to dissolve a polymeric coating material for increased penetration/wicking of polymeric materials into a nanoporous coating; dissolving the polymeric coating material using the selected solvent; and applying the dissolved polymeric coating material to a nanoporous surface.

In one embodiment, a method of loading a porous medical device with a therapeutic agent is provided, comprising the steps of providing at least a component of a medical device having a porous zone, the porous zone comprising an interstitial structure, an interstitial space, an average depth and an average pore diameter; displacing any gaseous material within the interstitial space with a vapor form of a first solvent; and filling at least a portion of the interstitial space with at least one therapeutic agent. The filling step may be performed in a subatmospheric environment. The method may further comprise the step of preparing the interstitial space for filling with the therapeutic agent. The preparing step may comprise evacuating gaseous material from at least a portion of the interstitial space by exposing at least a portion of the interstitial space to subatmospheric pressure, applying an electrical charge to the interstitial structure, and/or exposing at least a portion of the interstitial space to a gaseous material. The first solvent may be ethanol, methanol, or other loading solvent that can be vaporized under conditions compatible with sufficient integrity/viability of the therapeutic agent. The method may further comprise the step of condensing the vapor form of the first solvent to a liquid form; and mixing the condensed liquid form of the first solvent with an exogenously applied liquid form of the first solvent. The therapeutic agent may comprise a therapeutic substance and a carrier. The filling step may be performed by use of sequential load-dry steps with supersaturated solutions of the therapeutic agent. The method may further comprise precipitating the therapeutic substance in the interstitial space. The precipitating step may be performed by removal of at least a portion of the carrier from the interstitial space. The method may also further comprise providing a polymeric coating material; dissolving the polymeric coating material using at least one solvent; applying the dissolved polymeric coating material to the porous zone; and penetrating the interstitial space of the porous zone with the dissolved polymeric coating material. The method may also further comprise filling at least 1% of interstitial space of the nanoporous layer. The filling may be at least 30% of interstitial space of the nanoporous layer, or at least 60% of interstitial space of the nanoporous layer. The penetrating of the interstitial space may occur to at least 1% of the average depth of the nanoporous layer, at least 30% of the average depth of the nanoporous layer, or at least 60% of the average depth of the nanoporous layer. The penetrating of the interstitial space may occur to a depth of at least about 5 times the average pore diameter of the nanoporous layer, at least about 10 times the average pore diameter of the nanoporous layer, at least about 50 times the average pore diameter of the nanoporous layer, or at least about 100 times the average pore diameter of the nanoporous layer. In some embodiments, the carrier comprises a second solvent. The second solvent may be miscible with the liquid form of the first solvent. The second solvent may be selected from a group comprising de-ionized water, ethanol, methanol, DMSO, acetone and chloroform. The second solvent may have a sufficient solubility product for the therapeutic agent but a vapor pressure less than water. The filling step may be performed at a vapor pressure generally between the vapor pressure of the first solvent but less than water. The method may further comprise exposing at least a portion of the interstitial space of the medical device to an aqueous solution with a low solubility product for the therapeutic agent. In some embodiments, the exposing step may be performed after the filling step. In still other embodiments, the method may further comprise the step of exposing the device to a below ambient pressure environment for the filling step. The below ambient pressure environment may be below about 760 torr, about 380 torr, about 190 torr, about 100 torr, about 60 torr, or about 30 torr. The method may further comprise the step of supercooling the environment to reduce the vapor pressure of the first solvent used for loading the therapeutic agent, exposing the device to an above ambient pressure environment for at least a portion of the filling step, and/or loading a propellant into the interstitial space. The loading step may be performed before the filling step. The method may further comprise the step of determining the amount of therapeutic agent filling the interstitial space, and/or changing the amount of therapeutic agent filling the interstitial space or on the surface of the nanoporous coating. The filling step may be performed at the point of use and/or at the point of manufacture.

In one embodiment, a method for providing a crystalline form of the one or more therapeutic agents within the nanoporous layer on a device is provided, comprising providing a device with a nanoporous layer; exposing the device to at least one vacuum-pressure cycle; filling at least a portion of the device with at least one supersaturated solution of a therapeutic agent; and applying at least one supercooled environment to the device.

In one embodiment, a method of loading a porous medical device with a therapeutic agent is provided, comprising providing at least a component of a medical device having a porous zone, the porous zone comprising an interstitial structure, an interstitial space, an average depth, an average pore diameter and at least one therapeutic agent within at least a portion of the interstitial space; providing a polymeric coating material; dissolving the polymeric coating material into an at least one solvent solution; applying the dissolved polymeric coating material to the porous zone; and penetrating the interstitial space of the porous zone with the dissolved polymeric coating material. The at least one therapeutic agent within the interstitial space may be selected from a group comprising: actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, GLEEVEC (imatinib mesylate), wortmannin, PDGF inhibitors, AG1295 (6,7-Dimethyl-2-phenylquinoxaline), rho kinase inhibitors, Y27632 ((+)-(R)-trans-4-(1-aminoethyl)N-(4-pyridyl)cyclohexanecarboxamide dihydrochloride), calcium channel blockers, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD34 antibodies, mycophenolic acid, Vitamin E, omega-3 fatty acids, tempamine, and docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radioisotope, a prodrug, antibody fragments, antibodies, live cells, therapeutic drug delivery microspheres or microbeads, gene therapy agents, viral vectors and plasmid DNA vectors. In another embodiment, the at least one therapeutic agent within the interstitial space of the porous zone may be selected from a group comprising: rapamycin, a rapamycin analog, paclitaxel, a paclitaxel analog, ABT-578, CCI-779, biolimus-A9, temsirolimus, other limus family member, macrocyclic lactones, cell cycle inhibitor that selectively inhibits the G1 phase of the cell cycle, mammalian inhibitor of rapamycin, or any agent that binds to FKBP12 and has similar pharmacological properties as rapamycin. In some embodiments, the at least one solvent used to dissolve the polymeric material may be selected from a group comprising: ethanol, methanol, acetone, chloroform, ethyl acetate, THF, benzyl alcohol, ethyl lactate, polyethyethylene glycol, propylene dlycol, dlycerin triacetin, diacetin, acetyl triethyl citrate, ethyl lactate N-methyl-2-pyrrolidinone, buyrolactone, dimethyl isosorbide, tryethylene glycol dimethyl ether, ethoxy diglycol, glycerol, glycerol formal, dimethyl formamide, dimethyl acetamide, dimethyl solfoxide, CHCL3, ketones, or alcohols. The dissolved polymeric coating material may have a concentration in the at least one solvent solution of about 0.1 to about 100%, or sometimes about 0.5 to about 3%. The dissolved polymeric coating material may have a concentration in the at least one solvent solution that causes drying of the polymer solvent solution prior to contact with the therapeutic agent-containing porous zone. The method may further comprise setting a distance between a deposition device used to apply the dissolved polymeric coating material and the porous zone at about 1 mm to about 20 cm, but sometimes between about 0.5 cm and about 5 cm. The method may also further comprise setting a flow rate for a deposition device used to apply the dissolved polymeric coating material to the porous zone between about 0.001 and 1.0 ml/min, or between about 0.010 and about 0.075 ml/min.

In one embodiment, a stent for insertion into a body structure is provided, comprising a tubular member having a first end and a second end, a lumen extending along a longitudinal axis between the first end and the second end, an ablumenal surface, a lumenal surface; and at least one porous layer, the porous layer comprising an interstitial structure and an interstitial space; wherein the interstitial space may be generally configured by the removal of at least a portion of at least one sacrificial material by a thermal dealloying process from a mixture comprising at least one sacrificial material with one or more structural materials that comprise the interstitial structure of the porous layer; and wherein the porous layer may be adapted to receive and release at least one therapeutic agent. In some embodiments, at least one sacrificial material may be selected for its boiling point and/or its vapor pressure. The thermal dealloying process may comprise the application of a heat source, a light source, a laser, an infrared light source, or an ultraviolet light source. The heat source may be an inductive heat source and/or an ultrasound source. In some embodiments, at least one sacrificial material comprises a form of magnesium. The application of a heat source may be performed in a vacuum of about $10^{-5}$ torr or less, or about $10^{-6}$ torr or less about $10^{-9}$ torr or less. The heat source may be capable of heating a portion of the mixture in a temperature of at least about 400° Celsius, about 500° Celsius, or about 600° Celsius. The pores of the porous layer may be modified by the application of an etchant to the porous layer. In some embodiments, the etchant may have anisotropic properties or isotropic properties.

In one embodiment, a erapy-eluting medical device is provided, comprising at least one component of a medical device having at least one therapy-eluting surface comprising an interstitial structure and an interstitial space, wherein the interstitial space may be configured generally by the removal of at least a portion of one sacrificial material by a thermal dealloying process from a mixture comprising at least one sacrificial material and one or more structural materials that comprise the interstitial structure of the porous layer; and wherein the therapy-eluting surface may be adapted to receive and release at least one therapeutic agent.

In another embodiment, a method for manufacturing a medical device with at least one non-polymeric porous layer is provided, comprising the steps of: providing at least a component of a medical device having at least one surface; depositing a layer of a material onto at least a portion of the surface; the layer of material comprising at least one sacrificial component and at least one structural component and at least one component may be not a polymer or therapeutic agent; and thermally removing at least a portion of at least one sacrificial component to form an interstitial space. The method may further comprise increasing the interstitial space with an etchant. The etchant may have isotropic properties or anisotropic properties. The thermally removing step may be performed in a vacuum. The thermally removing step may also be performed in using a laser.

In one embodiment, a stent for insertion into a body structure is provided, comprising a tubular member having a first end and a second end, a lumen extending along a longitudinal axis between the first end and the second end, an ablumenal surface, a lumenal surface; at least one porous layer, the porous layer comprising a surface, an interstitial structure and an interstitial space; and a polymeric coating bonded to at least a portion of the surface of the porous layer; wherein the interstitial space may be generally configured by the removal of at least one sacrificial material from a mixture comprising at least one sacrificial material with one or more structural materials that comprise the interstitial structure of the porous layer. The porous layer may further comprise at least one therapeutic agent within at least a portion of the interstitial space. The porous layer may be a metallic porous layer, a nanoporous layer, and/or have an angular component. The outer surface of the porous layer may have a peak-valley surface roughness of about 0.1 to about 3.0 µm. In some embodiments, the porous layer has a tortuosity factor of greater than about 1.1, or greater than about 1.6. The polymeric coating may be a drug eluting coating and/or an elution rate-controlling coating. The porous layer may further comprise at least one therapeutic agent within at least a portion of the interstitial space. The therapeutic agents within at least a portion of the interstitial space may be selected from a group comprising: actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, GLEEVEC (imatinib mesylate), wortmannin, PDGF inhibitors, AG1295 (6,7-Dimethyl-2-phenylquinoxaline), rho kinase inhibitors, Y27632 ((+)-(R)-trans-4-(1-aminoethyl)-N-(4-pyridyl)cyclohexanecarboxamide dihydrochloride), calcium channel blockers, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD 34 antibodies, mycophenolic acid, Vitamin E, omega-3 fatty acids, tempamine, and docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radio-isotope, a prodrug, antibody fragments, antibodies, live cells, therapeutic drug delivery microspheres or microbeads, gene therapy agents, viral vectors and plasmid DNA vectors. In some embodiments, the therapeutic agents within at least a portion of the interstitial space may be selected from a group comprising: rapamycin, a rapamycin analog, paclitaxel, a paclitaxel analog, ABT-578, CCI-779, biolimus-A9, or temsirolimus. The porous layer may have an average thickness of about 5 nm to about 10 microns. The porous layer may have average pore size of about 0.1 nanometers to about 10 microns, or about 0.1 nm to about 500 nm, or sometimes about 1 nm to about 50 nm. In some embodiments, the polymeric coating comprises a material selected from a group consisting of: polyurethanes, silicones, polyesters, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as NYLON 66 and polycaprolactone, alkyd resins, polycarbonates, polyoxymethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Other coating materials may include lactone-based copolyesters, polyanhydrides, polyaminoacids, polysaccharides, polyphosphazenes, poly(ether-ester) copolymers, and blends of such polymers, poly(ethylene)vinylacetate, poly(hydroxy)ethylmethylmethacrylate, polyvinal pyrrolidone; polytetrafluoroethylene, cellulose esters, elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers, EVAL, poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydride, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinylidene halides (such as polyvinylidene fluoride and polyvinylidene chloride), polyvinyl ethers (such as polyvinyl methyl-ether), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as NYLON 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellulose nitrate, cellulose propionate, cellulose ethers, carboxymethyl cellulose, CELLOPHANE, PEG, PEG-acrylate or methacrylate, silk-elastin protein block-copolymer, and mixtures thereof.

In one embodiment, a stent for insertion into a body structure is provided, comprising a tubular member having a first end and a second end, a lumen extending along a longitudinal axis between the first end and the second end, an ablumenal surface, an lumenal surface; at least one porous layer, the porous layer comprising a surface, an interstitial structure and an interstitial space; and a means for therapeutic agent elution control; wherein the interstitial space may be generally configured by the removal of at least one sacrificial material from a mixture comprising at least one sacrificial material with one or more structural materials that comprise the interstitial structure of the porous layer.

In another embodiment, a therapy-eluting medical device is provided, comprising at least one component of a medical device having at least one porous coating interface comprising an interstitial structure and an interstitial space, wherein the interstitial structure may be configured generally by the removal of at least a portion of one sacrificial material from a mixture comprising at least one sacrificial material and one or more structural materials that comprise the interstitial structure of the porous coating interface; and a polymeric coating bonded to at least a portion of the porous coating interface. The polymeric coating may be a drug-eluting coating and/or an elution rate controlling coating. The porous coating interface may further comprise at least one therapeutic agent.

The above embodiments and methods of use are explained in more detail below.

DETAILED DESCRIPTION OF THE PREFERRED EMBODIMENT

Figure 1:
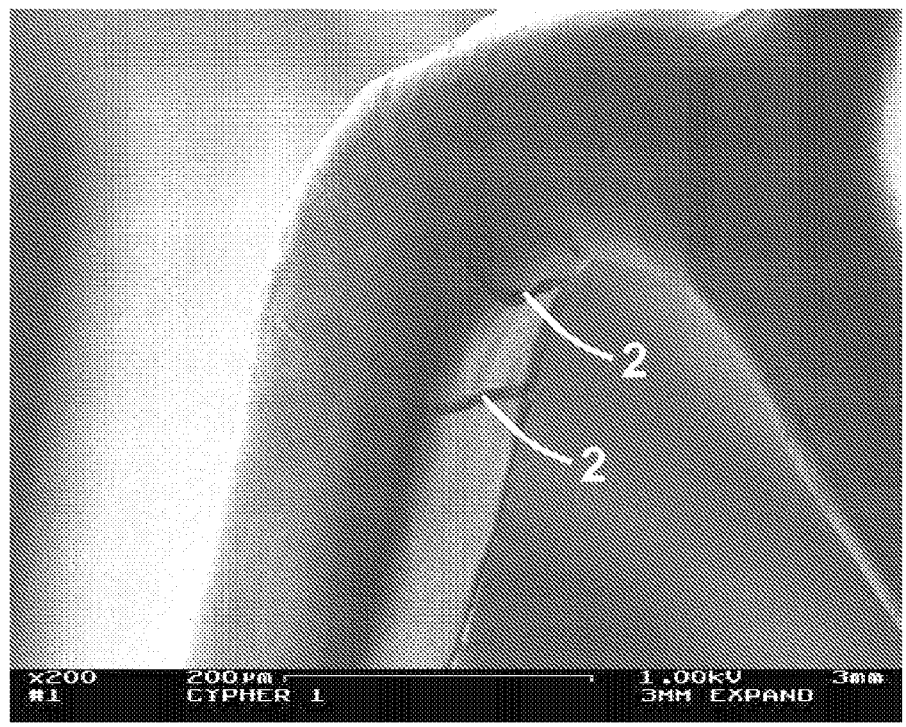
FIG. 1 is an electron micrograph of a polymeric drug-elution coating following expansion of a prior art device.
Figure 2:
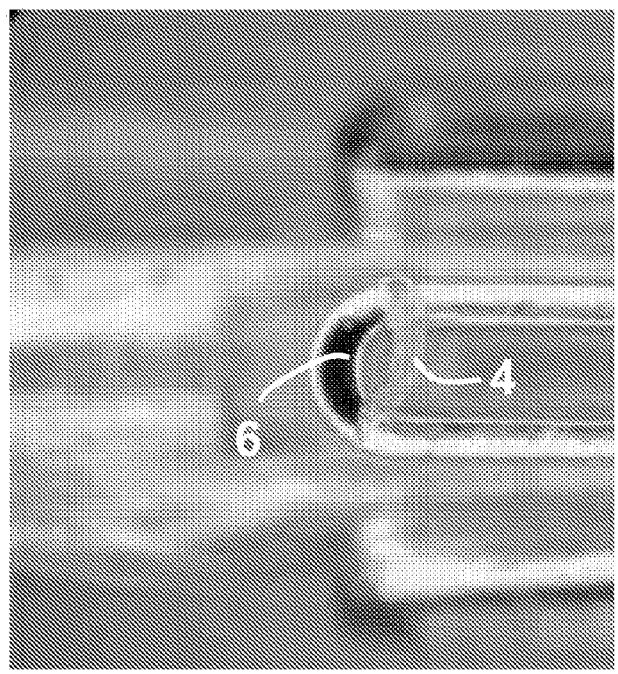
FIG. 2 is another electron micrograph of a polymeric drug-elution coating of a prior art device.

The materials typically applied as coatings to medical implants, such as hydroxyapatites, porous alumina, sintered metal powders and polymeric materials such as poly(ethylene glycol)/poly(L-lactic acid) (PLGA), have limitations related to coating adhesion, mechanical properties, and material biocompatibility. The structural integrity of existing coatings may be compromised during the use of the device. For example, radial expansion of a coronary stent may substantially disrupt the polymeric coating during deformation of the stent structure. FIG. 1 depicts cracks 2 in the polymeric coating of a stent following balloon expansion. Polymeric coatings may also exhibit poor adhesion to a device even before expansion. FIG. 2 illustrates a separation of the polymeric coating 4 from the stent structure 6 after removal from its package. In both cases, there were no unusual circumstances which would predispose the polymeric coatings to crack or separate. One embodiment of the current invention is to utilize the nanoporous coating as a means to improve adhesion of these sorts of polymer coatings to the stent surface. Applications of these coatings also introduce additional complexity to the fabrication process, increasing overall production costs.

Therefore, it would be advantageous to have improved implantable medical devices with porous layers capable of absorbing and eluting therapeutic agents and methods for fabricating those devices. Such methods would ideally produce a more adherent and mechanically robust porous layer while simplifying device manufacture and loading of therapeutic agents. Methods would also ideally provide porous layers having desired pore sizes and densities. These methods would also allow for controlled and programmable release of therapeutic agents into bodily tissues. At least some of these objectives will be met by the present invention.

A. Dealloying Process

Methods of the present invention provide means for fabricating an implantable medical device having at least one porous layer or zone. The pores may be nanopores. Generally, the methods involve providing an implantable medical device containing an alloy and removing at least one component of the alloy to form the porous layer. In some embodiments, an alloy may first be deposited on an implantable device and one or more components of the alloy may then be removed to form the porous layer. Such methods are often referred to as "dealloying." For a general description of dealloying methods, reference may be made to "Evolution of nanoporosity in dealloying," Jonah Erlebacher et al., Nature 410, pp. 450-453, March 2001, the entire contents of which are hereby incorporated by reference. Dealloying a layer of an implantable device provides a porous layer, which may then be infused with one or more therapeutic agents for providing delivery of an agent into a patient via the device. Use of dealloying methods will typically provide more adherent and mechanically robust porous layers on medical implantables than are currently available, while also simplifying device manufacture. Such layers may also facilitate the process of optimizing loading and delivery of one or more therapeutic agents.

Although the following description often focuses on the example of implantable stent devices for use in PTCA procedures, any suitable implantable medical device may be fabricated with methods of the invention. Other devices may include, but are not limited to, other stents, stent grafts, implantable leads, infusion pumps, vascular coils for treating aneurysms including neural coils, vascular access devices such as implantable ports, orthopedic screws, rods, plates and other implants, implantable electrodes, subcutaneous drug-elution implants, and the like. Similarly, devices fabricated via methods of the present invention may be used to deliver any suitable therapy or combination of therapies in a patient care context, veterinary context, research setting or the like. Therapeutic agents may include, for example, drugs, genes, anti-restenosis agents, anti-thrombogenic agents, antibiotic agents, anti-clotting agents, anti-inflammatory agents, cancer therapy agents, gene therapy agents, viral vectors, plasmid DNA vectors and/or the like. In other embodiments, the porous layer may be configured to hold live cells capable of secreting therapeutic materials, including but not limited to proteins, hormones, antibodies, and cellular signaling substances. Other materials for supporting the function of the live cells may also be inserted into the porous layer, including but not limited to glucose, hormones and other substances that act therapeutically upon the live cells. More than one live cell type may be included in the porous layer. The nanoporous coating may also be used as an absorption layer to remove materials from body fluids either alone or in combination with materials placed within the coating that augment this process. These materials may include but are not limited to special chemicals including but not limited to chelating agents such as penicillamine, triethylene tetramine dihydrochloride, EDTA, DMSA (succimer) and deferoxamine mesylate, chemical modification of the coating surface, antibodies, and microbeads or other materials containing cross linked reagents for absorption of drugs, toxins or other agents. Thus, the following description of specific embodiments is provided for exemplary purposes only and should not be interpreted to limit the scope of the invention as set forth in the appended claims.

Methods of the present invention provide a means for fabricating an implantable medical device having at least one porous layer. In one embodiment, a method of fabricating an implantable device having a porous layer for storage and controlled release of at least one therapeutic agent is provided. This process may include providing an implantable medical device comprising at least one alloy and removing at least one component of the alloy to form the porous layer. In some embodiments, the component is removed to form the porous layer, leaving a biocompatible material, such as gold. In some embodiments, the medical device comprises a tubular stent device having an outer surface and an inner surface. For example, the stent device may comprise a coronary artery stent for use in a percutaneous transluminal coronary angioplasty (PTCA) procedure. In some of these embodiments, the alloy is disposed along the outer surface of the stent or other biomedical device including orthopedic implants, surgical screws, coils, and suture wire just to name a few.

In another embodiment, a method of fabricating an implantable device having a porous layer for storage and controlled release of at least one therapeutic agent includes providing an implantable medical device comprising a matrix of two or more components and removing at least one component of the matrix to form the porous layer. In some embodiments, the component is removed to form the porous layer, leaving a biocompatible material.

Optionally, providing the implantable medical device may also include depositing the alloy on at least one surface of the medical device. In various embodiments, the alloy may be disposed along an outer surface of the implantable medical device, such that a dissolving step forms the porous layer on the outer surface of the device. In some embodiments, the alloy includes one or more metals, such as but not limited to gold, silver, nitinol, steel, chromium, iron, nickel, copper, aluminum, titanium, tantalum, cobalt, tungsten, palladium, vanadium, platinum, stainless steel, cobalt chromium, and/or niobium. In other embodiments, the alloy comprises at least one metal and at least one non-metal. Optionally, before the dissolving step at least one substance may be embedded within the alloy. For example, a salt or an oxide particle may be embedded in the alloy to enhance pore formation upon dissolution.

Dissolving one or more components of the alloy may involve exposing the alloy to a dissolving substance. For example, a stainless steel alloy may be exposed to sodium hydroxide in one embodiment. Typically, one or more of the most electrochemically active components of the alloy are dissolved. After the dissolving step, additional processing may be performed. For example, the device may be coated after the dissolving step with titanium, gold and/or platinum. Some further embodiments include introducing at least one therapeutic agent into the porous layer. For example, the therapeutic agent may be introduced by liquid immersion, vacuum desiccation, high pressure infusion or vapor loading in various embodiments. The therapeutic agent may be any suitable agent or combination of agents, such as but not limited to anti-restenotic agent(s) or anti inflammatory agent(s), such as Rapamycin (also known as Sirolimus), Taxol, Prednisone, and/or the like. In other embodiments, live cells may be encapsulated by the porous layer, thereby allowing transport of selected molecules, such as oxygen, glucose, or insulin, to and from the cells, while shielding the cells from the immune system of the patient. Some embodiments may optionally include multiple porous layers having various porosities and atomic compositions.

In another embodiment, a method for treating a blood vessel using an implantable medical device having a porous layer with controlled release of at least one therapeutic agent is provided. This process includes providing at least one implantable device having a porous layer containing at least one therapeutic agent; and placing the device within the blood vessel at a desired location, wherein the device controllably releases at least one therapeutic agent from the porous layer after placement. For example, in one embodiment the desired location may comprise an area of stenosis in the blood vessel, and at least one therapeutic agent released from a stent may inhibit re-stenosis of the blood vessel. Again, the therapeutic agent in some embodiments may be one or more anti-restenosis agents, anti-inflammatory agents, or a combination of both. In one embodiment, the blood vessel may be a coronary artery. In such embodiments, the placing step may involve placing the stent so as to generally contact the porous layer with at least one treatment site such as a stenotic plaque, vulnerable plaque or angioplasty site in the blood vessel and/or an inner wall of the blood vessel.

In still another embodiment, an implantable medical device has at least one porous layer comprising at least one remaining alloy component and interstitial spaces, wherein the interstitial spaces comprise at least one removed alloy component space of an alloy, the alloy comprising the at least one remaining alloy component and at least one removed alloy component. Also in some embodiments, the implantable medical device comprises an implantable stent device having an outer surface and an inner surface, and the porous layer is disposed along the outer surface. For example, the stent device may comprise a coronary artery stent for use in a percutaneous transluminal coronary angioplasty procedure. As described above, the alloy may comprise one or more metals selected from the group consisting of gold, silver, nitinol, steel, chromium, iron, nickel, copper, aluminum, titanium, tantalum; cobalt, tungsten, palladium, vanadium, platinum and/or niobium. For example, the alloy may comprise stainless steel and the porous layer may comprise iron and nickel.

In some embodiments, one or more components that are dissolved comprise the most electrochemically active components of the alloy. Generally, the device further includes at least one therapeutic agent disposed within the at least one porous layer. Any such agent or combination of agents is contemplated. Finally, the device may include a titanium or platinum coating over an outer surface of the device.

In one embodiment of the invention, the device contains an initial metallic porous layer The porous layer may promote adhesion of a second porous layer comprising a polymer or other material for storage and timed release of one or more therapeutic substances, and may also serve as a second reservoir for that or additional therapeutic agents. That is, one might load one therapeutic agent in the initial porous coating, and a second therapeutic agent in the second porous layer. This capability is unique, in that a major limitation of current porous materials, including polymers used in drug delivery stents such as the Cypher® and Taxus®, is the inability to deliver more than one therapeutic agent. One embodiment of the invention comprises a stent with a metallic nanoporous coating with a releasable first therapeutic agent placed in the nanoporous coating. A polymeric matrix containing a releasable second therapeutic agent is bonded or adhered to the metallic nanoporous coating. The first therapeutic agent and second therapeutic agent may be the same or different. In this embodiment, the metallic nanoporous coating serves to store and release therapeutic agents and to provide an improved bonding surface for a drug eluting coating.

In another embodiment of the invention comprises providing a metallic nanoporous coating, loading a first therapeutic agent into the coating and applying a polymer matrix containing the same or other different therapeutic agent using dip coating or spray coating methods currently in commercial use. In this manner, one could achieve loading and controlled release of multiple therapeutic agents including those that have similar or very different physical characteristics including but not limited to size, hydrophobicity, hydrophilicity, solubility, heat sensitivities, and chemical sensitivities.

B. Example: a Nanoporous Coronary Stent

Figure 3:
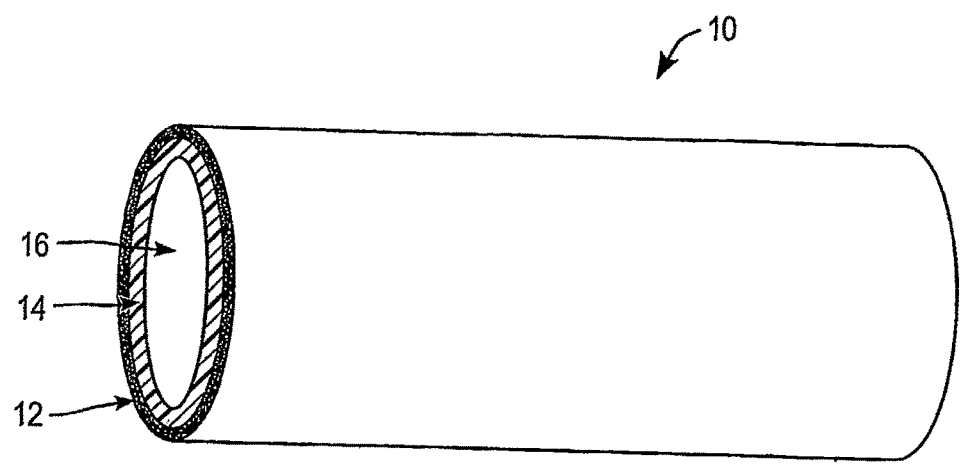
FIG. 3 is a perspective schematic view of an implantable stent device having a porous layer on the ablumenal surface according to one embodiment of the present invention.

Referring now to FIG. 3, an implantable medical device fabricated by methods of the present invention may include an elongate tubular stent device 10, having two or more layers 12, 14 and a lumen 16. In one embodiment, stent device 10 includes an outer (abluminal) porous layer 12 and an inner (lumenal) non-porous layer 14. Other embodiments may suitably include an inner porous layer 12 and an outer non-porous layer 14, multiple porous layers 12, multiple non-porous layers 14, a porous coating over an entire surface of a medical device, or any combination of porous and non-porous surfaces, layers, areas or the like to provide a desired effect. In one embodiment, for example, multiple porous layers may be layered over one another, with each layer having a different porosity and optimally a different atomic composition. Porous layer 12 and non-porous layer 14 may have any suitable thicknesses in various embodiments. In some embodiments, for example, a very thin porous layer 12 may be desired, such as for delivery of a comparatively small amount of therapeutic agent. In another embodiment, a thicker porous layer 12 may be used for delivery of a larger quantity of therapeutic agent and/or for a longer duration of agent delivery. Any suitable combination and configuration of porous layer 12 and non-porous layer 14 is contemplated. In one embodiment, porous layer 12 may comprise the entire thickness of stent device 10, so that the device is completely porous. Again, stent device 10 is only one example of a device with which porous layers may be used. Other devices may not have a lumen, for example, but may still be suitable for use in the present invention. For example, the porous layer may be provided on the threaded surface of a bone screw, with the pore size optimized to facilitate cortical or cancellous bone ingrowth.

Figure 4A:
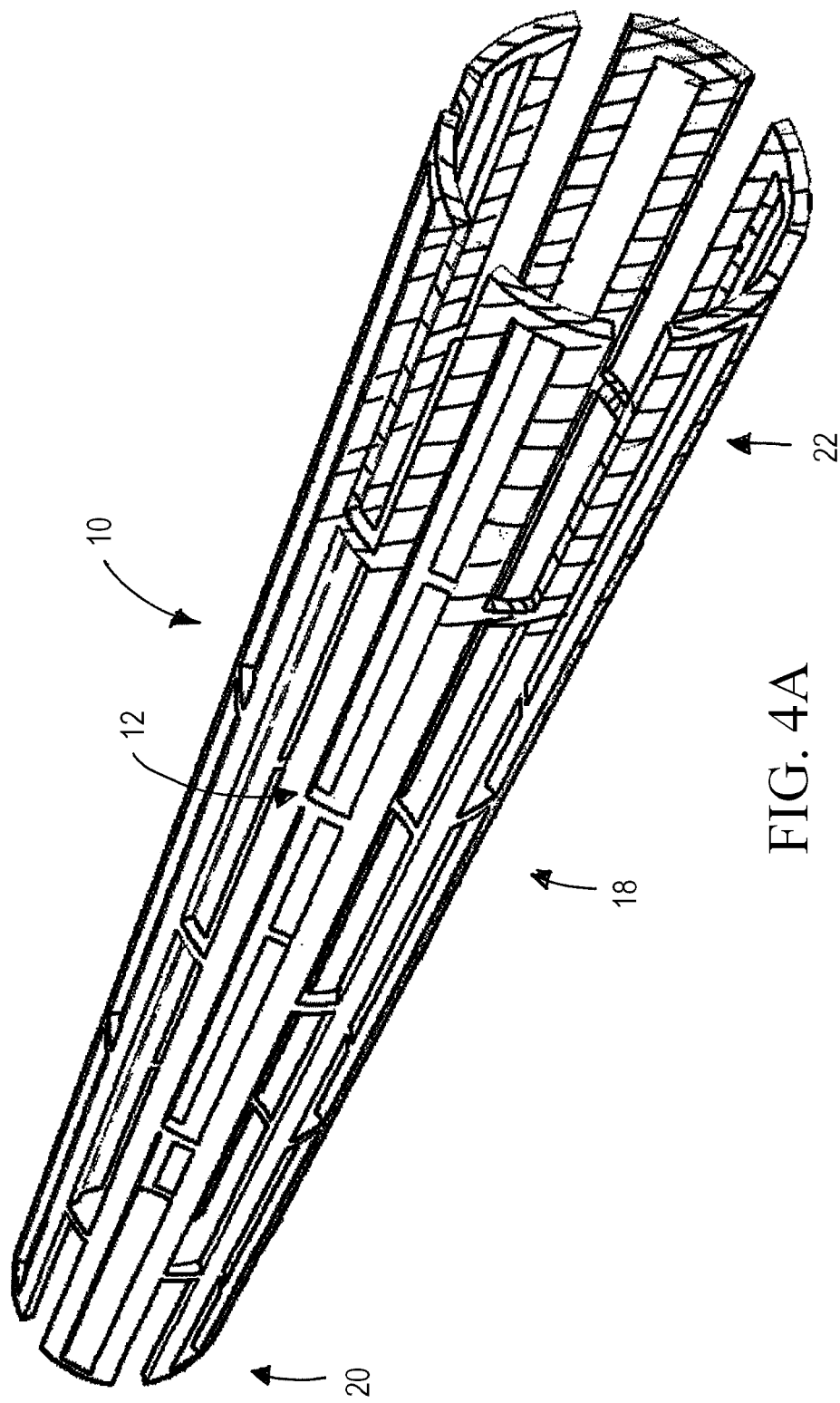
FIG. 4A is a perspective view of an implantable stent device having a porous layer with varying structure along the longitudinal axis.
Figure 4B:
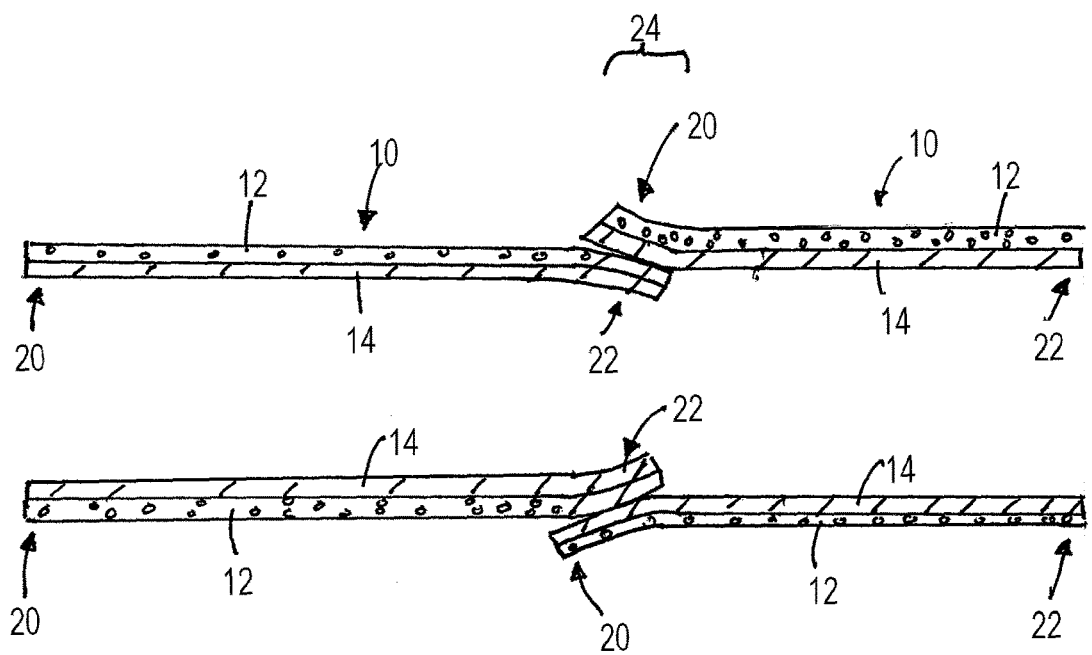
FIG. 4B is an axial cross sectional view of two overlapping stents.

The porous layer may be configured with nonuniform properties across portions of the porous layer. For example, in a coronary stent device, the porous layer may be configured to hold increased or decreased amounts of therapeutic agents at the ends of the stent, as compared to the central portion. In procedures utilizing multiple drug eluting stents, for example in treating coronary lesions longer than can be covered with a single stent, the multiples stents are often positioned to overlap each other at the ends (so called "kissing stents"). The overlap results in higher amounts of therapeutic agent being eluted into the vessel proximal to the overlap region. In this embodiment of the invention, shown in FIGS. 4A and 4B, the properties of the porous layer 12 are generally different at the central region 18 compared to at least one of the end regions 20, 22 so that uniform drug elution is maintained across the overlap region 24.

The properties of the porous layer which influence the elution of the therapeutic agent include layer thickness, porosity, and tortuosity of the pores, which may be influenced by the manufacturing technique and by coating composition.

In one embodiment, variations in these properties are achieved using masking processes which result in selective deposition of porous layers with different properties along the length of the device. Such masking processes are well known to those skilled in the art of film deposition. In another embodiment, the variation in properties is achieved by using a layer deposition process which is inherently nonuniform. One non-limiting example is a thin film sputtering process with a highly nonuniform sputter yield as a function of deposition angle. These processes are well known to those skilled in the art of film deposition.

Figure 5:
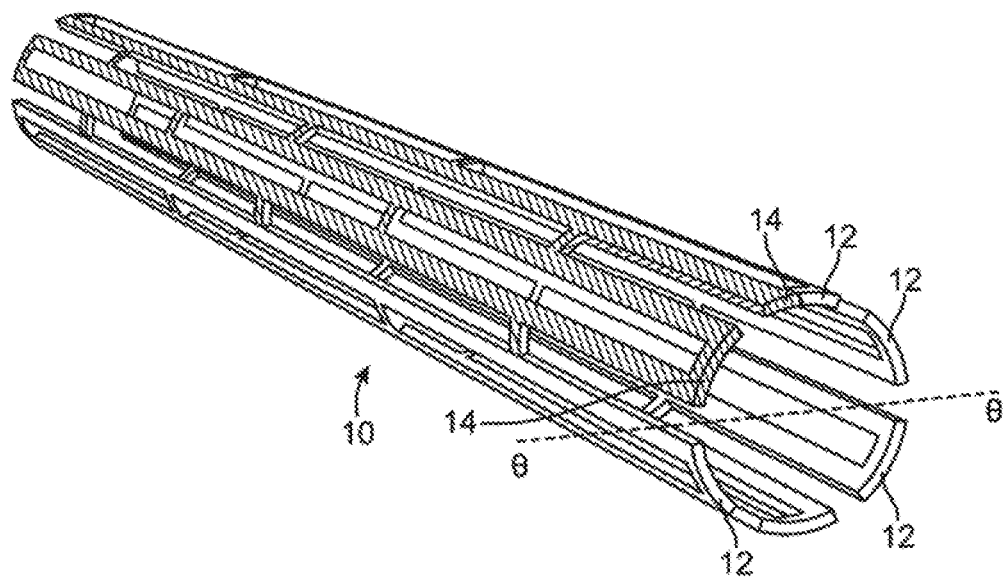
FIGS. 5 and 6 are perspective and cross sectional views of an implantable stent device having a porous layer with varying circumferential structure.
Figure 6:
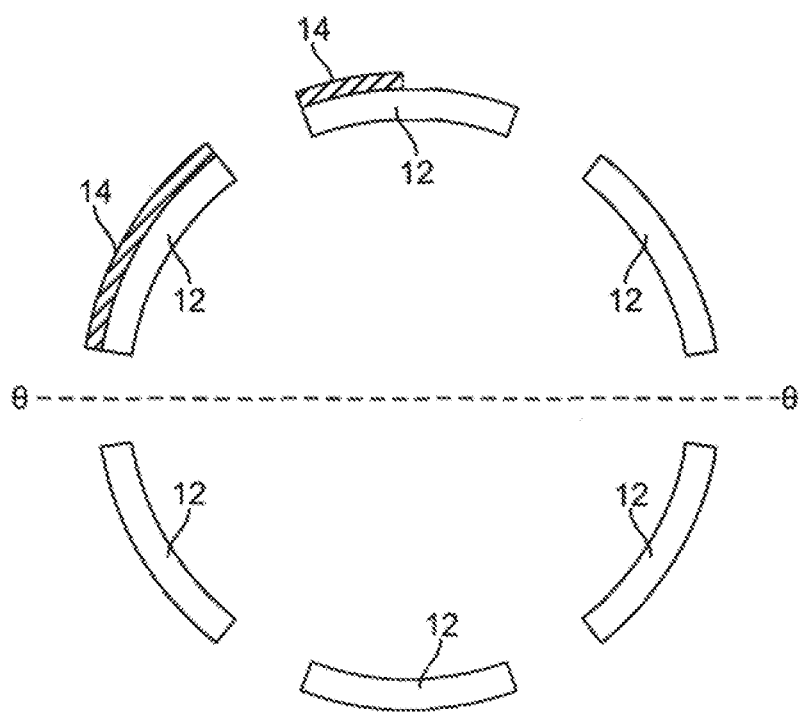

Similarly, in a coronary stent device, the porous layer may be provided with different properties around the circumference of the stent or portions thereof. FIGS. 5 and 6 are perspective and cross sectional views of an implantable stent device having a porous layer 12 with varying circumferential structures. For example, a device may have a porous layer with one set of properties around three-quarters (270 degrees) of the circumferential area, and a porous layer with another set of properties around the remaining one-quarter (90 degrees) of the circumferential area. In other words, the porous layer properties have a functional dependence on the azimuthal angular position denoted as angle theta in FIGS. 5 and 6. This embodiment would be useful for treating vessel lesions which have a corresponding angular nonuniformity, for example vessels with an asymmetric atheromatous cap. In this case it would be advantageous to provide increased delivery of therapeutic agents in the thicker region, and decreased delivery elsewhere. The properties which affect elution characteristics may be varied to control the total dose of the therapeutic agent delivered, or the delivery rate, or other pharmacologically relevant parameters. In one embodiment, variations in these properties are achieved using masking processes which result in selective deposition of porous layers with different properties circumferentially around the device. Such masking processes are well known to those skilled in the art of film deposition. In another embodiment, the variation in properties is achieved by using a layer deposition process which is inherently nonuniform; for example a thin film sputtering process with a highly nonuniform sputter yield as a function of deposition angle is inherently non-uniform. These processes are well known to those skilled in the art of film deposition.

C. Pore Layer Characteristics and Features

The properties of the porous layer can be varied over large ranges. For example, the porous layer thickness may range from about 5 nanometers to about 500 micrometers or more. In other embodiments, the porous layer thickness is preferably about 100 nm to about 500 µm, and in other embodiments, about 50 nm to about 10 µm. Methods for controlling the porous layer thickness are well known to those skilled in the art of film deposition. In one embodiment, the porous layer thickness is controlled by limiting the time period over which a thin film is sputtered onto the device. Pore sizes may range from about 5 nanometers up to nearly the thickness of the film. Preferably, the pore sizes range from about 5 nanometers to about 1,000 nanometers. In other embodiments, the pore size may be in the range of about 0.1 nm to about 500 nm or more, sometimes from about 20 nm to about 200 nm, or from about 80 nm to about 500 nm, and at other times about 1 nm to about 50 nm. Control of the pore sizes may be adjusted by controlling the amount of the sacrificial material incorporated into the layer. In one embodiment, this control is achieved by adjusting the relative rates of sputter deposition of the porous layer material and the sacrificial material. The distribution of pore sizes may also vary. In one embodiment, this control is achieved by utilizing multiple sacrificial materials, for example, copper, silver, and/or aluminum. The average porosity of the porous layer can be characterized by a void fraction, defined as the fraction of open volume occupied by the pores. Porous layers with higher void fractions can deliver larger amounts of therapeutic agents for the same thickness. Preferably, the void fraction is between about 10% to about 80%. In some embodiments, the void fraction is preferably within the range of about 20% to about 60%. The void fraction may also vary across different portions of the porous layer. These features of the porous layer may be measured using any of a variety of pore analysis products, such as those manufactured by Porous Materials, Inc. (Ithaca, N.Y.).

In one embodiment, different drugs, different volume of drugs, or different drug activities or concentrations may be loaded in different regions of the stent or biomedical device by use of unique vacuum dip loading procedures described in greater detail later in this application. For example, one could use masking techniques to selectively load the middle region versus the end regions of a stent with different therapeutic agents. In addition, one can exploit the differential solubility properties of therapeutic agents in solvents in conjunction with different viscosities and wetting properties to selectively load drugs on the inside versus outside layers of the coating. For example, one could load a hydrophobic drug like rapamycin deep into the coating using a solvent like ethanol that has high rapamycin solubility, but very low viscosity. This process could then be followed by loading a hydrophilic drug in water solvent on the surface (the water solvent will not dissolve the rapamycin deeper in the coating), and/or using a second hydrophobic drug in a viscous solvent like benzyl alcohol that only "wets" the upper layers of the coating. In some embodiments of the invention, one or more therapeutic agents may also be applied onto the surface of the stent or biomedical device, in addition to any therapeutic agents loaded within the porous layer of the stent or biomedical device. The surface therapeutic agent may be applied by dip coating or spray coating. The therapeutic agent may be applied in a solvent carrier, which is then evaporated from the surface to concentrate and/or adhere the therapeutic agent to the device surface. The therapeutic agent may also applied to the surface of the device in a polymeric carrier. In short, there are a large number of unique combinations of loading solvents and procedures that can be used to control loading of multiple therapeutic substances into the nanoporous coating or programmable elution surface (PES).

As mentioned above, any medical device may be fabricated with one or more porous layers 12 according to embodiments of the present invention. Where the device is an implantable stent device 10, any suitable type, size and configuration of stent device may be fabricated with one or more porous layers 12. In one embodiment, stent device 10 comprises an expandable stent for implantation in a coronary artery during a PTCA procedure. Such a stent device 10 may be fabricated from any suitable material or combination of materials. Referring back to FIG. 3, in one embodiment, stent device 10 comprises a stainless steel non-porous layer 14 and an iron and nickel porous layer 12. In some embodiments, porous layer 12 may be formed of a biocompatible material, such as gold. In other embodiments, porous layer 12 may be formed from a cobalt chromium alloy such as L605. Any other suitable material or combination of materials is contemplated. Furthermore, stent device 10 may include a layer or coating comprising a biocompatible material such as titanium, gold or platinum, which may provide biocompatibility, corrosion resistance or both.

Multiple porous layers containing therapeutic agents may be fabricated. The layers may have the same or different compositions and properties, and may contain the same or different drugs. In one embodiment, the loading of a therapeutic agent into a layer is performed before the fabrication of subsequent layers. This is accomplished by fabricating a porous layer according the methods already described, and then loading this layer with a therapeutic agent. This is followed by a step to remove excess therapeutic agent which could compromise the adhesion or integrity of subsequent porous layers. Preferably, this step consists of an oxygen plasma or backsputter etching step. Deposition and loading of subsequent layers is repeated until the final structure is obtained.

In one embodiment, a coronary stent is configured with a first porous layer containing an antirestenotic agent, and a second porous layer containing an antithrombotic agent. When the device is deployed, the elution of the therapeutic agents proceeds in reverse order. Thus the antithrombotic agent, which is needed shortly after the device deployment, is eluted first. The antirestenotic agent is then eluted over a longer time period.

The porous layers may be fabricated with varying properties through their cross section. Preferably, this is done by using different amounts of the sacrificial material at different stages of the deposition of the composite matrix. In one embodiment, a larger amount of sacrificial material is used at the early stages, while a smaller amount is used towards the end of the matrix deposition. After the sacrificial etch processing, the porosity of the top of the film is less than that of the bottom. This allows a larger amount of therapeutic agent to be loaded into a given thickness of a porous layer, while retaining the slow elution characteristics of a small pore size.

In another embodiment, the pore size is varied such that a region of small pores is sandwiched between regions with large pores. This permits the device to have both rapid short term elution of a therapeutic agent, which elutes from the top region with large pores, and a longer, slow elution of a therapeutic agent whose rate is controlled by transport of the agent from the lower region of large pores by the intermediate region of small pores.

In another embodiment, a medical device such as a vascular stent incorporates porous layers with different properties on the inner and outer surfaces. The layers may be fabricated sequentially. For example the inner layer is deposited after coating the outside surface with a masking material which prevents the porous layer from adhering to the outside surface. Preferably, this masking material is photoresistant. After the inner surface is coated with the porous layer, the outer surface of the device is coated with a porous layer with different characteristics using the same technique. The different coatings permit the delivery of therapeutic agents with controlled rates and doses. In another embodiment, a vascular stent with a coating on the outside surface permits elution of an antirestenotic agent over a short period of time, preferably one week to one month, while the coating on the inner surface permits elution of an antirestenotic agent over a longer period of time, preferably one month or longer.

In yet another embodiment, a medical device such as a vascular stent incorporates porous layers with the same or different properties on the inner and outer device surfaces. The inner and outer surfaces are then loaded with different therapeutic agents. For example, an antithrombotic agent such as Plavix or heparin may be loaded on the inner (lumenal) surface, and an antirestenotic agent such as rapamycin or taxol may be loaded on the outer (ablumenal) surface. When deployed, the antirestenotic agent is eluted largely towards the vessel wall. The antithrombotic agent loaded into the porous layer on the inner surface of the device, which is in proximity to the blood flow, elutes towards the flow and reduces the risk of thrombotic events. Loading of different therapeutic agents onto the inner and outer surfaces is accomplished by sequential loading of each surface while the other surface is masked.

The deposition of a matrix containing the porous layer material and a sacrificial material can be accomplished by any of several techniques which result in robust layers exhibiting good adhesion to the medical device. Preferably, this deposition is accomplished by thin film sputtering techniques. Other methods for forming the matrix include thermal evaporation, electron-beam evaporation, high pressure sputtering, high pressure evaporation, directed vapor deposition, electroplating, laser ablation, bead sintering methods, sol-gel processing, aerosol processing, and combinations of these methods. These methods for film deposition are well known to those skilled in the art of many disparate fields, including microelectronics fabrication, thermal barrier coating technology, and compact disc manufacturing. Descriptions of these processes can be found in standard texts, for example "Thin Film Processes" by John L. Vossen and Werner Kern; "Silicon VLSI Technology: Fundamentals, Practice, and Modeling" by James D. Plummer, Michael D. Deal, and Peter B. Griffin; "Silicon Processing for the VLSI Era" by Stanley Wolf and Richard N. Tauber.

In one embodiment, the deposited matrix includes at least one ferromagnetic material and least one nonferromagnetic material. Preferably the ferromagnetic material is nickel. This matrix deposition is preferably performed using a thin film sputtering technique. The microscopic or nanoscopic orientation of the ferromagnetic species is controlled by immersing the medical device in a magnetic field. Preferably, this magnetic field is generated by an electromagnet. Increasing the magnetic field intensity will cause a corresponding variation in the agglomeration of the ferromagnetic material. Preferably the ferromagnetic material is the sacrificial component of the matrix. Subsequent etching of the sacrificial material from the matrix will form a porous layer whose characteristics are controlled by the intensity and direction of the magnetic field.

In one embodiment, the magnetic field is oriented parallel to the direction of growth of the matrix material. The agglomeration of the sacrificial ferromagnetic material at the microscale or nanoscale causes the pores in the porous layer to be largely oriented normal to the direction of growth. In another embodiment, the magnetic field is oriented perpendicular to the direction of growth of the matrix material. The agglomeration of the sacrificial ferromagnetic material at the microscale or nanoscale causes the pores in the porous layer to be largely oriented perpendicular to the direction of growth. Elution of the therapeutic agent can be alternatively increased or decreased by using these embodiments. In yet another embodiment, the direction of the magnetic field is varied from parallel to perpendicular at least one time during the growth of the matrix. The agglomeration of the sacrificial ferromagnetic material at the microscale or nanoscale causes the pores in the porous layer to be related to the variation in magnetic field, which affords an additional method for controlling the elution rate of the therapeutic material.

The porous layer may have uniform or nonuniform characteristics at the mesoscale. In this context, mesoscale is understood to be a characteristic length several times that of the largest pores in the film. Preferably, the mesoscale is about ten times the size of the largest pores. Nonuniform characteristics of a porous layer would comprise layers with variations of pore size or density at the mesoscale. Preferably, the variation in pore sizes or density would be from one-tenth to unity times the size or density of the largest pores. This nonuniformity will result in corresponding variations of the elution rate of the therapeutic agent or agents. For example, a porous layer comprising pores with size distributions centered around about 50 nm and about 500 nm will have elution characteristics combining those of separate porous layers with the corresponding pore sizes.

In one embodiment, this distribution of pore sizes is fabricated by incorporating multiple sacrificial materials into the matrix. Preferably, the matrix is formed by thin film sputtering techniques. Preferably, the sacrificial materials are silver and aluminum. In another embodiment, the distribution of pore sizes is accomplished by phase segregation of the matrix material. Preferably, the matrix material is a Cu/Pt alloy (75/25%) which results in a higher density of pores in the grain boundaries between the Pt grains after dealloying, as described in "Formation of nanoporous platinum Cu from Cu0.75Pt0.25" by D. V. Pugh, A. Dursun, and S. G. Corcoran, J. Mater. Res., Vol. 18, No. 1, January 2003, pp. 216-221.

Figure 7A:
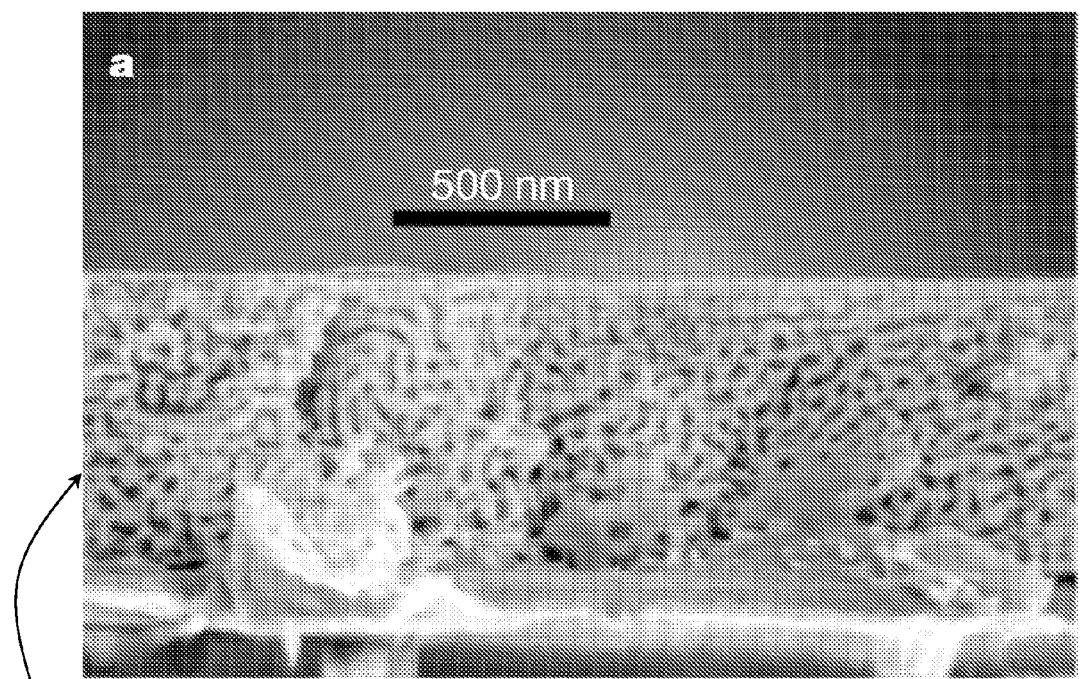
FIGS. 7A-7B are electron micrographs of a porous layer formed by dissolving silver from a gold silver alloy, according to one embodiment of the present invention.
Figure 7B:
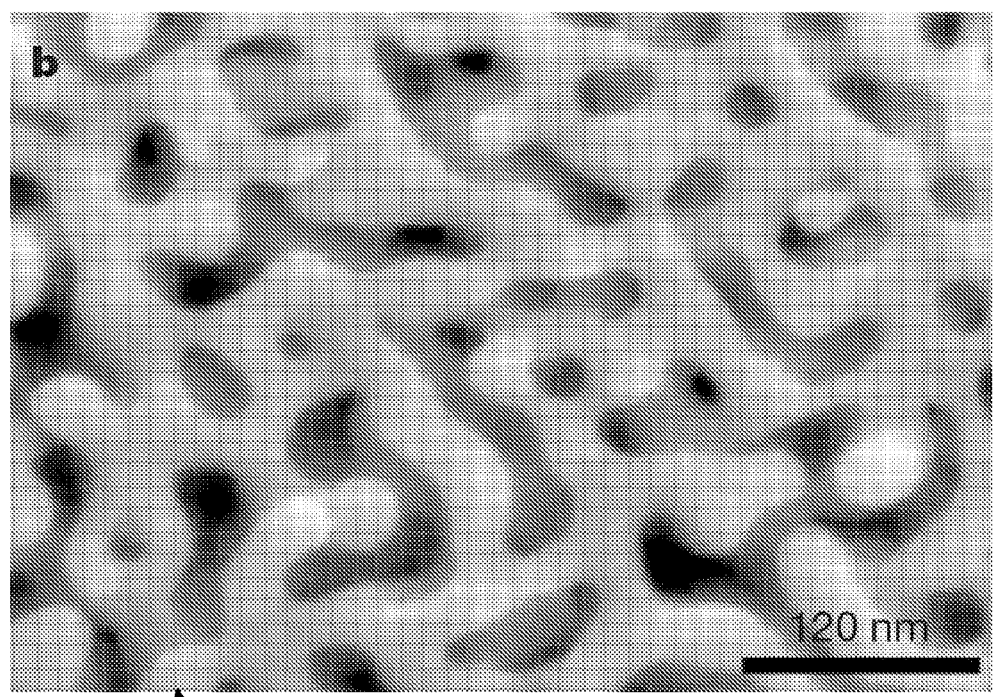

With reference now to FIGS. 7A and 7B, a porous layer 12 is shown in greater detail. FIG. 7A is an electron micrograph (approximate magnification of 46,000×) of one embodiment of the invention comprising a nanoporous gold layer created by the removal of silver from a silver/gold alloy using nitric acid. FIG. 7B is a higher magnification view (approximately 200,000×) of the nanoporous gold layer in FIG. 7A. As can be seen from the scanning electron micrographs, porous layer 12 comprises structural elements interspersed with pores. In any given embodiment, the size and density of such pores may be varied by varying one or more elements of a method for making the device and forming porous layer 12. For example, one or more components of an alloy, a substance used to selectively dissolve the alloy, duration time of exposing the alloy to the dissolving substance, or the like may be chosen to give porous layer 12 certain desired characteristics. Thermal anneals prior or subsequent to the dealloying process may also be performed to vary pore size and density. Any suitable combination of porous layer thickness, pore size, pore density and the like is contemplated within the scope of the present invention.

In one embodiment of the invention, an additional substance, including but not limited to polymers, topcoats and other material is provided in or about the porous layer to vary the elution properties of the other agents within the porous layer. That is, whereas release kinetics from the PES are normally a function of diffusion limitations as defined by Fick's law (i.e. $J_D$=DAdc/dx where $J_D$=diffusional flux, D=the diffusion coefficient of the diffusing substance, A=diffusion area, and dc/dx=the concentration gradient of the diffusing substance), and unstirred boundary layers (this alters dc/dx in the Fick equation) within the complex nanoporous coating, one may also include substances in the coating that bind drugs or therapeutic agents with low or high affinity within the coating to further control release kinetics. For example, release of heparin might be controlled by inclusion of glycosaminoglycans within the pores that bind heparin and heparin sulfate at low affinity. Similarly, one may include nanoparticles coated in such a way to bind therapeutic drugs using techniques well established to one skilled in the art. Alternatively, one may alter the surface charge of the coating to slow release through electrostatic attraction of the coating surface and an oppositely charged therapeutic agent. Some embodiments include surface coatings of materials that may alter release properties including topcoats of polymers, hydrogels, collagen, proteoglycans, diffusion barriers, biodegradable materials, and chemically active layers. These materials may also be used in combination thereby providing virtually infinite flexibility in controlling the kinetics of release of therapeutic agents.

In another embodiment of the invention, a method for producing a medical device or component with a nanoporous layer having a directional grain is provided. In the dealloying processes previously described, the interstitial space has a non-directional, tortuous, multi-branching morphology. In some instances, a nanoporous layer having directional characteristic may offer different elution characteristics that are favorable for a particular use, therapeutic agent or disease state. In one embodiment, a columnar nanoporous layer is formed by sputtering a precursor matrix onto a surface using a pressure of greater than about 10 millitorr and preferably about 20 millitorr. The sputtering pressure may vary depending upon the particular precursor matrix used, but the pressure is typically higher than the typical sputtering pressure and is sufficient to deposit the precursor matrix with a directional grain. Other deposition processes that may be used to apply a matrix with a directional grain include thermal evaporation, electron-beam evaporation, laser ablation, chemical vapor deposition, and ion beam sputtering. The directional grain is generally perpendicular to the direction of deposition, but may be further altered by the application of magnetic fields, alteration of the sputtering angle, or both. An etchant is then applied to the deposited matrix that preferentially etches between the grain boundaries of the matrix to form columnar or filamentary structures. One example of an etchant is nitric acid, but other etchants may be used, such as sulphuric acid, hydrofluoric acid, hydrochloric acid, ammonium fluoroide, sodium hydroxide, potassium hydroxide, or ferric chloride. The precursor matrix may comprise L605 alloy, gold, silver, nitinol, steel, chromium, iron, nickel, copper, aluminum, titanium, tantalum, cobalt, tungsten, palladium, vanadium, platinum, or niobium. The precursor matrix need not contain a sacrificial material as described in previous embodiments of the invention, as the directional grain of the deposited matrix can generally determine the flowpath of the non-specific etchant. This flowpath is one determinant of the morphological result of the removal process, rather than the chemical activity of the matrix subcomponents. The interstitial structures formed by such processes have a general directional characteristic, such as a filament-like or column-like structure, but may vary in other characteristics such as diameter or width, length, cross sectional shape, angle with respect to the base and spacing from other filament or column-like structures. The structures may be generally straight, curved or any combination thereof and still have a general directional characteristic. The structures may also be grouped in various shapes, numbers of structures and/or other features. Each group of structures may have different characteristics.

In other embodiments, a precursor matrix with one or more sacrificial materials is provided and one or more etchants are used to remove material from the matrix. The etchant used to remove the precursor matrix along flowpaths defined by the directional grain may be the same or different from the etchant used to remove the one or more sacrificial materials. The ranges of pore size, layer thickness, void fractions other characteristics of a directional porous layer are similar to that of the porous layers produced by the other processes described herein.

Figure 16A:
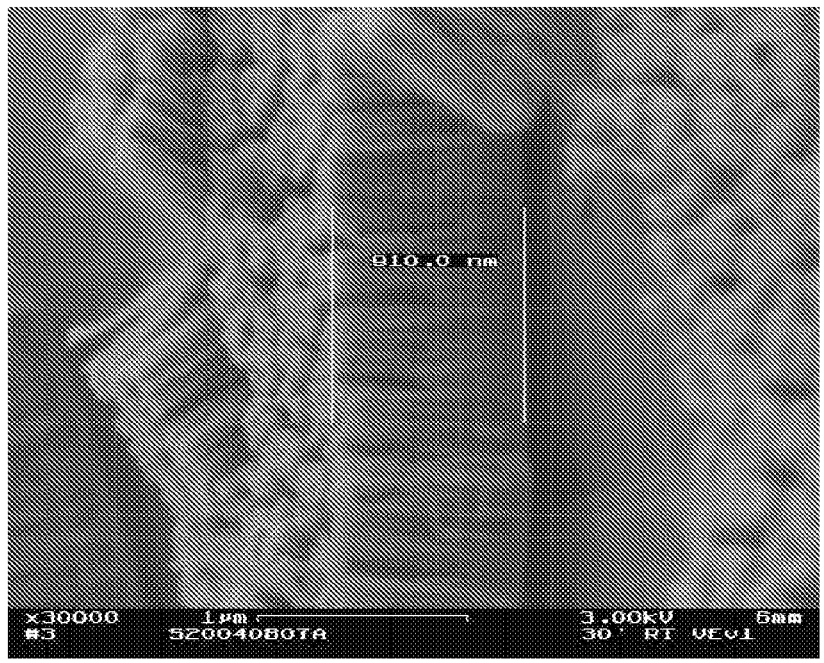
FIG. 16A is a cross sectional scanning electron micrograph of a columnar or filamentary configured porous layer.
Figure 16B:
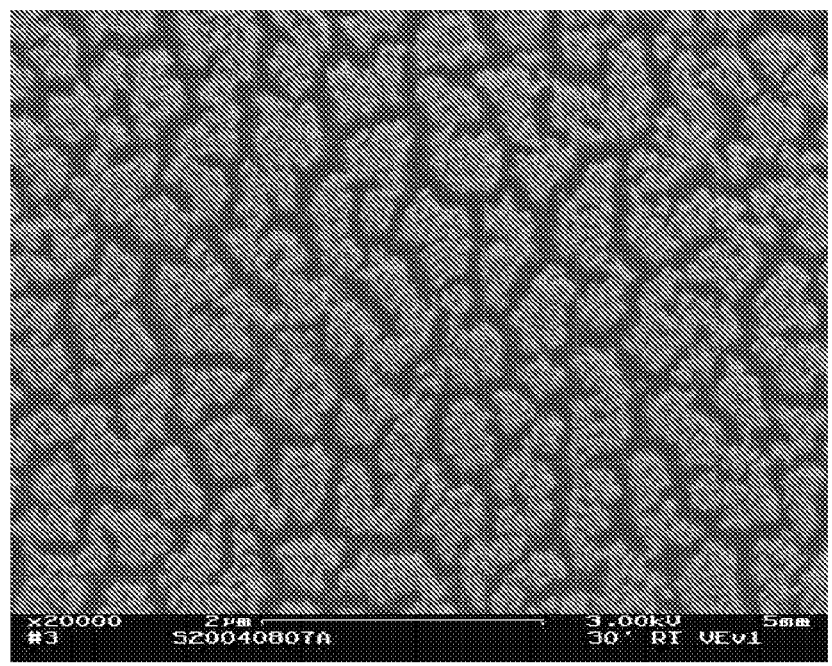
FIG. 16B is a surface view of a scanning electron micrograph of the porous layer in FIG. 16A.

In one embodiment a precursor matrix comprising L605 alloy is sputtered onto the surface of a vascular stent surface at a pressure of about 20 millitorr to a thickness of about one to two micrometers. Nitric acid is applied to the deposited layer and then rinsed with deionized water to form a filamentary surface structure as depicted in FIG. 16A. FIG. 16B is a SEM of the surface of the nanoporous layer of FIG. 16A.

As mentioned previously, multiple porous layers may be applied to the surface of a medical device. The columnar/filamentary process may be used to apply multiple columnar/filamentary porous layers to a device. The columnar/filamentary process may also be combined with a dealloying process to produce a multi-layered porous device having at least one layer with a tortuous branching configuration and at least one layer with a columnar configuration. In embodiments with three or more layers, the configurations need not be alternating. Certain multilayer configurations may be particularly suited for some applications of the invention. For example, a porous layer with a columnar structure may be less prone to clogging or initiation of fibrin deposition and can be preferentially used as the outer layer, while a noncolumnar porous layer comprises an inner layer. Alternatively, a columnar layer designed with a greater void fraction than a noncolumnar porous layer can be used as the inner layer, in order to provide a greater therapeutic agent reservoir, while the noncolumnar outer porous layer controls the elution rate of the therapeutic agent. One skilled in the art can select combinations of porous layers with differing characteristics to suit a particular use.

In other embodiments, one may design pore sizes that approach the size of the eluting substance such that elution kinetics now become a function of well defined equations for one skilled in the art relating to restricted diffusion. Multiple combinations of the preceding methods may also be employed thus providing a high degree of control of elution characteristics of therapeutic agents with the PES. In one embodiment of the invention, a medical device comprises a drug-eluting surface or zone having an average pore size of about 2 times to about 400 times the maximum diameter of a molecule or unit of the therapeutic agent to be eluted. Preferably, the average pore size is about 2.5 times to about 200 times the maximum diameter of a molecule or unit of therapeutic agent, and most preferably about 3 times to about 50 times the maximum diameter of a molecule or unit of the therapeutic agent. For example, a drug-eluting coronary stent with a dealloyed nanoporous surface for eluting rapamycin, which has a maximum diameter of 1.6 nanometers, may be used with a nanoporous layer having an average pore diameter from about 3 nm to about 640 nm, preferably a nanoporous layer having an average pore diameter from about 4 nm to about 320 nm, and most preferably a nanoporous layer having an average pore diameter from about 5 nm to about 80 nm.

Besides measures such as pore size, porous zone thickness and interstitial volume per volume of porous layer or void fraction, a nanoporous layer may be described using other measures of pore morphology that have been established or described. In addition to the ability of substantially smaller pore size, the nanoporous structure resulting from a dealloying process may be produced in some embodiments with an interconnected, tortuous pore morphology and/or a more consistent pore shape and pore diameter than can be achieved with other porous structures used in medical devices. These features allow such a nanoporous structure to provide a more similar drug-elution profile in a smaller porous layer or coating thickness than traditional non-polymeric and polymeric drug elution structures.

Figure 22A:
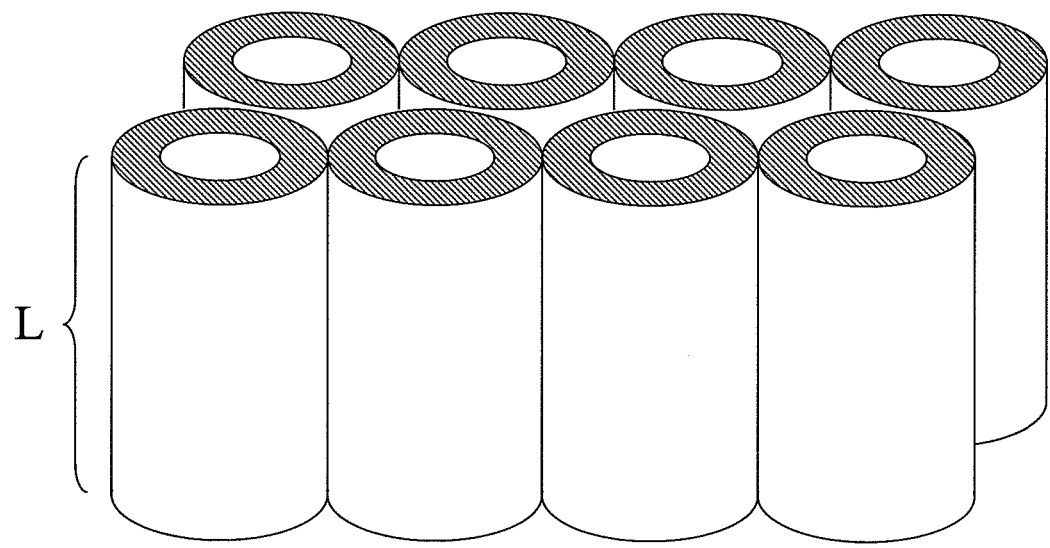
FIGS. 22A and 22B are schematic representations of an idealized capillary bundle for measuring tortuosity.
Figure 22B:
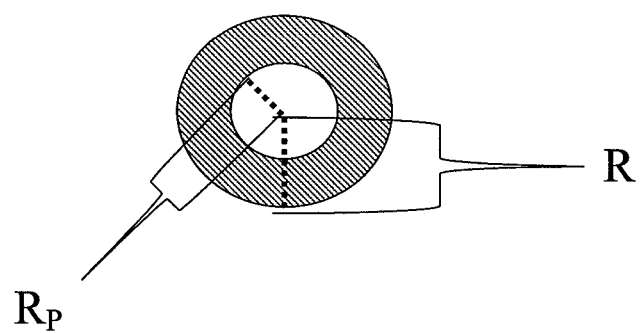

In one embodiment, the tortuosity may be measured indirectly using a tortuosity factor T, which is calculated by the ratio of the specific surface area S of the porous zone to an idealized surface area $S_0$, as depicted in FIGS. 22A and 22B, of a group of capillary bundles with a pore radius equal to that of the average pore radius of the actual porous zone:

$$T = \frac{S}{S_0}$$

(Saripalli KP, et al. "Prediction of diffusion coefficients in porous media using tortuosity factors based on interfacial areas" Ground Water, 2002. 40(4): p. 346-352, herein incorporated by reference) The specific surface area $S_0$ represents the expanse of surfaces within a porous medium with which a fluid within the porous medium must contact. Typically, this surface is a more meaningful measure of the expanse of flow within the porous medium compared to linear dimensions. The specific surface area $S_0$ may be determined experimentally using BET (Brunauer, Emmett and Teller) adsorption measurements apparatuses which are well known in the art, such as those manufactured by Porous Materials, Inc. (Ithaca, N.Y.). The idealized surface area $S_0$ can be calculated using the pore volume fraction $\phi$ and the pore radius $r_p$:

$$S_0 = \frac{2\phi}{r_p}$$

The volume fraction of pores, $\phi$, is the fraction of the coating volume that is freely accessible by fluids. This parameter may be estimated from optical and/or electron micrographs. The pore radius; $r_p$, is the average pore radius determined experimentally or estimated from optical and/or electron micrographs.

Typically, a tortuosity factor is calculated based upon a volume of stent or coating material having a width, a depth and a length and containing a plurality of pore openings. Preferably, the tortuosity factor is calculated on a volume of porous material containing at least two pore openings and preferably at least three pore openings and most preferably at least four pore openings. Anomalous results may occur when attempting determine the tortuosity factor based upon a single pore viewed in isolation.

Taking the silver-gold dealloyed nanoporous structure depicted in the micrographs of FIGS. 16A and 16B, for example, the tortuosity factor is estimated to be about 1.6, given the average pore radius of about 20 nm and an estimated pore volume fraction of about 0.50. Other dealloyed nanoporous layers, such as those derived from L605 and magnesium alloys, are estimated to achieve a higher tortuosity factor in the range of about 1 to about 10, sometimes about 1.1 to about 10, and occasionally 1.5 to about 5, while other embodiments may have a tortuosity factor of about 3.0 to about 15, or even up to a tortuosity factor of about 30. Generally, as the tortuosity factor increases, the elution rate from the porous layer decreases. The drug-elution profile of a therapeutic agent may be controlled by altering the tortuosity of the pore structure of the nanoporous zone or layer. Although it is believed that increasing tortuosity by increasing the surface area may have a greater effect on elution rates, altering the specific surface area S by decreasing the pore diameter may not increase tortuosity because the idealized surface area will also increase. This typically maintains the tortuosity factor at about the same magnitude. The ranges of the tortuosity factor described above for dealloyed nanoporous layers are typically higher than those achieved by sintering or ordered aggregation of nanostructures, which tends to have lower void fractions because the sintered particles or nanoparticles take up most of the space, and from disordered aggregation of nanostructures, which often have higher void fractions due to the poor stacking function of the nanostructures, but result in a lower tortuosity factor because straight passageways through the entire thickness of the pore structure are often found throughout the aggregated nanostructures. Similarly, the increase in surface area as defined by a plurality of discrete pore openings spaced about the surface of a medical device, such as those described in U.S. Pat. No. 6,379,381 to Hossainy, is far less than that achieved by a dealloyed porous zone or layer.

In one embodiment of the invention, the tortuosity factor may be manipulated to control the elution kinetics of one or more therapeutic agents within the porous medium. For example, the diffusion coefficient of a therapeutic agent within a porous medium, $D_p$, is generally related to the ratio of the diffusion coefficient of the therapeutic agent in bulk solution, $D_B$ over the tortuosity factor:

$$D_p = \frac{D_B}{T}$$

Figure 23A:
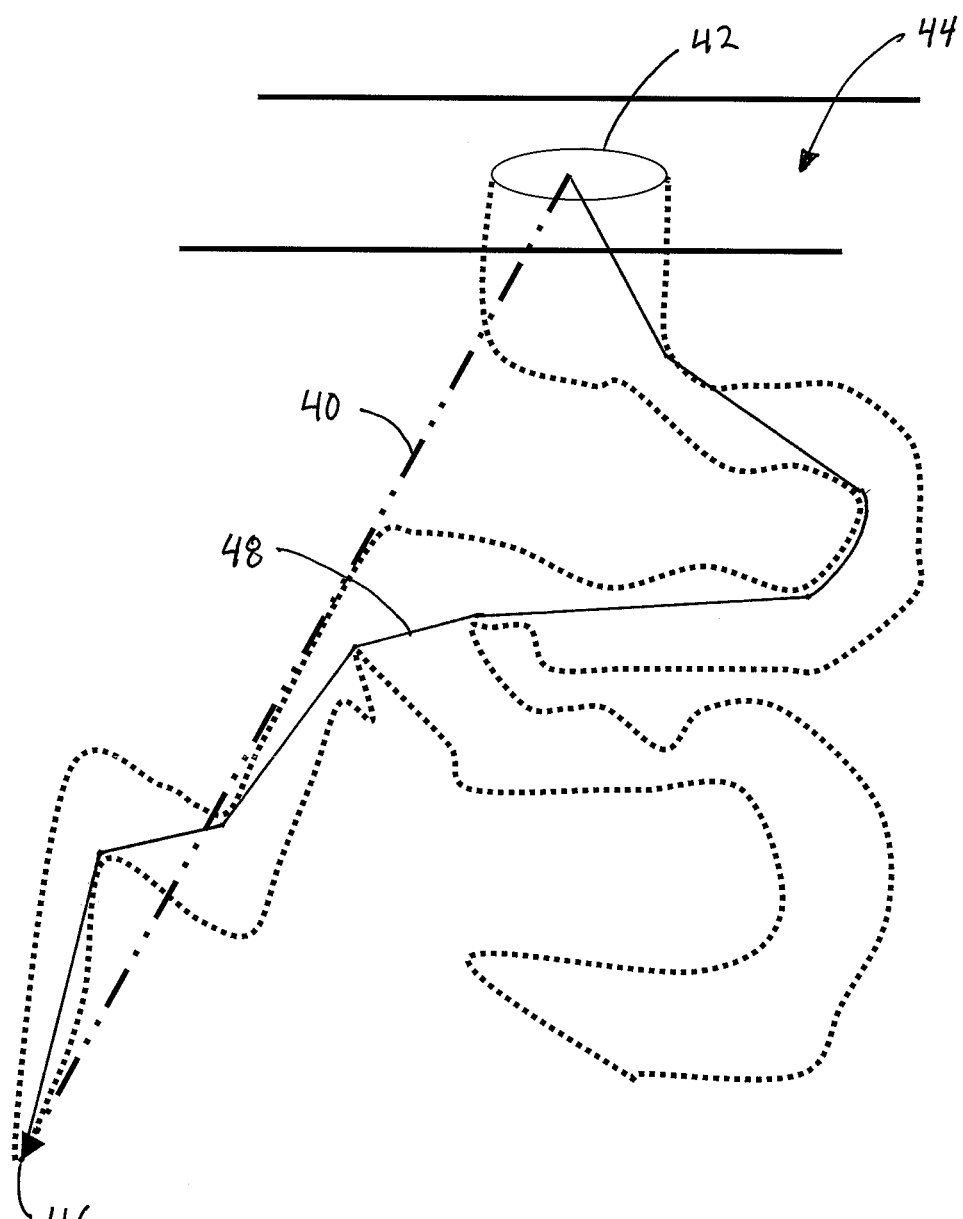
FIGS. 23A and 23B are schematic representations of an isolated pore opening and an isolated pore passageway in a porous zone for measuring tortuosity.
Figure 23B:
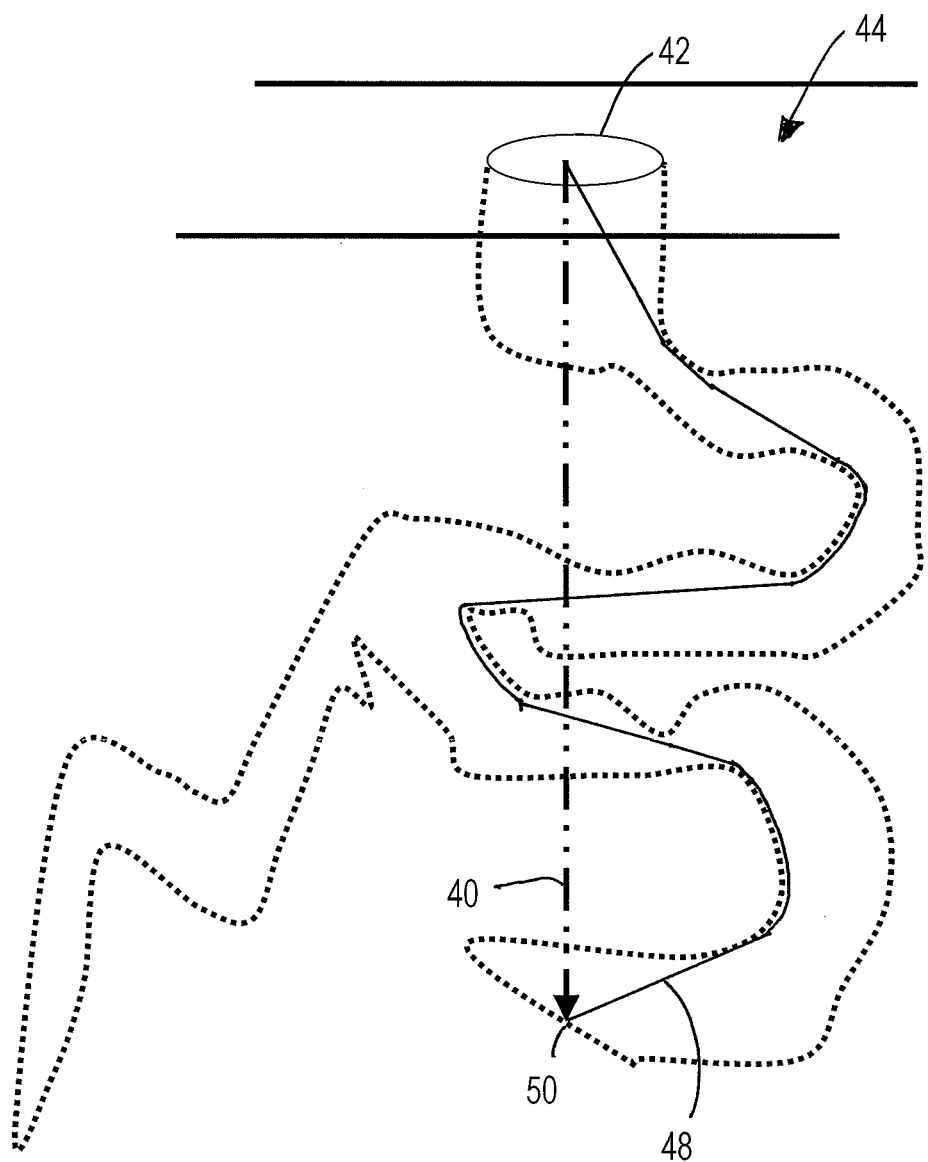

Alternatively, the tortuosity of a porous structure or layer may be characterized based upon the ratio of the length of the shortest pore pathway 40 between a pore opening 42 at the surface 44 or interface of the porous zone and the farthest contiguous point 46 in the pore structure from the pore opening 40, and the length of the straight line 48 between the pore opening 42 and same farthest contiguous point 46, as shown in FIG. 23A, or alternatively the ratio as compared to the farthest contiguous point 50 in the pore structure that is perpendicular in depth from the pore opening 42, as shown in FIG. 23B. In some embodiments, a dealloyed porous zone will have a tortuosity ratio of about 1.05 to about 20.00, sometimes about 1.05 to about 5.00, preferably a tortuosity ratio of about 1.20 to about 3.00, and most preferably about 1.25 to about 1.75.

The pore diameter of a dealloyed porous zone can also be characterized by the variability of the pore diameter. In some embodiments of the invention, as shown in FIGS. 16A and 16B, the pore diameter of a dealloyed porous zone has a consistency whereby the standard deviation of the average pore diameter throughout the porous zone is not more than about 2 times the average pore diameter, and preferably not more than about the average pore diameter, and most preferably no greater than about 0.25 times the average pore diameter. In other embodiments, however, the pore diameter may be more varied and/or irregular.

Still another parameter for characterizing the pore structure of a porous zone or coating is the pore shape. One measure of pore shape is described in T. M. Cimino, A. H. Graham, T. F. Murphy ve A. Lawley, "The Effect of Microstructure and Pore Morphology on Mechanical and Dynamic Properties of Ferrous P/M Materials", Advances in P/M & Particulate Materials, Proc. Int. Con., Vancouver, MPIF, 1999, Vol. 2, pp. 7-65/7-84, herein incorporated by reference in its entirety. The pore shape calculated as a Form Factor related to the area of the pore (A) and the circumference of the pore (P) in a plane on optical microscopy or scanning electron microscopy as follows:

Form Factor=$4\Pi A/(P)^2$

In some embodiments of the invention, the dealloyed porous zone has an average pore form factor of about 0.05 to about 1.00, sometimes about 0.40 to about 0.80, or about 0.50 to about 0.80, and at other times about 0.10 to about 0.60, or about 0.20 to about 0.60.

A porous layer or medium may also be characterized by the roughness of the porous layer surface. The roughness of the surface of a porous layer may be characterized by established surface metrology standards (e.g. ASME B46.1-1995 or ISO 4287-1997, herein incorporated by reference in their entirety) that disclose a variety of surface profile parameters. The roughness of a surface may be characterized by how a surface deviates from its mean line over an evaluation length. This evaluation length is typically measured over range of about 10 microns to about 100 microns, sometimes over a range of about 20 microns to about 50 microns, and occasionally over a range about 30 microns to about 200 microns. One commonly used parameter includes peak-valley surface roughness, $R_t$, which is the total sum of the height of the highest peak from the mean line and the depth of the deepest valley from the mean line across an evaluation length. Using this measurement, a dealloyed porous zone or medium typically has a peak-valley surface roughness of about 0.1 microns to about 2.5 microns, sometimes a peak-valley surface roughness of about 0.2 microns to about 2.0 microns, and occasionally about 0.5 microns to about 1.0 microns. This and other roughness measures may be determined by using any of a variety of well established techniques, including white light interferometry, Atomic Force Microscopy (AFM), Scanning Electron Microscopy (SEM) stereo imaging, and Focused Ion Beam (FIB) combined with SEM imaging (cross section).

D. Manufacturing of Porous Layers

Figure 8A:
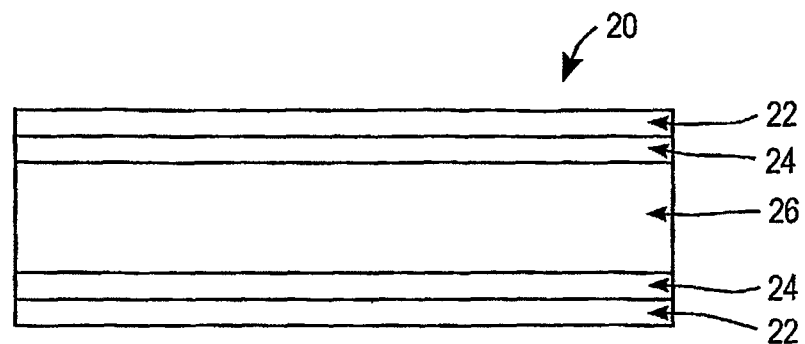
FIGS. 8A-8C are schematic cross sectional side views showing a method of making an implantable stent device having a porous layer, according to one embodiment of the present invention.
Figure 8B:
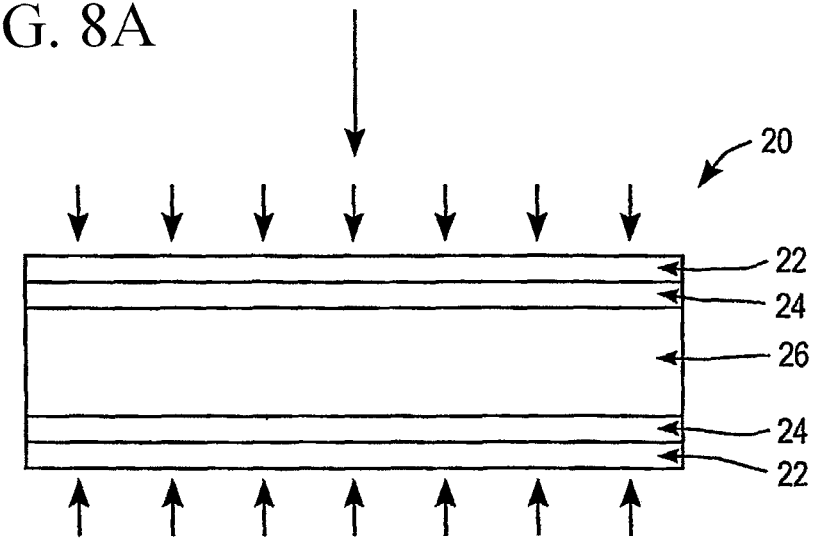
Figure 8C:
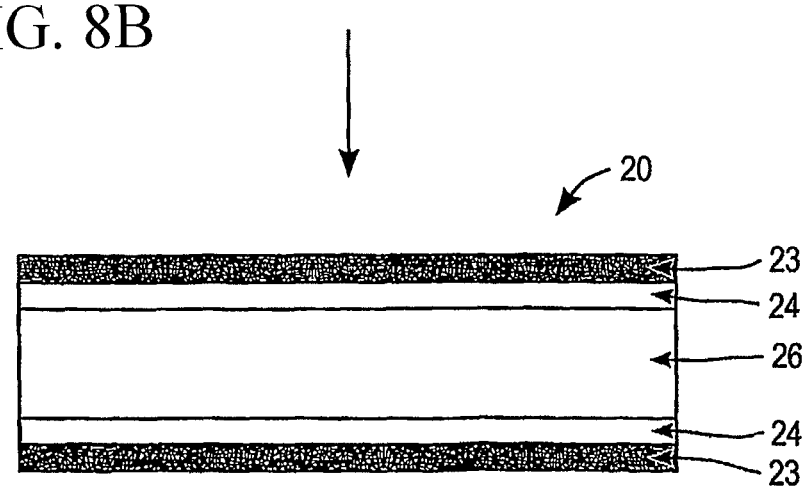

Referring now to FIGS. 8A through 8C, a method for fabricating an implantable medical device 20 having a porous layer suitably includes providing an implantable device comprising at least a matrix of two or more materials or components and removing at least one component of the matrix to form the porous layer. A matrix will typically have one or more sacrificial materials and one or more structural materials, the sacrificial materials generally capable of removal by a component removal process while generally leaving at least one of the structural materials generally intact.

As shown in the cross sectional FIG. 8A, a medical device 20 such as a stent may include a precursor matrix layer 22, a substrate layer 24 and a lumen 26. Precursor matrix layer 22 can be deposited onto substrate layer 24 by various processes, including but not limited to physical vapor deposition, ion implantation, sputter deposition, thermal or electron beam evaporation, chemical vapor deposition, pulsed laser deposition, or the like. Using such techniques, precursor matrix layer 22 may be synthesized in situ from various materials, as described previously, such that exposure to a component removal process will remove the sacrificial component of precursor matrix layer 22, leaving behind a porous matrix. In another embodiment, precursor matrix layer 22 and substrate layer 24 may be made from the same material.

As previously described, medical device 20 may comprise any suitable stent or other device and precursor matrix layer 22, substrate layer 24 and/or other layers may be given any suitable configurations, thicknesses and the like. In some embodiments, precursor matrix layer 22 is disposed along an outer surface of device 20, while in other embodiments, precursor matrix layer 22 may be disposed along an inner surface, both inner and outer surfaces, or the like. The matrix used to form precursor matrix layer 22 may comprise any suitable matrix and may be a metal, metal alloy, metal/nonmetal matrix, non-metal/non-metal matrix or a combination of three or more components. In various embodiments, for example, components of precursor matrix layer 22 may include steel, nitinol, chromium, brass, copper, iron, nickel, aluminum, titanium, gold, silver, tantalum, cobalt, tungsten, palladium, vanadium, platinum and/or niobium. In some embodiments, one or more additional substances may be embedded within precursor matrix layer 22 to cause or enhance pore formation during the fabrication process. For example, a salt, an oxide particle or the like may be added to precursor alloy layer 22 to enhance pore formation.

In one embodiment, the matrix comprises gold as a structural material and sodium chloride crystals as a sacrificial material, becoming porous after immersion in a water bath. The size of the pores may be determined by the dimensions of the salt crystals. Alternatively, quartz or silicon dioxide nanoparticles could be used as a sacrificial material distributed inside a matrix employing platinum as the structural material. This matrix would form a porous platinum layer after dissolving the quartz or silicon dioxide nanoparticles in hydrofluoric acid. It is also possible to combine nonmetallic structural materials with nonmetallic sacrificial materials; an example would be a porous layer of silicon nitride formed from a matrix of codeposited silicon nitride and polystyrene beads, followed by a sacrificial etch in acetone. A nonmetallic matrix employing a metallic sacrificial material is also within the scope of this invention. An example would be a porous layer of polydimethylsiloxane (PDMS) formed from a matrix of PDMS and nickel nanoparticles, followed by etching of the nickel in nitric acid. One skilled in the art will understand that many other combinations of materials are possible.

In one embodiment, the structural layer is metallic, and the sacrificial material is silicon dioxide. Preferably, the matrix is fabricated by cosputtering the structural layer metal and the silicon dioxide. Preferably, the silicon dioxide sacrificial material is sputtered from a stoichiometric silicon dioxide target. Alternatively, the silicon dioxide sacrificial material is reactively sputtered from a silicon target using a sputter gas mixture containing oxygen and at least one other gas. Preferably, the other gas is argon.

As shown in FIG. 8B, implantable medical device 20 is typically exposed to a substance or energy source (arrows) to dissolve or otherwise remove at least one component of the alloy to form the porous layer from precursor alloy layer 22. In various embodiments, any suitable substance may be used for removing at least one component of the alloy. In one embodiment, for example, the alloy comprises stainless steel, such as 316L stainless steel, and dissolving at least one component of the steel comprises exposing the steel to hot sodium hydroxide to dissolve chromium and leave iron and nickel as the porous layer. In another embodiment, a silver gold alloy may be exposed to nitric acid to dissolve the silver and leave the gold as the porous layer (as shown in FIGS. 7A and 7B).

In another embodiment, a cobalt chromium alloy, such as L605, is modified by the addition of a sacrificial material such as silver, copper or aluminum, which is subsequently removed by processing in an appropriate solvent, such as nitric acid, sulfuric acid or phosphoric acid, to leave a porous film of the original cobalt chromium alloy. In another embodiment, a platinum copper alloy is dealloyed in the presence of sulfuric acid to produce porous platinum. In some embodiments, nitinol may be dissolved by a suitable dissolving substance to leave a porous layer. The dissolving process may include the use of electro chemical cells to bias device 20 in solution so as to facilitate the dealloying process. Any other suitable combination of alloy and dissolving or component removing substance is contemplated. Furthermore, any means for exposing medical device 20 to a dissolving substance or energy source such as heat or energetic plasma is contemplated. For example, medical device 20 may be immersed in, sprayed with, coated with, etc. any suitable substance or combination of substances.

As shown in FIG. 8C, one or more components of precursor alloy layer 22 are selectively removed to form a porous layer 23. In some embodiments, removing at least one component of the alloy comprises dissolving one or more of the most electrochemically active components of the alloy. For example, in a steel alloy the chromium component may be dissolved, leaving the iron and nickel components. Additional processing of medical device 20 may include introduction of one or more therapeutic agents into porous layer 23. Any suitable agent(s) may be introduced and they may be introduced by any desired method. For example, methods for introducing therapeutic agents include, but are not limited to, liquid immersion, vacuum desiccation, high pressure infusion, vapor loading, and the like. Additional unique loading methods, or variations of the preceding methods are described in detail elsewhere in this application.

E. Thermal Dealloying

In another embodiment of the invention, a thermal method of creating a porous layer is provided. A thermal method of removing a sacrificial material may be advantageous in some situations compared to chemical removal with an etchant. For example, removal with an etchant may reduce the integrity of the resulting matrix layer through hydrogen embrittlement. An etchant may also affect the loading characteristics of the porous layer due to surface adsorbents or incomplete dealloying. In one embodiment, a precursor matrix with one or more structural materials and one or more sacrificial materials is deposited onto a medical device. At least one sacrificial material is selected for its boiling point and/or vapor pressure. By thermally treating the precursor matrix on the medical device under particular conditions, at least a portion of the sacrificial material may be removed from the matrix. The thermal process may be repeated to obtain the desired degree of dealloying and to achieve the desired dealloying in thicker porous layers. The sequential layers of porous material produced by this method can have the same or different porosities. With materials having different porosities, the effect of multiple intermediate thermal dealloying may reduce interdiffusion of the sacrificial components and produce PES layers with more abrupt transitions between porosities.

Heat sources that may be used with the thermal method include but are not limited to infrared radiation, visible light, ultraviolet radiation, inductive heating, laser illumination, high-frequency ultrasound or combinations thereof. Heat sources capable of raising the matrix temperatures to between about 400° Celsius to about 500° Celsius may be used, but heat sources capable of raising matrix temperatures to about 600° Celsius are preferred. Typically, thermal treatment will be performed under a vacuum environment to reduce contamination related problems from the thermal process, but this is not required. In one embodiment, the thermal dealloying process is performed at a vacuum level of about $10^{-5}$ torr or less. In other embodiments, the thermal dealloying process is performed at high vacuum from about $10^{-6}$ torr to about $10^{-8}$ torr. In still other embodiments, the thermal dealloying process is performed at ultra-high vacuum conditions of about $10^{-9}$ torr or less.

The thermal dealloying process, and the other processes described, can also be performed in the presence of a reactive gas such as hydrogen, chlorine, oxygen, or a reactive plasma such as oxygen, sulfur hexafluoride, or chlorofluorocarbons. The reactive gas or plasma may accelerate the removal of the sacrificial material. Energy from other optical or acoustic sources may be applied to further alter the thermal removal process or other removal processes.

Structural materials of the precursor matrix used for the thermal dealloying process include but are not limited to L605, stainless steel, platinum, gold, tantalum titanium, nitinol and combinations thereof. Sacrificial materials may include magnesium and indium. One skilled in the art can select various combinations of structural and sacrificial materials to use as a precursor matrix. One example of a precursor matrix is L605 cosputtered with about 20% to about 40% magnesium. The precursor matrix may be deposited upon a heated, unheated or cooled substrate, but unheated substrates are preferred.

The thermal method may used in combination with one or more other processing methods described herein to produce a programmable elution system having the desired configuration and/or characteristics. The order, sequence and/or repetition of the various removal processes may affect the final configuration and characteristics of the porous layer. In one example, the thermal dealloying process is first used to form the initial porous layer configuration, followed by a chemical etching process which can increase the pore size of the initial porous layer configuration with varying degrees of specificity.

F. Modification of Nanoporous Structures

Another embodiment of the invention comprises a method for further modification of a porous material. An existing porous material may have pores with a characteristic dimension and density that is suboptimal for the desired elution profile of the PES. For example, the existing pore structure may be insufficiently small for the desired elution profile. By providing a method for coarsening the structure of a porous material, a higher void fraction may be achieved. The modified structure may be better suited for some therapeutic uses than the original structure of the PES. A modification process may also simplify the manufacture of the PES by reducing the number of base structures produced during the initial manufacturing process, which are then used to produce variations of the PES through further modification processes. These adjuvant processes may remove the structural (i.e. non-sacrificial) material from the PES instead of limiting removal to sacrificial components of the precursor matrix. In one example, an anisotropic etchant may be used to increase the pore volume with further modification of general pore morphology. An anisotropic etchant removes material from the remaining porous layer at different rates along different directions in the matrix. Isotropic etchants can also be used to increase the characteristic dimension of the pores while maintaining the general pore structure morphology. These processes can be utilized to remove additional sacrificial material that was isolated in the porous matrix, allow rearrangement of the microstructure, alter the mechanical properties of the porous film, and/or the surface related effects of a porous structure.

The processes involved in making a porous material can also influence the other resultant properties of the material. In many dealloying and non-dealloying processes, the surface characteristics of the precursor matrix and the corresponding porous layer or film may affect the energetics and kinetics of the formation of resulting porous material. In some embodiments of the invention, the desired features of the porous material originate less from the contribution of material properties from the bulk material and more from the influence of surface related effects. For instance, the particular surface effects or states of a porous layer may be advantageous in loading, retaining or eluting a therapeutic agent. In some embodiments, the surface states for a given porous material may be affected by crystallographic projections and associated surface terminations throughout the porous material. Surface states can have specific energetics related to the physical structure, composition, and environmental history of the porous material. Through the use of chemical and thermal processes, the surface of the porous material can be tailored for the desired chemisorption or physisorption properties. This tailoring may be performed with etchants having various properties. Isotropic etchants are indiscriminate in the removal of atomic species and leave the surface characteristics of the porous layer relatively unchanged, while anisotropic etchants can preferentially remove material from a subset of orientations thereby skewing the distribution of surface states. Under some thermal and chemical processes, the physical arrangement of atoms on the surface can be altered or undergo surface reconstruction. Surface reconstruction with thermal and chemical processes can be used to control the retention or release of the drug.

In some embodiments, a protective layer or coating may be formed or added to medical device 20, such as a titanium, gold or platinum layer or coating. If there is a concern that porous layer 23 may not be biocompatible, a passivation layer may be deposited into porous layer 23 to enhance biocompatibility. For instance, a very thin layer of gold may be electroplated into the dealloyed porous layer 23. Electroless deposition may also be used to achieve the same effect. Depending on the composition of porous layer 23, the porous coating may also be passivated chemically or in a reactive ion plasma.

G. Use of Therapeutic Agents with a Porous Layer

Any implantable medical device of the present invention may include one or more therapeutic agents disposed within one or more porous layers 12. As discussed above, any agent or combination of agents may be included. Additionally, as described further below, any suitable method for introducing an agent into a porous layer may be used.

The porous layer or layers of a medical device may be loaded with one or more of any of a variety of therapeutic agents, including but not limited to drug compounds, hormones, pro-hormones, vitamins, an anti-restenosis agent, an anti-thrombogenic agent, an antibiotic, an anti-platelet agent, an anti-clotting agent, an anti-inflammatory agent, a chelating agent, small interfering RNAs (siRNAs), morpholinos, antisense oligonucleotides, an anti-neoplastic agent, a radiocontrast agent, a radio-isotope, an immune modulating agent, a prodrug, antibody fragments, antibodies and live cells, actinomycin-D, batimistat, c-myc antisense, dexamethasone, paclitaxel, taxanes, sirolimus, tacrolimus and everolimus, unfractionated heparin, low-molecular weight heparin, enoxaprin, hirudin, bivalirudin, tyrosine kinase inhibitors, GLEEVEC (imatinib mesylate), wortmannin, PDGF inhibitors, AG1295 (6,7-Dimethyl-2-phenylquinoxaline, rho kinase inhibitors, Y27632 ((+)-(R)-trans-4-(1-aminoethyl)-N-(4-pyridyl)cyclohexanecarboxamide dihydrochloride), calcium channel blockers, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, and roxifiban. Therapeutic drug delivery microspheres as described by Unger et al. in U.S. Pat. No. 5,580,575 and vectors for performing localized gene therapy are also usable with the porous layers. These vectors may include viral vectors and plasmid DNA vectors.

Other suitable therapeutic substances may include other glucocorticoids (e.g. betamethasone), angiopeptin, aspirin, growth factors, oligonucleotides, and, more generally, antimitotic agents, antioxidants, antimetabolite agents, and anti-inflammatory agents could be used. Antimitotic agents and antimetabolite agents can include drugs such as ABT-578, CCI-779, biolimus-A9, temsirolimus, methotrexate, azathioprine, vincristine, vinblastine, 5-fluorouracil, adriamycin and mutamycin. Antibiotic agents can include penicillin, cefoxitin, oxacillin, tobramycin, and gentamycin. Other specific agents may include anti-CD34 antibodies, mycophenolic acid, Vitamin E, omega-3 fatty acids, tempamine, docetaxel, an agent for altering cytochrome P450 function, cyclosporine, an azole antifungal agent, itraconazole, ketoconazole, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, grapefruit juice extract, mifepristone, nefazodone, a rifamycin including rifabutin, rifampin and rifapentine, an anti-convulsant including carbamazepine, phenobarbital and phenyloin, an anti-HIV agent including efavirenz and nevirapine, and an herbal agent including St. John's Wort. The therapeutic agent may also be any macrocyclic lactone, any cell cycle inhibitor that acts selectively at a G1 phase of a cell cycle, inhibitors of cyclin dependent kinases involved with progression of cell cycle through the G1 phase of the cell cycle, any one or more of a group of flavopiridol and its structural analogs, agents that elevate endogenous P27 kinase, inhibiting protein, staurosporin and related small molecules, protein kinase inhibitors including the class of tyrphostins that selectively inhibit protein kinase to antagonize signal transduction in smooth muscle in response to a range of growth factors, an inhibitor of mammalian target of rapamycin, or any agent that is an analog or congeners that binds a high affinity cytosolic protein, FKBP 12 and possesses the same or similar pharmacologic properties as rapamycin.

In one embodiment, the drugs or biologically active materials which can be used in the invention can be any therapeutic substances such as those which reduce or prevent adverse physiological reactions from exposing body tissue to the medical device. In one specific embodiment, the drugs incorporated into the porous layer are substantially free of ionic surfactants. The drugs may be of various physical states, e.g., molecular distribution, crystal forms or cluster forms.

In another embodiment of the invention, a medical device or stent with a porous zone is provided with a first therapeutic agent for treating the tissue or vessel about the medical device or stent, along with a second agent for altering the degradation, uptake or other pharmacological property of the first therapeutic agent. In one example, the tissue or blood concentrations of the first therapeutic agent may be altered through changes in the cytochrome P450 enzyme system that is often involved in the metabolism of drugs. Although the cytochrome P450 system is typically identified with the liver, there is also evidence that the system has significant activity in the enterocytes of the small intestine and the endothelial and smooth muscle cells of a vessel wall, in particular the CYP3 family of cytochrome P450 genes. Other cytochrome P450 genes, such as the CYP1, CYP2 and CYP4 families, may also be involved. For a particular therapeutic agent, one or multiple families of cytochrome P450 enzyme may be involved in the metabolism of that agent. In a preferred embodiment, a therapeutic agent that is metabolized by the cytochrome P450 system may be used in combination with an inhibitor of the cytochrome P450 system including but not limited to cyclosporine, an azole antifungal agent, itraconazole, ketoconazole, a calcium channel blocker, diltiazem, verapamil, a macrolide antibiotic, clarithromycin, erythromycin, troleandomycin, an non-nucleoside reverse transcriptase inhibitor, delavirdine, a protease inhibitor, indinavir, ritonavir, saquinavir, ritonavir, a selective-serotonin reuptake inhibitor, fluoxetine, an $H_2$ receptor antagonist, cimetidine, an herbal medicine, grapefruit juice extract, mifepristone, and nefazodone. Note, however, the use of these agents in a therapy eluting medical device may not be limited to their use as a cytochrome P450 system inhibitor. In other embodiments, an agent for inducing the cytochrome P450 system may also be used, including but not limited to a rifamycin including rifabutin, rifampin and rifapentine, an anti-convulsant including carbamazepine, phenobarbital and phenyloin, an anti-HIV agent including efavirenz and nevirapine, and an herbal agent including St. John's Wort. A cytochrome P450 inducer may be useful because it may reduce system side effects from localized delivery of a therapeutic agent that is metabolized by the cytochrome P450 system. In some embodiments, a cytochrome P450 inhibitor and a cytochrome P450 inducer may be used in conjunction with a therapy agent. For example, the effect of a locally delivered therapy agent may be boosted by the localized delivery of a cytochrome P450 inhibitor while a cytochrome P450 inducer may be provided either systemically or from a different localized site or a site downstream from the cytochrome P450 inhibitor to reduce side effects of the therapeutic agent. Although the embodiments described above refer to a first therapeutic agent and a second agent for modifying pharmacological effect of the first therapeutic agent, in other embodiments of the invention, more than one therapeutic agent and/or more than one modifying agent may be provided. Any one therapeutic agent may be affected none, one or multiple modifying agents, and any given modifying agent may affect one or more therapeutic agents.

For example, ritonavir, an HIV protease inhibitor known to be one of the most potent inhibitors of the metabolic enzyme cytochrome P450 monooxygenase, may be used to improve the pharmacokinetics of a drug (or a pharmaceutically acceptable salt thereof) which is metabolized by cytochrome P450 monooxygenase comprising coadministering ritonavir or a pharmaceutically acceptable salt thereof. When administered in combination, the two therapeutic agents can be formulated as separate compositions which are administered at the same time or different times, or the two therapeutic agents can be administered as a single composition. Drugs which are metabolized by cytochrome P450 monooxygenase and which may benefit from coadministration with ritonavir include cyclosporine, FK-506, rapamycin, paclitaxel, taxol, taxotere and others.

In one embodiment of the invention, a pro-drug and a reactant are loaded into the porous layer of a medical device. The reactant is capable of converting the prodrug to its active form. By using a reactant/prodrug pairing, the effect of the active form of the prodrug may be at least partially localizable to the implantation site of the device. This may reduce the systemic side effects of a therapeutic agent. A reactant/prodrug pairing may also provide therapeutic activity with an implant that is otherwise not achievable due to the short half-life of an active drug. In other embodiments, one or more reactants found systemically or locally at the implantation site are used to convert the prodrug into active form. Such reactants may include systemically available or localized enzymes.

In another embodiment, multiple therapeutic agents may be introduced into a porous matrix composed of a plurality of porous layer 23. As described previously, the plurality of porous layers may vary in atomic composition, as well as in pore size and density. Compositional variations may allow for preferential binding to occur between the therapeutic agent and the coating, changing the elution kinetics of the agent. Pore size and density will also affect the transport kinetics of therapeutics from and across each layer. The use of a plurality of porous layers may thus allow for controlling elution kinetics of multiple therapeutic agents.

In a further embodiment, live cells may be encapsulated within lumen 26 of device 20. In one such embodiment, the entire device may be made porous (such that the internal lumen and the exterior of the device are separated by a porous layer). Live cells (such a pancreatic islet cells) can be encapsulated within the internal lumen, and the porosity of the layer adjusted to allow transport of selected molecules (such as oxygen, glucose; as well as therapeutic cellular products, such as insulin, interferon), while preventing access of antibodies and other immune system agents that may otherwise attack or compromise the encapsulated cells.

H. Loading of Therapeutic Agents into a Porous Layer

A major challenge for using nanoporous coatings is to identify effective methods for loading therapeutic agents in a manner that carefully controls dosage, drug stability, drug mass, biocompatibility, release kinetics, and overall device efficacy. One limitation that must be overcome is that coatings contain trapped air that can impede loading with drug loading solvents. This limitation can be overcome using wetting processes as well as vacuum and/or pressure loading techniques during, following, and preceding introduction of the solvent containing the therapeutic agent. One may also replace the gas within the coating prior to the loading process with one that has high solubility in the loading solvent thus facilitating gas removal by diffusion processes and/or use solvents that have high solubility with air. For example, one may use nitrogen or $CO_2$ gas that have higher solubilities than air in many hydrophobic and hydrophic solvents compatible with loading therapeutic agents. One may also use the vapor or gas phase of the loading solvent in question in a "prewetting" step to greatly improve filling of the nanopores within the PES with the loading solution.

Solvents used in the loading process must also have appropriate viscosities and wetting properties to allow their penetration deep into the nanoporous coating, but also appropriate vapor pressures to enable effective elimination of solvents after loading to ensure biocompatibility, drug stability, rewetting with body fluids, and/or appropriate elution of the therapeutic agent. Several unique methods have been identified that overcome these limitations.

One method is to simply dip the coated biomedical device into the solvent containing the therapeutic agent but using solvents with appropriate solubility properties, vapor pressures, viscosity, and wetting properties to achieve appropriate loading of the coating. One embodiment would be to use ethanol for loading rapamycin or rapamycin analog. Another embodiment is to use graded concentrations of ethanol, other solvents, or co-solvents that have different solubility properties for the therapeutic agent to provide a wide range of concentrations for loading. Following loading, the biomedical device can then be subjected to controlled washes or other specialized processing steps (see below) and subsequently air dried or dried under controlled vacuum for storage prior to subsequent manufacturing processes including sterilization, and packaging. This method is most applicable to thin coatings (e.g. <1 micron) but may also be used for depositing therapeutic agents selectively on and within the upper layers of thicker coatings (>1 micron).

Another method that may be desirable for loading thicker coatings includes performing loadings under controlled vacuum (subatmospheric) pressures. This includes use of both constant vacuum and with stepped or ramped changes. In some embodiments of vacuum loading, it is beneficial to optimize vacuum pressures relative to solvent vapor pressures. For example, one can load rapamycin in ethanol, acetone, methanol, benzyl alcohol, DMSO or other solvent with high rapamycin solubility under vacuum pressures that just exceed the vapor pressure of the solvent in question. Following loading for varying times from 1 minute to 30 days or more depending on the coating thickness, the solvent can be removed by air drying or drying under vacuum pressures exceeding the vapor pressure of the solvent in question.

In another embodiment, the coating is placed in a subatmospheric pressure below the vapor pressure of the loading solvent to induce exchange of trapped air with the vapor phase of the loading solvent. One then can introduce the PES device into the loading solution containing the therapeutic agent at either subatmospheric, ambient, or supraatmospheric pressure to optimize loading of the solvent containing the therapeutic agent(s).

For example, in the case of ethanol, vacuum loading is typically done at 60 torr or a pressure that exceeds the vapor pressure of 100% ethanol that is approximately 45-50 torr at room temperature. Ideally, the vacuum pressure used will be 0.1 to 5 torr greater than the vapor pressure of the loading solvent (or solvents) under the conditions of the loading to prevent excessive or rapid loss of solvent during the loading process. However, in some embodiments, one may deliberately cycle below and above the vapor pressure to facilitate removal of trapped gas, and effective replacement with solvent containing the therapeutic agent. The cycle times will typically be for periods ranging from 1-5 seconds in some applications, 5 seconds to 1 minute, 1 minute to 10 minutes, or 10 minutes to several hours depending on the solvents, vapor pressures, agent being loaded, temperature, and other loading conditions. Following loading, the samples are then subjected to procedures to control the amount of surface deposition of therapeutic agent (see below), and either air dried or dried under vacuum pressures lower than the vapor pressure of water, and/or increased temperature to ensure effective elimination of the solvent. One may also perform the loading process at reduced temperature to lower the solvent vapor pressure, thus allowing use of lower vacuum pressures to facilitate more effective removal of air and replacement with the loading solution. That is, one can reduce the loading temperature to just above the freezing point of the solvent to enable use of the lowest vacuum pressure possible.

Figure 9A:
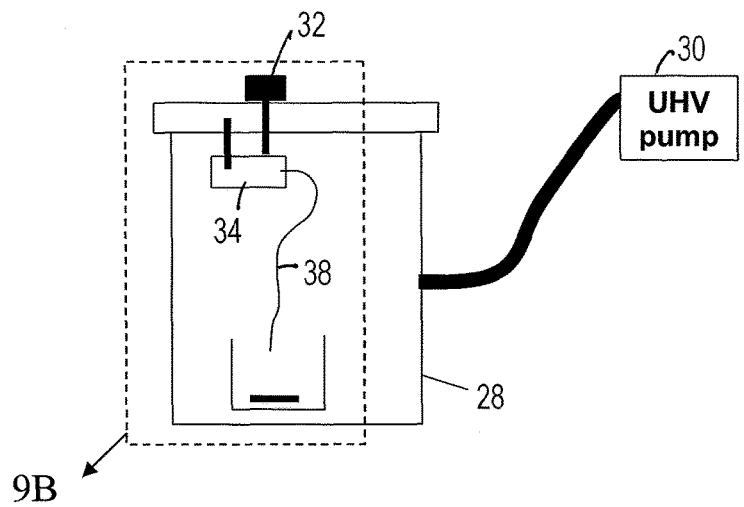
FIG. 9A is a schematic representation of one embodiment of a therapy loading device for a stent.
Figure 9B:
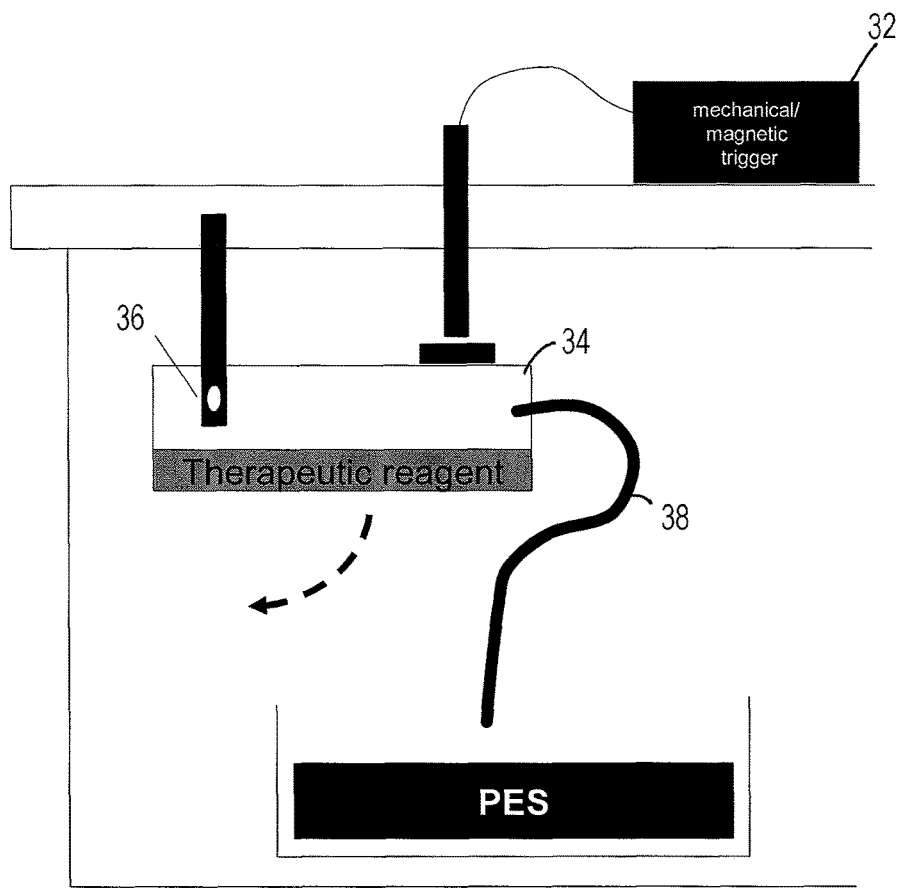
FIG. 9B is an exploded view of a portion of the device in FIG. 9A.

One specific embodiment of the preceding methods is to place the PES device in a vacuum chamber with a container of 100% ethanol, reduce the pressure in the chamber to a value generally below the vapor pressure of ethanol (e.g. <44 torr at 20° C.), close off the chamber, then allow exchange of ethanol vapor with air in the PES coating for a period ranging from about 1 minute to about several days or more, depending on the PES coating thickness. The PES device is then introduced into a solution of 100% ethanol containing a therapeutic agent, such as rapamycin (sirolimus), at either subatmospheric, ambient, or supra atmospheric pressure. In the case of non-ambient pressure loading, the preceding method may be performed using equipment that allows remote control introduction of the PES device into the loading solution, as shown in FIGS. 9A and 9B. In another embodiment, the vacuum chamber is brought to ambient pressure and the PES device is introduced manually into the loading solvent containing the therapeutic agent and to then proceed with subsequent loading processes as described elsewhere in this application.

An additional method which is a modification of the preceding is to load in one solvent as described, and to then remove the device and place in a second solvent with lower solubility for the therapeutic agent (with or without vacuum) thereby promoting selective precipitation of the therapeutic agent both on and within the nanoporous coating. This method has the unique advantage of providing a "loading gain factor"—that is deposition of a greater dosage of therapeutic agent than calculated based on the free volume within the coating times the concentration of the therapeutic agent.

One embodiment of this method is to load rapamycin within 100% ethanol at its maximum solubility of approximately 90 mg/ml and 50-60 torr pressure, to remove the device from the ethanol loading solution, and to immediately place it in a solvent that has much lower rapamycin solubility (e.g. 20% ethanol or physiological saline) with or without vacuum. The net result is precipitation of rapamycin within and on the inner surfaces of the nanoporous coating as well as at the interface of the solvents and on the surface of the coating. Examples of second solvents include 0.01%-100% ethanol (depending on desired dosage), water, phosphate buffered saline or other aqueous solution with or without rapamycin to provide controlled washing and deposition of therapeutic agent on the surface of the biomedical device as well as precipitation of the therapeutic agent within the coating.

An additional modification of the preceding methods is to precede loading steps by replacing the gas within the nanoporous coating with one that has a higher solubility in the loading solvent than does air. For example, one embodiment for loading a hydrophilic drug like Gleevec would be to carry out loading in an atmosphere of $CO_2$ which has a >20 fold greater solubility in aqueous solutions as compared to air. Similarly, use of $CO_2$ would also facilitate removal of trapped gas and loading of hydrophobic drugs like rapamycin in solvents such as ethanol, methanol, and acetone.

In a preferred embodiment, the gas within the nanoporous coating may also be displaced or replaced with the vapor form of the loading solvent or similar substance that is miscible with the loading solvent. By condensing the vapor form of the loading solvent into liquid form, mixing of the condensed vapor with the loading solvent can occur without concern as to the solubility between the gaseous material and loading solvent. Condensation of the vapor form of the solvent may occur separately by active or passive cooling of the loading environment, or during the filling of the interstitial space by the solvent. The vapor form of the solvent may condense as it contacts the cooler liquid form of the loading solvent.

A further modification of the preceding methods is to subject the coated biomedical device to positive pressures during the loading process or to cycle between vacuum pressures and positive pressures. One embodiment would be to perform and initial loading step for rapamycin in 100% ethanol at 60 torr, followed by application of a pressure greater than atmospheric pressure to force loading solution (or precipitating solution) deeper into the nanoporous coating.

A further embodiment of the invention involves evacuating the air from the PES of the biomedical device by placing it in a vacuum for a period of time prior to exposure to loading solvent containing the therapeutic agent. In this case the pressure in the PES is subatmospheric. One can then immerse the device into loading solution within the vacuum system and then bring the pressure to atmospheric or greater to enhance the loading process deep into the coating and pores due to the higher ambient pressure than that present within the trapped gas or air in the pores. One embodiment of a loading device for this process is illustrated in FIGS. 9A and 9B.

Another loading method involves repeat loading and drying steps using combinations of the disclosed methods. For example, one embodiment includes loading the PES with saturated or supersaturated solutions of rapamycin or its analogs in 100% ethanol at 50-60 torr following by air drying (or vacuum drying) between repeat loading steps. One can also vary the loading times and/or temperature, as well as the washing or processing steps between loadings. Finally, one can alternate between vacuum loading and positive pressure loadings and use of solvents with high and low rapamycin solubilities.

It is advantageous, but not necessary, to use saturated or preferably supersaturated loading solutions (e.g. made by adding a defined amount of additional solid therapeutic agent to a saturated solution) to avoid removal of the therapeutic agent or agents deposited in previous loading steps. Use of these methods can result in increased loading of the agent. This increase can be several multiples of the theoretical drug loading achieved by traditional loading methods, as a calculated by the PES porous volume multiplied by the concentration of the therapeutic agent or agents in a saturated or supersaturated solution. More specifically, the drug concentration or drug loading of the PES porous layer may be calculated by the following equation:

$$\text{drug concentration}\left(\frac{ng}{mm^2}\right) = \frac{A\% \text{ void fraction}}{100} \times B\,\mu\text{m layer thickness} \times C_{max}mM \text{ solution} \times \frac{D_{MW}}{10^3}$$

where A % is the average void fraction of the PES porous layer and B is the average thickness of the PES porous layer in micrometers, C is the maximum concentration of the therapeutic agent in solution and D is the molecular weight of the therapeutic agent. In some embodiments of the invention, a loading multiplier of at least about 5 times the theoretical limit is achieved. Sometimes, at least about 10 times to about 25 times the theoretical drug concentration is obtained. In still other embodiments, a drug concentration of at least about 50 times or about 100 times the theoretical limit is achieved by the methods described herein. For example, by using ethanol vapor exchange followed by repeated load-dry steps (with alternating vacuum levels) substantially higher levels of rapamycin concentrations can be achieved in a porous stent. In still other embodiments, crystalline rapamycin may be deposited into the porous zone or formed in the porous zone, providing a concentration of at least about 1000 times to about 2000 times or higher than the theoretical limit of rapamycin as calculated by the above equation.

An additional challenge for loading therapeutic agents using solvents is selective removal of solvents and/or residual materials other than the therapeutic agent upon completion of loading. In one embodiment of the current invention, this process is accomplished by one or more of following procedures including but not limited to air drying at ambient pressure, drying at subatmospheric pressure, increasing the temperature of the system, use of chemical desiccants selective for the solvents in question, and exposure to inert gases that can promote drying or neutralization of residual materials and solvents.

The preceding methods are not intended to be exhaustive but rather illustrate just a few specific examples of the general loading principles that can be employed to facilitate the loading and processing steps for deposition of therapeutic agents within nanoporous coatings of many types and varieties.

An additional consideration in loading and processing nanoporous coatings for controlled delivery of therapeutic agents involves steps to control the surface and subsurface deposition of therapeutic agent. Processing steps may include batch washing in solvents with known solubilities for the therapeutic agent. Indeed one can calculate the exact volume of "wash" solvent to use to remove a precise amount of therapeutic agent from the biomedical device (i.e. this is a function of the solubility, total payload of therapeutic agent deposited during the loading steps), and volume of the batch washing solutions). For example, one may employ a solvent with very low solubility for the therapeutic agent to minimize removal of surface agent if one wishes to optimize the total payload of therapeutic agent. However, in other cases, one may wish to reduce the "burst" release of therapeutic agent on the surface, and/or load a second therapeutic agent on the surface of the coating by highly controlled washing with a solvent that selectively removes some surface material thus allowing for more controlled surface deposition of additional therapeutic agents. For example, this may include use of loading solvents for additional therapeutic agents that are relatively insoluble in the first loading solvent or which have a viscosity inconsistent with deep loading.

Additional methods for controlled deposition of therapeutic agents on the surface of the nanoporous coating include batch processing with controlled air streams (including with high velocity air or other gases), and/or controlled mechanical wiping techniques.

The preceding loading and processing methods may be done at point of manufacture or at the site of use of the device. In some cases this may require specialized equipment including but not limited to vacuum and pressure loading and washing devices. Referring back to FIGS. 9A and 9B, one embodiment of a loading device includes remote controlled initiation of solvent loading while the device is under vacuum. The loading device comprises a vacuum chamber 28 attached to a vacuum pump 30, a mechanical or magnetic trigger 32, a reagent housing 34 attached to a hinge 36 and reagent tubing 38. The vacuum pump 30 is preferably a vacuum pump that is able to remove air from the vacuum chamber and one or more programmable elution stents place in the chamber 28. When the magnetic trigger 32 is released, the reagent housing 34 is able to swing down and allow the therapeutic agent 40 to flow through the reagent tubing 38 until sufficient loading of reagent is reached. In another embodiment, the mechanical or magnetic trigger 32 controls a reagent pump that provides flow of therapeutic reagent onto the PES. The PES coated biomedical device may be secured within its container with a simple batch loading device customized based on the properties of the device in question. For example, in the case of stents, they are held on a comb like device consisting of multiple "teeth" made of an inert material inserted into the lumen of the stents and held such that adjacent stents are separated to allow flow of loading solvent. One skilled in the art can provide other configurations, depending on the particular device, therapeutic agent and other factors.

Figure 10:
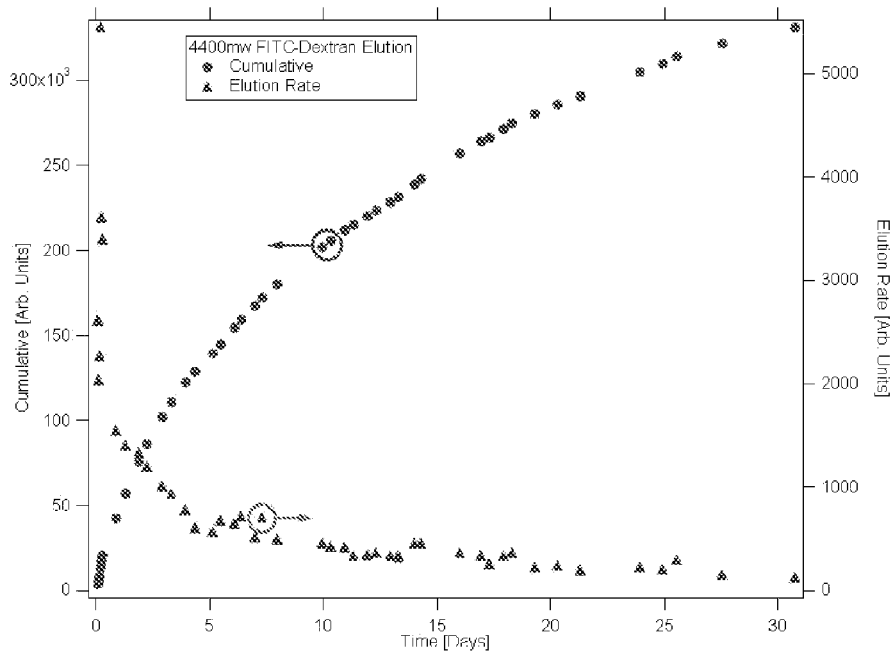
FIG. 10 is graph of the elution rate of one substance loaded into a programmable elution surface (PES).

FIG. 10 depicts one example of the cumulative kinetics and elution rate of a hydrophilic therapeutic substance loaded into a PES. A two-micron thick nanoporous PES on a silicon wafer was loaded with a hydrophilic substance (4400 dalton FITC-dextran) under vacuum conditions for 72 hrs. FITC-dextran was employed for ease of quantitation but mimics release of hydrophilic drugs and other substances. The FITC-dextran loaded PES devices were washed 3 times in phosphate buffered saline (PBS) and placed into 2.0 ml vial for elution. A sample volume was removed daily for measurement of FITC-dextran on a fluorometer (EX 485 nm); an equal volume of PBS was re-added to the vial to maintain a volume of 2.0 ml. Arbitrary Cumulative FITC-dextran release values (left y-axis, blue circles) and Elution Rate values (right y-axis, red triangles) were plotted against time (x-axis, days). The PES continued to release FITC-dextran for at least 30 days.

Figure 11:
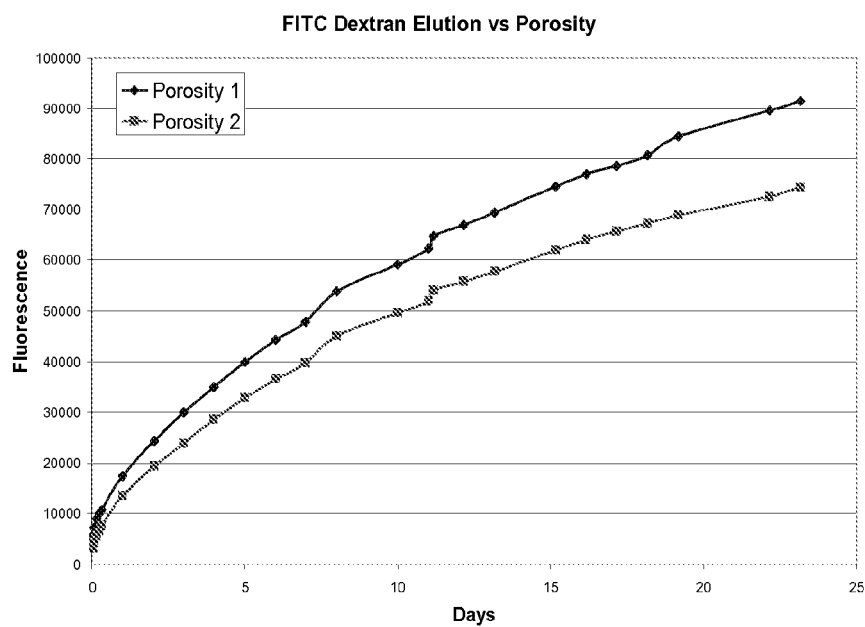
FIG. 11 is a graph of the elution rates of a substance using PES materials of different porosities.

FIG. 11 illustrates the changes in cumulative elution kinetics of a therapeutic substance with changes in porosity of a PES. Two micron thick nanoporous PES of porosity 1 and porosity 2 on a silicon wafer were loaded with FITC-dextran (a hydrophobic reagent, 4400 M.W.) identically to that described in FIG. 10. The relative porosity of sample "porosity 1" (upper curve) was greater than the relative porosity of sample "porosity 2" (lower curve). Increasing the porosity of the PES alters the relative amount of FITC-dextran loaded and released over time. It should be noted that although results shown in FIG. 11 and the following figures describe hydrophilic and hydrophobic drugs and chemical reagents, the storage and release properties illustrated apply to any therapeutic substance.

Figure 12A:
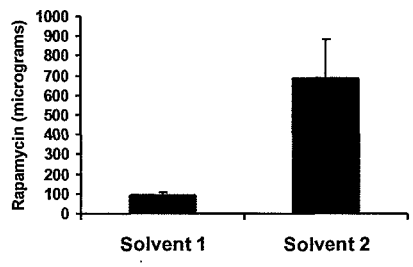
FIGS. 12A and 12B are graphs of the elution rates for a substance using different solvents.
Figure 12B:
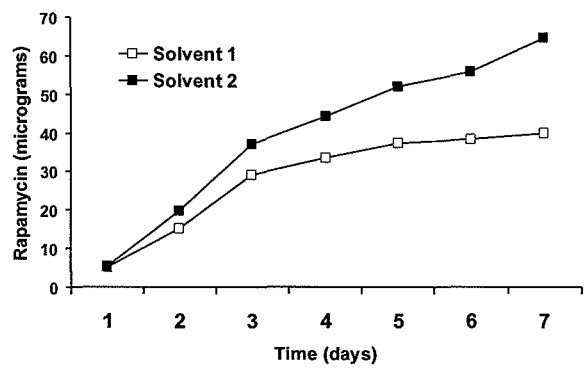

FIGS. 12A and 12B depict the changes to the cumulative elution kinetics of a reagent in the PES by changing the solvent. Two micron nanoporous PESs were loaded with rapamycin (also known as sirolimus, a hydrophobic therapeutic drug or reagent) dissolved in "solvent 1" (open boxes) and "solvent 2" (closed boxes). The PESs were loaded under vacuum conditions for 72 hrs. FIG. 12A represents the total payload in the PES by eluting directly in 2.0 ml of 1-octanol and determining rapamycin concentration by spectrophotometry (absorbance wavelength of 279 nm). FIG. 12B represents cumulative elution kinetics of over 7 days by eluting into a PBS/1-octanol phase separation (a standard in the industry for determining elution rates of a hydrophobic drug).

Figure 13:
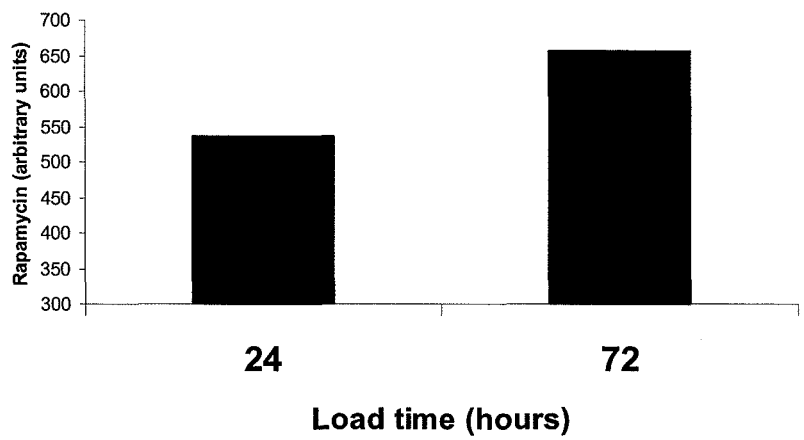
FIG. 13 is a graph depicting loading differences based upon loading time.

FIG. 13 depicts changes in the payload of a reagent in a PES by changing the load time. One micron thick nanoporous PESs were loaded with rapamycin (also known as sirolimus, a hydrophobic therapeutic reagent) under vacuum conditions for 24 and 72 hrs.

Figure 14:
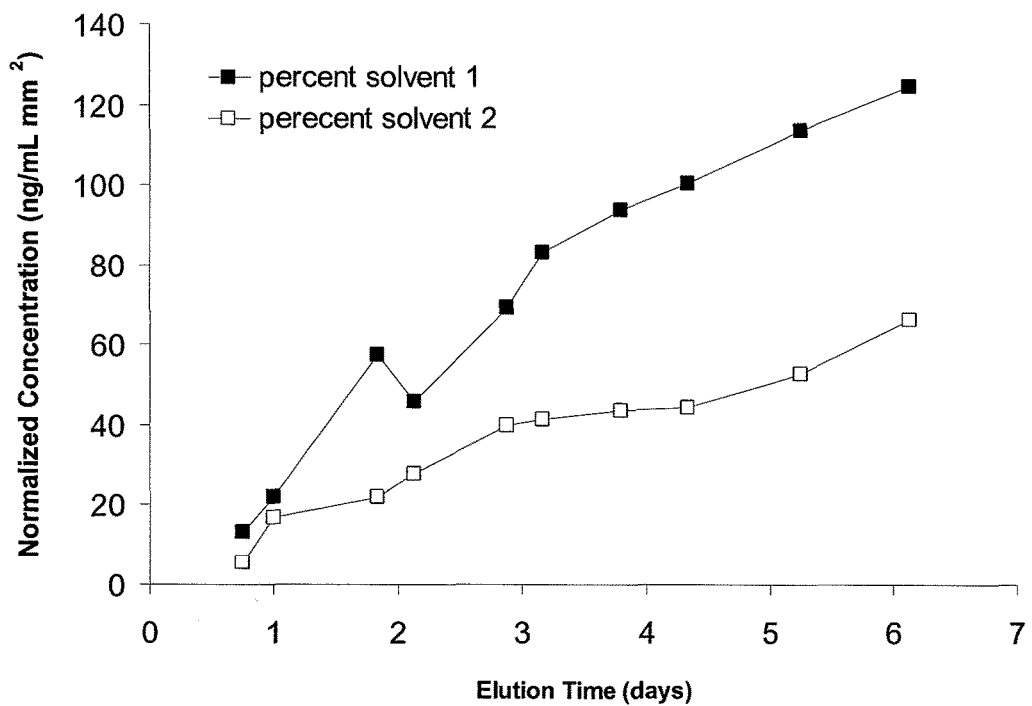
FIG. 14 is a graph illustrating differences in loading based upon solvent washing of the device.

Referring to FIG. 14, a loaded reagent can be selectively removed from the PES by washing the device in various percentages of the original solvent. One micron thick nanoporous PESs were loaded with rapamycin under vacuum pressure for 72 hrs. The PESs were then exposed to "percent 1" (closed boxes) and "percent 2" (open boxes) of the original solvent used to dissolve rapamycin and load the PES for 30 minutes, since the solubility of rapamycin decreases with decreasing percentages of rapamycin.

Figure 15:
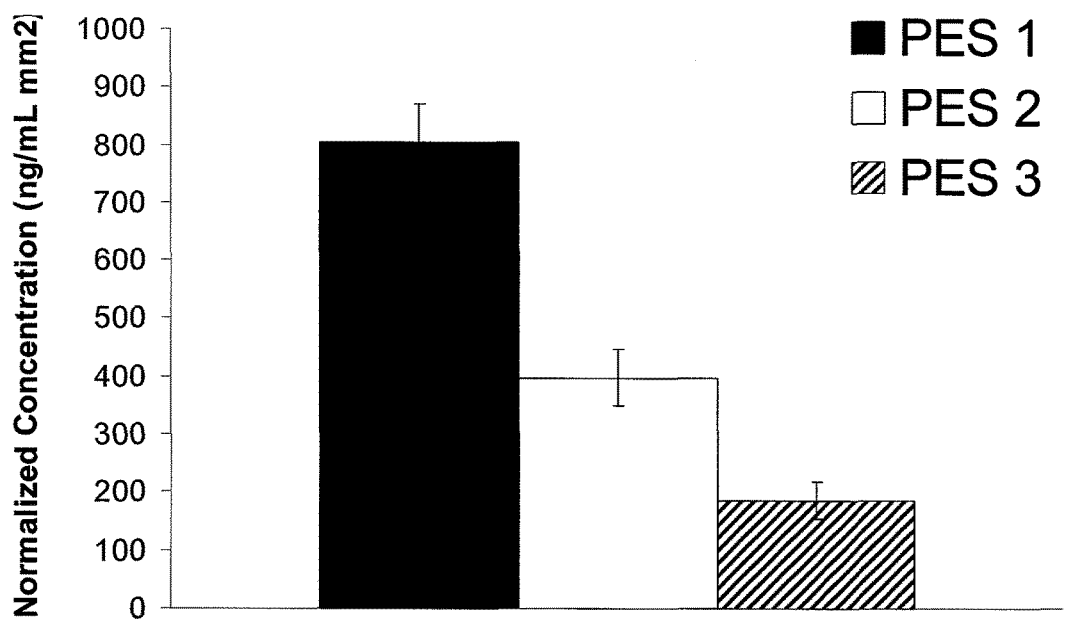
FIG. 15 is a graph showing differences in programmable elution surface loading based upon changes in composition and loading conditions.

FIG. 15 illustrates how changes to the composition and loading conditions for the PES alters reagent payload. One micron thick nanoporous PESs were loaded with repeat vacuum loading, drying, and washing steps with rapamycin and payload determinations made as described in FIG. 12. Results demonstrate the capacity to alter drug loading payloads with a combination of changes in PES and loading methods.

I. Other Effects of Nanoporous Layers

Figure 17:
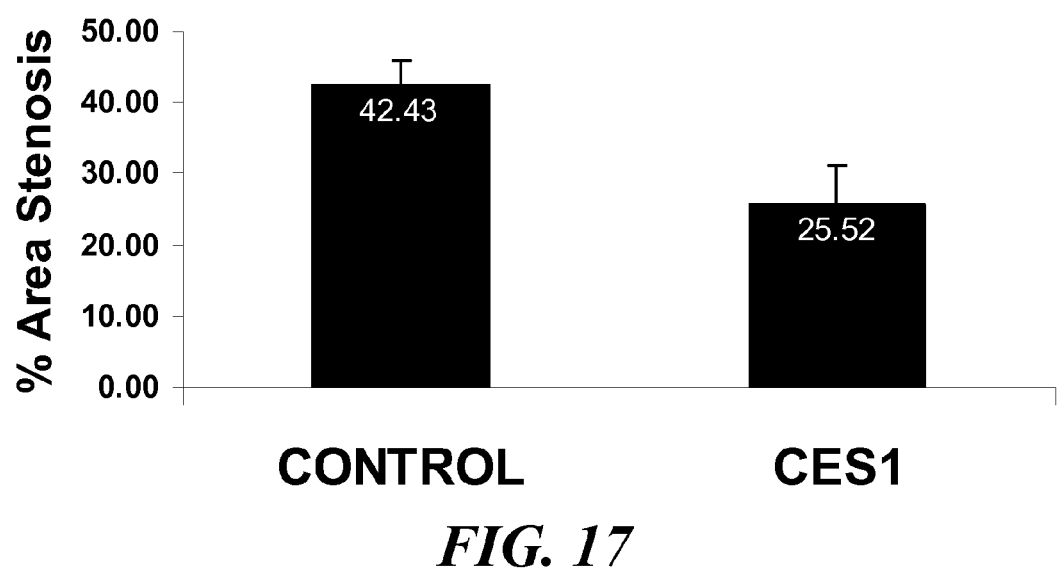
FIG. 17 is a graph showing 90-day stenosis rates between a commercially available stent and a porous coated stent that does not include an eluted therapeutic agent.
Figure 29:
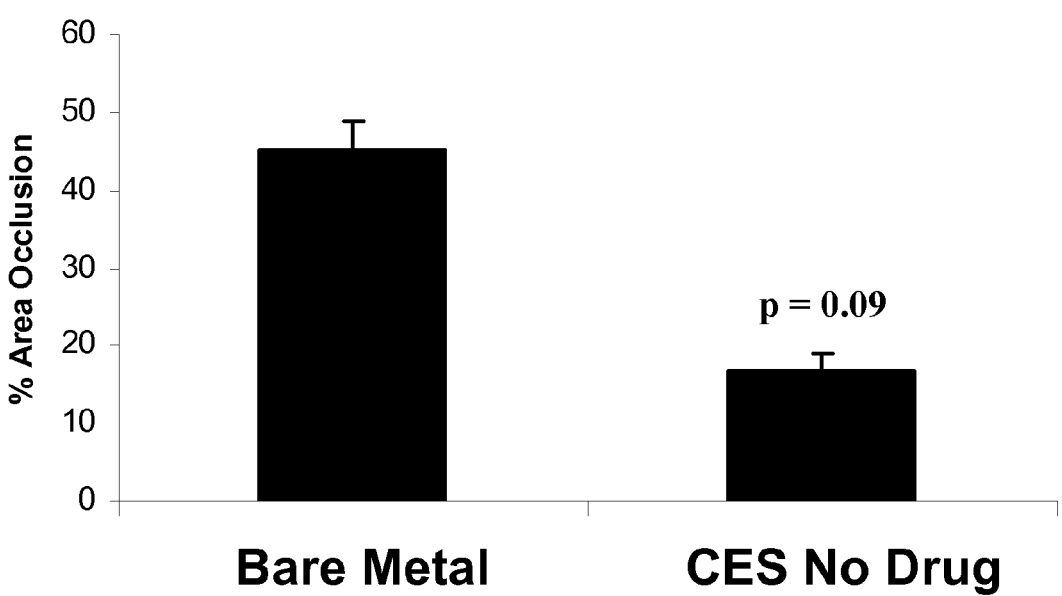
FIG. 29 is a graph showing 90-day stenosis rates between a commercially available bare metal stent and a stent with a nanoporous surface that does not include an eluted therapeutic agent as in FIG. 17, but excluding one control and two nanoporous stents placed in coronary arteries of one pig that exhibited systemic inflammation and judged to be an outlier by the histopathologist.

As mentioned previously, some embodiments of the invention relate to methods of treatment using a porous coating that do not require a therapy-eluting component, such as tissue ingrowth or removal of various agents through adsorption or absorption. Other non-therapy eluting uses for porous stents are also contemplated within the scope of the invention. For example, the inventors have discovered that the use of a stent with a porous coating alone may have an effect on reducing stenosis or cellular proliferation in a vascular lumen. In one study performed by the inventors, a commercially available base metal stent (VISION®) stent by Guidant, Inc., IN) was compared to the same stent coated with a dealloyed porous coating of the disclosed invention to evaluate vessel stenosis over a 90-day period. Referring to FIG. 17, the results of the study showed that the control base metal stents exhibited a lumen stenosis of about 42% while the treated stents exhibited only a lumen stenosis of about 25%. The study was performed in Yucatan miniswine pigs of ages 12 to 16 weeks and weighing 25 to 45 kilograms. Anesthesia was induced in each pig. A 7F catheter was inserted and the coronary anatomy was visualized. A stent diameter was selected based upon the visual estimate of the target vessel diameter to achieve about 10 to 20% oversizing. Each subject received up to three stents in the Left Anterior Descending Artery, Left Circumflex Artery or Right Coronary Artery, depending on the suitability of the coronary anatomy. The subjects were treated with clopidogrel for 28 days post-operatively and aspirin throughout the study period. At the end of the study period, the subject was anesthetized and recatheterized with a 7F catheter and coronary angiography was performed again. The subject was then euthanized and the heart was removed for histopathological and quantitative morphometric analysis. FIG. 29 reports the results of the same study, but excludes one pig from the analysis which exhibited systemic inflammation.

Figure 24:
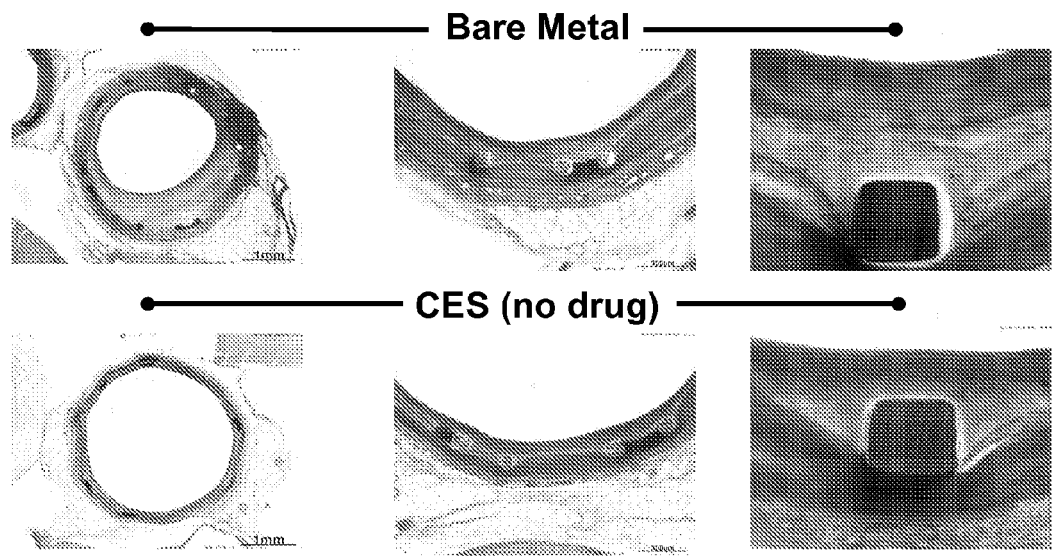
FIG. 24 is collection of comparative histopathology cross sections demonstrating the degree of neointimal formation associated with a bare metal stent and a stent with a nanoporous surface.
Figure 25:
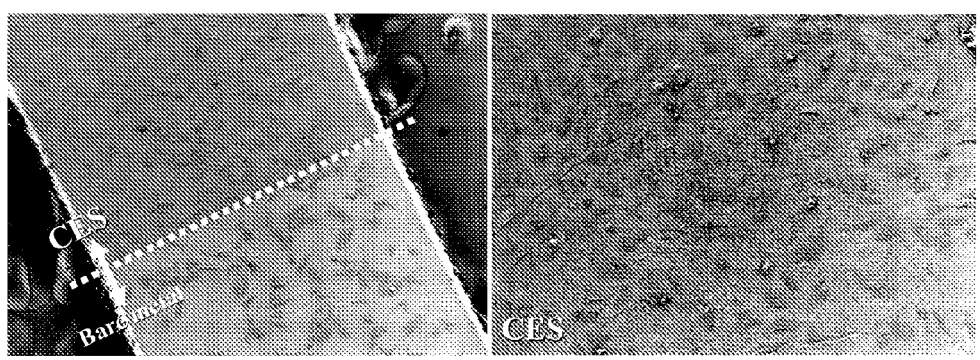
FIG. 25 is a set of scanning electron-micrographs illustrating the re-endothelialization associated with a nanoporous surface.

Referring to FIG. 24, comparative histology cross-sections demonstrated improved biocompatibility of the Controllable Elution System (CES) stent, with reduced vascular stenosis and reduced neointimal proliferation as compared to the bare metal stent. These findings are further supported by in vitro studies, depicted in FIG. 25, that show enhanced adherence and growth of cultured human endothelial cells with the CES layer as compared to bare metal. Thus, there is preliminary evidence that the Setagon CES, even without a therapeutic agent loaded, has improved long term biocompatibility and safety compared to bare metal stents.

The reduced stenosis by the porous stent may be due to a number of etiologies, including improved biocompatibility and tissue healing. The mere presence of a bare metal stent that lacks pores or configured surface structures in a vascular lumen may result in slippage, friction, fragmentation of cell-matrix-stent adhesions, and chronic irritation to the tissue surrounding the bare metal stent. These effects may be worsened by the repetitive mechanical deformation of the blood vessel during cardiac contraction and relaxation. Such effects and interactions may be reduced with stents comprising a porous coating. Studies by the inventors have shown that endothelial cells and smooth muscle cells have improved adhesion to porous coatings compared to bare metal surfaces. A porous coating may provide increased adhesion of cells and extracellular matrix components to the stent as compared to a bare metal stent, which in turn promotes healing and/or reducing chronic irritation/inflammation. A porous coated stent may also improve the anchoring of the stent in the vascular lumen, which reduces the mechanical forces generated at the interface between the stent and surrounding tissue. Reduction of mechanical force at the stent-tissue interface may also result in neuro-hormonal and autocrine/paracrine effects that alter the tissue response to stent implantation. A porous stent may be used alone or in combination with a therapy-eluting component to further modulate these changes. In some embodiments, a nanoporous stent adapted to provide increased adhesion of cells and extracellular matrix components to the stent as compared to a bare metal stent, which in turn promotes healing and/or reducing chronic irritation/inflammation may have a pore size of about 0.1 nm to about 500 nm, preferably about 1 nm to about 500 nm, and more preferably about 1 nm to about 50 nm. In another embodiment, the pore size is about 20 nm to about 200 nm. Although not wishing to be bound by this theory, it is believed that in the embodiments described above, the pore range is below that which is known to elicit adverse cellular responses including activation of platelets, or immune cells as described by Park et al. Biomaterials 22:2671, 2001 and Edelman et al. *Circulation* 103 (3): 429.

An alternative or complementary mechanism that may be affect stenosis rates with porous stents is the elution or leaching of metals contained in the dealloyed coating. The metals used in the porous coating may be affecting endothelial and smooth muscle cells, or may be altering inflammatory or immunological pathways. This elution of metal may also be enhanced by the increased surface area of the dealloyed coating compared to a bare metal surface. These metals may include those used as structural components in the porous matrix, as well as remnants of those used as a sacrificial material to form the pores or impurities from the manufacturing process. In one example, studies have demonstrated that biodegradable magnesium stents may be associated with significant benefits in maintaining lumen diameter. Heublein et al., Biocorrosion of Magnesium Alloys: A New Principle in Cardiovascular implant technology, 89 *Heart* 651 (2003) and Di Mario et al., Drug-Eluting Bioabsorbable Magnesium Stent 17 *J. Interven. Cardiol.* 391 (2004). The magnesium, in the form of magnesium oxide (a solid, insoluble base), may also be hydrolyzing in vivo and raising the local pH at the vascular lesion, which in turn may suppress cellular proliferation. Local alteration of pH may also be achieved using other solid bases including barium oxide and calcium oxide. Magnesium may be reacting with anions, such as chloride ions present from the dissociation of sodium chloride ions in the bloodstream. The magnesium may be reacting with and reducing the concentrations of these anions that may act as biologically active proliferative agents. Magnesium acts as a cation in aqueous solutions, which suggests that other cations may exhibit a similar effect, such as Be, Ca, Sr, Ba, Ra, Li, Na, K, Rb, Cs, and Fr. Other metals that may be used with the invention to affect vascular stenosis include cobalt, chromium, silver, gold, titanium, zinc, aluminum, manganese, tantalum, vanadium, and platinum.

J. Materials and Methods for Producing Devices with Nanoporous Features

In one embodiment of the invention, a vascular stent with a porous coating is provided for insertion into a vascular lumen to resist vascular stenosis. The stent may comprise a material such as magnesium, cobalt-chromium, L605 or other cobalt-chromium alloy, 316L stainless steel, silver, gold, titanium, nickel, tantalum, vanadium, platinum, tungsten, nitinol, or alloys/combination thereof. The stent may have a diameter in the range of about 2.0 mm to about 15 mm, preferably about 2.5 mm to about 5 mm and more preferably about 2.5 mm to about 3.5 mm. The length of the stent may range from about 5 mm to about 50 mm, preferably about 8 mm to about 40 mm and more preferably about 8 mm to about 32 mm. Prior to deposition of the porous coating, the stent may be processed, cleaned or pretreated using ultrasonic methods and substances such as ethanol, acetone, TCA or TCE, inorganic bases such as sodium hydroxide, ammonium hydroxide, potassium hydroxide; or inorganic acids, such as hydrochloric acid, hydrofluoric acid, sulfuric acid, nitric acid, phosphoric acid In one embodiment, to deposit the porous coating, the stent undergoes DC backsputter at about 15 milli-torr pressure of $Ar+H_2$ and biased to about 1000 V for about 20 minutes. Pressure range for backsputter can be from 2 milli-torr to 100 milli-torr, but preferably between 10 to 20 milli-torr. Biasing can be DC in the range of 100 V to 2000 V, preferably in the range of 800 V to 1200 V. Alternatively, RF backsputtering can also be used, in which case the bias of the stent will be in the range of 100 V to 500V. Back sputter times can be from 1 minute to 120 minutes, but preferably between 10 minutes and 30 minutes. The porous coating may be deposited using a sputter process in a pressure range range of 1-20 milli-torr Ar, preferably 2-15 milli-torr Ar and more preferably 2 milli-torr Ar, and at a wattage of about 100 W to about 1000 W, preferably about 200 W to about 500 W and more preferably about 225 W to about 300 W or 400 W, depending on the material. The sputter material may comprise chromium, L605, magnesium, aluminum, silver, copper, gold, vanadium, platinum, tungsten, titanium, aluminum oxide, silicon carbide, silicon dioxide, or silicon nitride. The sputtering time may range from about 5 minutes to about 60 minutes, preferably about 6 minutes to about 30 minutes or even 60 minutes. There may or may not be a pre-sputtering conditioning period in the range of about 1 minute to about 5 minutes. In one embodiment, the pores of the stent range in size from about 10 nm to about 500 nm, preferably about 15 nm to about 300 nm and more preferably about 20 nm to about 200 nm. After deposition, the stent may be treated with 1% $HNO_3$ at room temperature, and subsequently annealed at 600 C for 10 minutes in vacuum. The concentration of the dealloying solution may vary from 0.1% to 65% $HNO_3$. The temperature of the dealloy solution may range from −5 Celsius to 95 Celsius, but will preferably be in the range of 0 Celsius to 70 Celsius. Alternatively, other acids or bases (organic or inorganic) may also be used to de-alloy the sputter deposited material. These reagents include sodium hydroxide, potassium hydroxide, ammonium hydroxide, phosphoric acid, oxalic acid, hydrochloric acid, hydrofluoric acid, sulfuric acid. Annealing temperatures may vary from 200 C to 1200 C, but will preferably be in the range of 500 C to 800 C. Annealing ambient may be vacuum or a low pressure gas, such as Ar, Ne, $N_2$, $O_2$, $H_2$, Xe, or combination thereof. The pressure of the gas during anneal may be in the range of 1 milli-torr to 100 milli-torr, but will preferably be in the range of 5 to 20 milli-torr. The porous coating may have an interpore spacing between 1 and 20 times the size of the pores, preferably about 1 to 10 times the size of the pores and more preferably about 1 to 5 times the size of the pores. After processing or cleaning, the stent may be dried using $N_2$ or other gases. The stent may or may not have a therapy-eluting component. The therapy-eluting component, if any, may be integral with the porous coating. The porous coating need not be completely filled with therapy-eluting component to its outer surface. By providing at least a portion of the porous coating with open pores, the porous coating may be adapted to reduce surrounding cellular proliferation and/or vascular stenosis.

The performance of these and other non-eluting features of the invention, either alone or in combination with other eluting and non-eluting characteristics of the invention may be determined or optimized with routine experimentation by those of ordinary skill in the art. Stent characteristics related to porosity, directionality and/or configuration of the pores, material composition, method of delivery, self-expandability, balloon expandability, strut arrangement, length, thickness and diameter may be manipulated and still be contemplated within the scope of the invention. Although dealloyed porous stents are disclosed as non-limiting examples of the invention, other types of porous stents or medical devices and non-porous stents that exhibit stenosis resistant properties are also contemplated.

In addition to coronary stents, other embodiments of the invention contemplate the use of dealloyed and/or porous coatings with other medical devices, including but not limited to peripheral stents, biliary stents, cerebrovascular stents, vascular grafts, orthopedic fixation devices such as plates and screws, implantable pacing leads and sensors, pacemaker and defibrillator housings, and others.

Although localized drug-eluting technologies such as drug eluting stents have been used to provide greater tissue concentrations of therapeutic agent compared to systemic administration of a therapeutic agent, the features of a dealloyed nanoporous stent may allow even higher tissue concentrations of therapeutic agent than those provided by existing technologies. In one embodiment, the use of rapamycin with a dealloyed nanoporous stent is capable of achieving tissue concentrations from 0.01 to 2 ng/mg tissue, or about 2 ng/mg of tissue to more than about 2000 ng/mg of tissue, based upon 7-day in-vivo values. In other embodiments, a dealloyed nanoporous stent is capable of achieving rapamycin tissue concentrations from about 5 ng/mg of tissue to more than about 1000 ng/mg of tissue, based upon 7-day in-vivo values, and in some instances, is capable of achieving rapamycin tissue concentrations from about 3 ng/mg of tissue to about 100 ng/mg of tissue, based upon 7-day in-vivo values, and in other instances is can achieve rapamycin tissue concentrations from about 2 ng/mg of tissue to about 500 ng/mg of tissue, based upon 7-day in-vivo values. In still another embodiment, a dealloyed nanoporous stent is prepared and loaded to achieve a rapamycin tissue concentration from about 175 ng/mg of tissue to more than about 500 ng/mg of tissue, based upon 7-day in-vivo values. The dealloying process can provide the ability to control the localized delivery of a therapeutic agent using a morphologically scaleable technology.

EXAMPLE A

Figure 18:
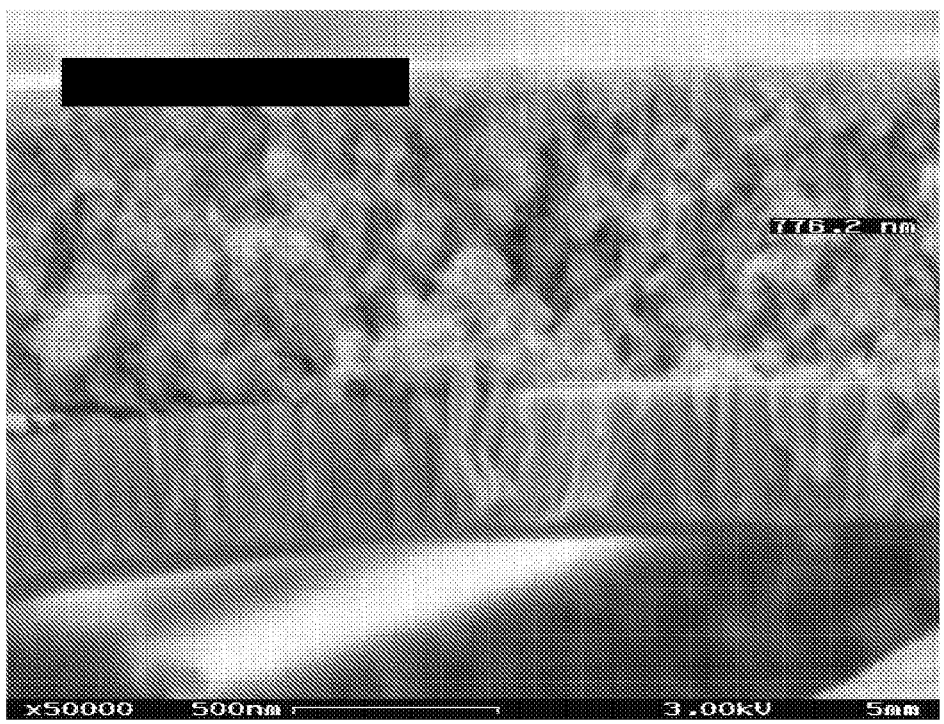
FIG. 18 is another scanning electron micrograph of another embodiment of the invention comprising a dealloyed coating.

In one specific example, a coronary stent is co-sputtered with L605 (3.1 A/s) and magnesium (9.7 A/s) in 2×10-3 torr Argon, resulting in an alloy coating that is approximately 30% by weight of magnesium. The stent is dealloyed using a 1% $HNO_3$ at about 1° Celsius for about 5 minutes, followed by an anneal at about 600° Celsius for 10 minutes at about $10^{-5}$ torr vacuum with a ramp rate of about 200° Celsius/minute. This process produces a dealloyed layer as depicted in the scanning electron micrograph in FIG. 18. The resulting porous zone is approximately 3% by weight of magnesium and has a range of pore sizes from about 1 nm to about 25 nm.

In a further embodiment, the stent may be loaded with rapamycin using a procedure whereby the stent is washed using absolute ethanol in a gently agitation of about 40 rpm for about 1 hour. The stent is then placed in a vacuum chamber along with a 7"×5" reservoir of about 100 mL of absolute ethanol. The vacuum pump is set to a setting of about 1 torr and run for about 15 minutes. The chamber is then sealed, the pump is stopped, and the ethanol vapor from the reservoir is allowed to fill the chamber for 30 minutes. The chamber is vented to atmospheric pressure over about 5 minutes and then opened so that about 30 mL of absolute ethanol is applied to a container holding the stent and the ethanol reservoir is refilled. The vacuum pump is set for about 60 torr and run for about 3 hours, then stopped and the chamber is slowly vented to atmospheric pressure over about 5 minutes. The stent is removed from the vacuum chamber and sprayed with compressed air to remove the excess ethanol and placed in another vacuum chamber to air dry for 15 minutes. The vacuum pump is set to about 1 torr and run for 20 minutes to dry the ethanol from the stent, followed by stopping the pump and venting the chamber to atmospheric pressure over about 2 minutes. This step is then repeated, at least one and preferably two or more times before the stent is removed from the drying vacuum chamber. The stent is placed in another vacuum chamber with a reservoir of about 100 mL absolute ethanol and the vacuum pump is run for about 15 minutes at about 1 torr before stopping the pump and allowing ethanol vapor to fill the vacuum chamber for about 2 hours before venting the chamber to atmospheric pressure over about 5 minutes. About 10 mg of dry rapamycin power is then sprinkled into a container and about 10 mL of a 90 mg/mL rapamycin loading solution in absolute ethanol is provided to the dry rapamycin in the container and the stent is submerged into the loading solution. This step is to ensure supersaturation of the loading solvent with rapamycin. The container with the stent and loading solution is placed in a vacuum chamber with another ethanol reservoir and the vacuum pump is run for about 3 hours at about 60 torr before stopping the pump and venting the chamber to atmospheric pressure over about 5 minutes. The stent is removed from the container and sprayed with compressed air to remove excess loading solution and then placed in another vacuum chamber to air dry for about 15 minutes. The vacuum pump is run for about 20 minutes at about 1 torr to dry the ethanol from the stent and then the pump is stopped and the chamber is vented to atmospheric pressure over about 2 minutes. The vacuum drying is repeated at least once and at least preferably twice more before removing the stent from the drying vacuum chamber. The loading procedure then repeated at least once more and preferably two or three times or more but without the dry rapamycin powder before undergoing ultra high vacuum (UHV) drying to remove residual solvent from the stent. This procedure typically results in an initial stent payload of about 80-100 micrograms of rapamycin on a 12 mm (length) by 3.5 mm stent. Placed in an in vivo porcine coronary artery stent model, the stent provides a 7 day tissue concentration of about 1.00 ng/mg of tissue as measured by tandem MS/MS HPLC.

EXAMPLE B

Figure 19:
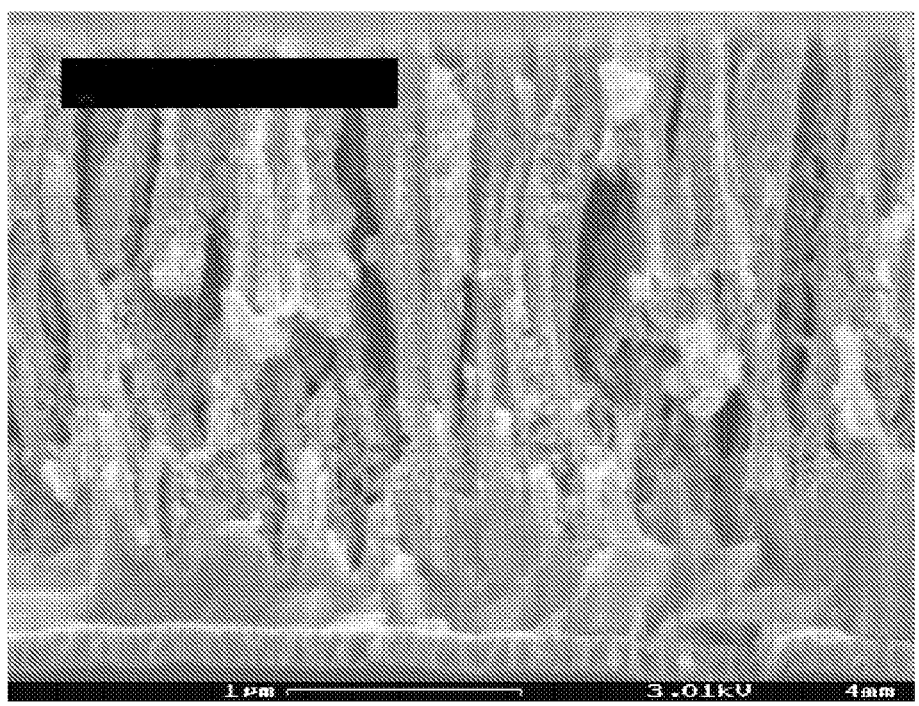
FIG. 19 is another scanning electron micrograph of another embodiment of the invention comprising a dealloyed coating.

In another specific example, a coronary stent is co-sputtered with L605 (1.5 A/s) and magnesium (12 A/s) in $2\times10^{-3}$ torr Argon for a resulting alloy coating that is approximately 80% by weight of magnesium. The stent is dealloyed using a 1% $HNO_3$ at about 1° Celsius for about 5 minutes, followed by an anneal at about 600° Celsius for 10 minutes at about $10^{-5}$ torr vacuum with a ramp rate of about 200° Celsius/minute. This process produces a dealloyed layer as depicted in the scanning electron micrograph in FIG. 19. The resulting porous zone is approximately 5% by weight of magnesium and has a range of pore sizes from about 10 nm to about 200 nm. In a further embodiment, this stent is loaded with rapamycin using the same procedure as disclosed in Example A, resulting in an initial payload of about 85 micrograms. Place in an in vivo porcine coronary artery stent model results in a 7 day tissue concentration of about 0.80 ng/mg of tissue as measured by tandem MS/MS HPLC.

EXAMPLE C

In still another specific example, a coronary stent undergoes a lower layer sputter deposition with L605 (1.5 A/s) and magnesium (12 A/s) in 2×10⁻³ torr Argon, and followed by an additional upper layer co-sputtering with L605 (3.1 A/s) and Mg (9.7 A/s) in 2×10-3 torr Argon, for a resulting alloy coating has a lower layer thickness of about 750 nm and an upper layer with a thickness of about 75 nm.

Figure 20:
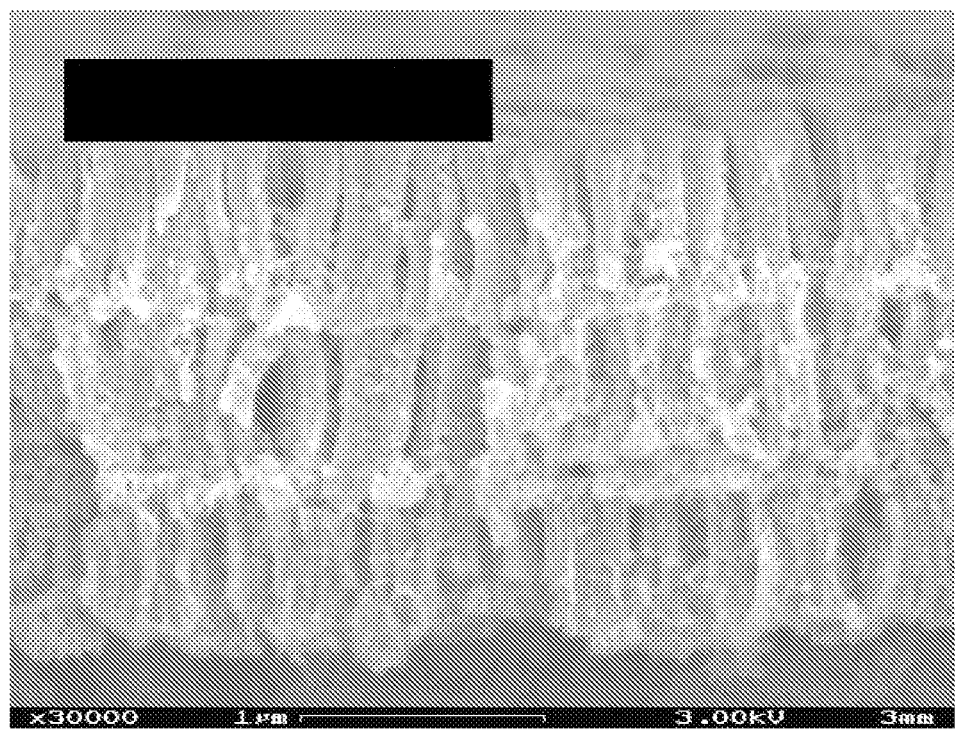
FIG. 20 is another electron micrograph of another embodiment of the invention comprising a dealloyed coating.

Optionally, one or both sputtering steps may be repeated one or more times, in an alternating or other desired order, to create a layered columnar porous zone. In one embodiment, shown in FIG. 20, an additional two high magnesium content layers, with one lower magnesium content layer is sputtered to produce a five layer porous stent surface. The stent is dealloyed using a 1% HNO$_3$ at about 1° Celsius for about 5 minutes, followed by an anneal at about 600° Celsius for 10 minutes at about 10$^{-5}$ torr vacuum with a ramp rate of about 200° Celsius/minute. The resulting porous zone has a range of pore sizes from about 1 nm to about 200 nm.

The resulting porous zone is approximately about 5% to about 10% by weight of magnesium and has a range of pore sizes from about 10 nm to about 200 nm. In one further embodiment, this stent is loaded with rapamycin using the procedure disclosed in Example A, resulting in an initial payload of about 90 micrograms. Place in an in vivo porcine coronary artery stent model results in a 7 day tissue concentration of about 1.70 ng/mg of tissue as measured by tandem MS/MS HPLC.

EXAMPLE D

Figure 21A:
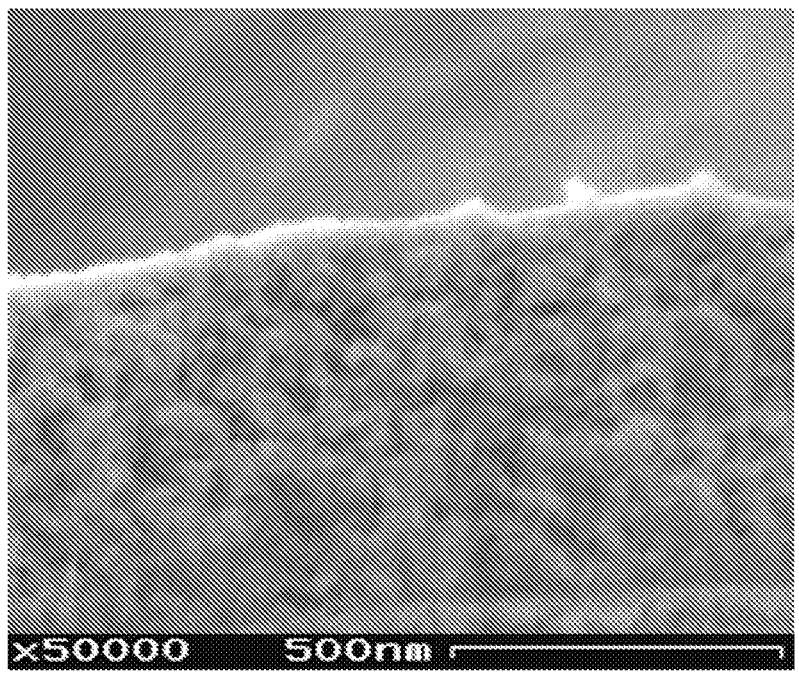
FIGS. 21A and 21B are electron micrographs of another embodiment of the invention comprising a dealloyed coating.
Figure 21B:
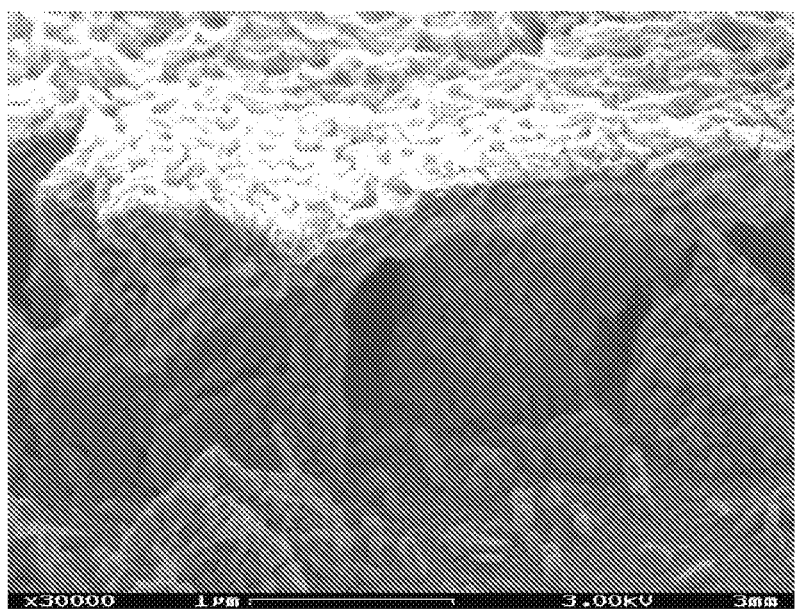

In still example, a coronary stent undergoes a lower layer sputter deposition with L605 (3.1 A/s) and magnesium (9.7 A/s) in 2×10-3 torr Argon, for a resulting alloy coating with about 30% magnesium content by weight. The stent undergoes thermal dealloying by heating the porous zone with a heat source at about 600° Celsius for 10 minutes at about 10$^{-5}$ torr vacuum with a ramp rate of about 200° Celsius/minute. The resulting porous zone is about 10-15% by weight of magnesium with a pore size range of about 1 nm to about 25 nm, but with occasional larger spaces up to about 500 nm or more, as depicted in FIGS. 21A and 21B. Although not wishing to be bound by the theory, it is hypothesized that the different macroscopic morphologies as illustrated in FIGS. 21A and 21B may result from different intrinsic film strains prior to the thermal dealloy process. In one further embodiment, the stent is loaded with rapamycin using an alternative loading procedure as described in Example A, but where the stent not sprayed with compressed air to remove excess ethanol or loading solution except after the final drug loading step. For each loading step, however, after the rapamycin loading solution is provided, the container holding the stent is placed into a −20° C. environment with a vacuum chamber and the vacuum pump is run for about 60 hours at about 20 torr. The pump is stopped and the chamber is vented to atmospheric pressure over about 5 minutes before the stent is removed and dried with absorbent sheet material before insertion into a drying vacuum chamber to air dry for about 15 minutes. The pump in the drying vacuum chamber is then run for about 20 minutes at about 1 torr to dry the ethanol from the stent and then the pump is stopped and the chamber is vented to atmospheric pressure over about 2 minutes. The drying step is then repeated at least once, and preferably at least twice before the stent is placed in a vacuum dessicator under a moderate vacuum of about 450 torr and brought to room temperature by equilibration to a 4° C. environment for about 5 to about 10 minutes, then a laboratory benchtop for about 10 to about 20 minutes. This stent has a resulting payload of about 180 micrograms and a 7 day tissue concentration of about 5.00 ng/mg of tissue as measured by tandem MS/MS HPLC in an in vivo porcine coronary artery stent model. In a second alternative embodiment, the stent may be loaded using the alternative loading procedure described above except that all the loading steps are conducted at a temperature of about −20° Celsius and the stent is thermally equilibrated during only during the dessication step of the last loading cycle where the stent is placed in a vacuum dessicator under a moderate vacuum of about 450 torr and brought to room temperature by equilibration to a 4° C. environment for about 5 to about 10 minutes, then room temperature for about 10 to about 20 minutes. This alternative procedure results in a stent with a payload of about 670 micrograms and a 7 day tissue concentration of over about 900 ng/mg of tissue as measured by tandem MS/MS HPLC in an in vivo porcine coronary artery stent model.

One of skill in the art will also understand that the various dealloying and loading procedures may be varied using routine experimentation to modify the delivery profile of the coronary stent. For example, the above examples may be further altered by one with skill in the art to produce further variations in pore morphologies by either rotating the stent or the deposition apparatus around the stent, altering the angle of incident of the deposition process, altering the rate of the deposition or the temporal period at which material rate and/or composition of material is changed. Such changes can be used to alter the intrinsic strain and grain structure of the deposited material.

To increase pore size, one would generally increase the amount of sacrificial material within the as deposited coating. For example, increasing the deposition rate of magnesium relative to L605 will produce a high magnesium pre-cursor material. When dealloyed, this material would likely have bigger pores. Similarly, one could reduce the L605 deposition rate to produce a similar result.

While the ratio of magnesium to L605 may be a useful parameter to alter when manipulating pore morphology, the absolute values may also be relevant with respect to the net rate at which the material is deposited. Typically, but not always, materials sputter deposited at high rates tend to be more columnar than materials deposited at lower rates, as the incoming material has less time relax into the ideal denser state.

Deposition rates may also be useful when heat dissipation becomes a limiting factor. In one particular example, if the deposition rates of Mg:L605 are increased to the point where sample heating becomes an issue, the strain introduced into the deposited film may cause spalling and delamination upon dealloying. Further, keeping the ratios of Mg:L605 constant and altering total deposition rate may sometimes yield unusual morphologies if heat is not dissipated in a rapid manner.

In some of the embodiments described previously where a more columnar pore structure is desired, the pressure in the chamber may be increased during the deposition process. This generally would lead to deposited material having a more columnar structure. Consequently, the dealloyed material would also reflect a similar structure.

The dealloying may also be manipulated to alter pore sizes. Generally, if one were to increase the dealloy time, more of the sacrificial material will be removed and consequently the material would have bigger pores. However, in certain material systems (such as L605), the pore structure is typically defined a priori. For example, during the deposition process magnesium may segregate preferentially to grain boundaries and/or into occlusions. These magnesium-rich areas, when dealloyed, become pores or voids. The form and distribution of these magnesium-rich spaces is typically dictated by the deposition conditions described above.

In another embodiment, by altering the thermal processing, by either post chemical anneals and/or direct thermal dealloying, pore size may also be altered. Generally, the longer and/or hotter the thermal process, the more magnesium is driven off, resulting in larger pores. Various combinations of chemical and thermal processing, as well the use a reactive gas or reactive plasma previously mentioned, may also be used to further alter pore size.

Furthermore, a lesser or greater amount of therapeutic agent may be loaded into the porous zone by varying the loading procedures disclosed above. In some embodiments, the stent may be loaded with about 50 micrograms to about 2,000 micrograms of therapeutic agent, preferably about 70 micrograms to about 1,000 micrograms of therapeutic agent, and most preferably about 100 micrograms to about 800 micrograms of therapeutic agent. The increased payload may be achieved by altering the rapamycin concentration of the loading solution.

Although the specific examples disclosed above describe the application of an alloy coating onto an existing coronary stent to produce the dealloyed nanoporous zone, as mentioned previously, in other embodiments the alloy materials may be integrally formed with the stent rather than co-sputtered. Also, although the specific examples provided above utilize rapamycin, other therapeutic agents, alone or in conjunction with other therapeutic agents, may be loaded onto a stent or medical device through routine experimentation by one with ordinary skill in the art.

In one embodiment of the invention, a medical device comprising a porous zone further comprises a hydrophobic material deposited onto at least a portion of the porous surface of the porous zone. Because porous metal systems are typically hydrophilic in nature and water has a very small contact angle with these materials, metallic pore structures tend to wet readily. For example, a drop of water applied to a PES surface will be wicked up and spread out by capillary forces. This wetting may have an undesirable effect of increasing the salvation rate of therapeutic agents retained in these porous zones and may result in a more rapid release of drug from the porous zone than is desired. Although not wishing to be bound by the hypothesis, it is believed the presence of a hydrophobic material or coating on at least a portion of the PES will delay the incursion of water into the PES and possibly retard the release kinetics of the therapeutic agent or agents from the PES. The hydrophobic materials that may be deposited include but are not limited to fluorocarbons (e.g. PFE or PTFE), silicon nitride, silicon carbide, nickel nitride, chromium nitride, aluminum oxide, and aluminum nitride. The hydrophobic materials may be used as a final coat, and/or embedded during the pre-cursor deposition phase.

Alternatively, increased hydrophobic behavior may be achieved by subjecting the dealloyed PES to an anneal process that would alter the chemical composition of at least a portion of the pore surface of the PES. One example of this would be nitridizing the surface under a DC plasma in the presence of nitrogen or ammonia. Similar processes, such as RF plasma in the presence of CHF3, may also be used to synthesize hydrophobic material (such as PTFE) onto/into the PES.

In another embodiment of the invention, a nanoporous structure may be applied or formed on at least a portion of a medical device to increase the radio-opacity or echogenicity of the medical device under radiographic visualization, including but not limited to fluoroscopy, CT scanning, plain film X-ray, ultrasound and other visualization modalities. The radio-opacity of medical devices, especially of coronary stents during fluoroscopy, may be important in assisting physicians in optimizing device placement and confirming device location during an invasive procedure or during post-procedure follow-up. Although not wishing to be bound by such a hypothesis, it is believed that the nanoscale structure of the PES coating may enhance the radio-opacity of an implantable device by increasing x-ray scattering. In particular, a nanoporous zone comprising a directional pore structure or columnar filaments may provide a surface configuration for increase x-ray scattering, resulting in reduced x-ray transmission and increased opacity. For example, it has been observed during in-vivo procedures that an L605 PES nanoporous material, similar to that depicted in FIG. 20, appears to be more radio-opaque than a stent coated with gold PES of a similar thickness similar to that shown in FIGS. 7A and 7B. This is a surprising result given that gold has a higher atomic number (79) than tungsten (74), the heaviest component of L605.

As mentioned previously, the roughness of the porous surface may play a role in reducing the inflammatory response induced in the adjacent vascular tissue. Some studies, such as "Gold-Coated NIR Stents in Porcine Coronary Arteries" by Edelman E R et al, Circulation 2001 103: 429-434, herein incorporated by reference in its entirety, have demonstrated that smoothing the surface of a stent by heating it can decrease the $R_t$ and the vivo porcine coronary artery thrombogenicity. In "Platelet interactions with titanium: modulation of platelet activity by surface topography" by Park, J Y et al, Biomaterials 22 (2001) 2671-2682, herein incorporated by reference in its entirety, the authors demonstrated that SEM may be used to calculate optical profilometric data such as $R_a$, average roughness, $R_q$, root mean squared roughness, $R_z$, the average of the 10 greatest peak to valley separations within the sampling area, and $R_t$, peak to valley differences. The data showed that platelet adhesion and activation was generally proportional to Ra, Rq, Rz and Rt. A smaller Rt seems to result in decreased platelet activation and adherence. Although not wishing to be bound by this hypothesis, we hypothesize that a dealloyed porous surface may reduce platelet adhesion and activation by providing a smoother outer surface with a lower Rt or other roughness measure. In general, Rt values less than about 3 microns have been shown to have reduced thrombogenic effect. As mentioned previously, we postulate that embodiments of this invention having a pore size from about 0.1 nm to about 500 nm has unique properties in promoting tissue healing, improved cell adherence and anchoring, and may be provided alone or with a reduced porous zone surface roughness to also decrease platelet activation and adherence. A structure with these characteristics, through dealloying or other porosity means, may be beneficial in reducing the risks associated with implantation of medical devices, especially bare stents or drug eluting stents. That is, one can achieve the benefits of improved cell adhesion and healing without risks associated with activation of platelets or inflammatory cells.

J. Nanoporous Bonding Layers

In addition, the porous layer may provide a means to better anchor these materials to the surface of the stent or other biomedical devices thereby overcoming a major current limitation in these technologies of separation or delamination as illustrated in FIGS. 1 and 2. The risk of delamination of the polymer coating from the stent or other medical device is reduced by the mechanical interfit which occurs as a result of the polymer flowing into the tortuous porous interface and then polymerizing or otherwise hardening in place. This results in a large number of independent interlocking points, distributed throughout the interface between the polymer and the porous surface (i.e. rooting of the polymer to the metallic device).

The pore size and pore geometry may be optimized with each specific polymer, taking into account the viscosity or flowability of the polymer or polymer precursors during the manufacturing process. Manufacturing conditions should be selected so that at least some polymer flows into the pores to provide the interlocking interface following hardening. The pore size may be larger (e.g., micropores) for the bonding function than for direct drug containment as disclosed elsewhere herein. In general, a selective dissolution or dealloying process is one method for producing tortuous, non-linear or angular pores in the surface of a stent or medical device. Furthermore, the pores resulting from a dealloying process can have an interconnecting relationship. Such pores can provide a mechanical interfit between a bonding surface and an elution coating that traditional surface treatments such as acid and laser etching and mechanical roughening do not provide.

The enhanced bonding aspect of the present invention may additionally involve the use of a tie layer between the outer polymer layer and the surface of the medical device. For example, a porous stent may be provided with a first layer of a first polymer or other bonding media which has characteristics that produce a good mechanical interfit with the porous surface. A second layer may thereafter be bonded to the first layer to produce the coated medical device. The second layer is the functional layer, such as a drug delivery layer. In this configuration, the second layer may be optimized for its drug delivery or other function, without regard for whether it can bond effectively to the material or surface structure of the porous substrate.

The tie layer may comprise any of a variety of materials which can be caused to flow into the pores, and is bondable to the functional layer. Thermoplastic materials such various densities of polyethylene can be heated to a flowable state, applied to the porous layer and then cooled to provide the tie layer. Alternatively, the porous surface may be exposed to any of a variety of monomers or other polymer precursors which are allowed or caused to flow into the pores prior to polymerization.

The functional layer may thereafter be applied to the tie layer using any of a variety of techniques such as dipping, spraying, condensation or others depending upon the nature of the functional layer.

Using a porous layer as a bonding interface may also allow bonding of a greater range of polymers and other coating materials with medical devices. One skilled in the art is no longer restricted to coating materials with a particular bonding characteristic, as the porous layer may allow bonding of materials that would otherwise fail to bond adequately to a non-porous device surface. In one embodiment of the invention, a medical device with a porous bonding surface is provided. The surface may have an average thickness of about 0.1 microns to about 1000 microns, and preferably about 0.1 microns to about 10 microns. The average pore size ranges from about 1 nanometer to about 100 microns, and preferably about 10 nanometers to about 5 microns. In other embodiments, the average pore size is about 1 nm to about 50 nm. The porosity of the bonding surface may range from about 1% to about 99%, typically about 25% to about 75% and preferably about 50% to about 70%. In other preferred embodiments, the porosity of the bonding surface is about 40% to about 70%. In another embodiment of the invention, the medical device comprises a drug-eluting polymer coating bonded to the nanoporous bonding surface. In one embodiment of the invention, the medical device is a metallic coronary stent with porous metallic bonding surface bonded with a paclitaxel or sirolimus slow-release polymer coating. One skilled in the art will understand that any of a variety of other therapeutic agent-impregnated, slow-release polymer coatings may be used. The porous bonding layer also may be nanoporous. In one embodiment of the invention, the polymer material is applied to the surface of the PES or other nanoporous coating wherein the polymer solvent is chosen based on its physical properties to control the extent of penetration (or wicking) of the polymeric composition into the nanopores. Physical properties to consider include but are not limited to viscosity, wetting, vapor pressures, and drying times. One can also vary the conditions for applying the polymer-solvent mixture to control the extent of polymer penetration into the nanoporous coating. For example, one can vary the spray distance, the initial polymer:solvent ratio, and spray velocity in such a manner to control the "wetness" or solvent/polymer ratio at the instant it reaches the nanoporous coating. Generally, the wetter the mixture is at the instant of deposition, the greater the penetration or wicking into the nanoporous structure. In an extreme example, conditions are varied such that the solvent:polymer composition and application conditions are selected such that it is nearly completely "dried" at the time of deposition on the nanoporous device, such that there is virtually no penetration of the polymeric:solvent mixture into the nanoporous coating. These few examples are by no means inclusive, and there are a wide range of different solvents, and application methods that can be varied to control penetration into the nanoporous coating. Note that these principles apply irrespective of the method used to generate the nanoporous coating and are applicable to any polymeric or other coating material.

In one embodiment of the invention, the medical device comprises a metallic coronary stent with one or more porous regions, a polymeric primer layer bonded to the porous regions, and a drug release layer bonded to the polymeric primer layer. For example, to improve polymer adherence, one may use a parylene C coat on a metallic stent prior to application of a polyethylene-co-vinyl acetate (PEVA) and poly n-butyl methacrylate (PBMA) drug bearing polymer coat. Other polymeric primer layer materials that may be used include but are not limited to a polyfluoro copolymer, an ethylene vinyl alcohol copolymer, poly-lactide co-glycolide (PLGA) or other biodegradable polymers including but not limited to poly lactic acid (PLA), or derivatives, or poly(butyl methacrylate). One skilled in the art will understand other drug releasing materials may be used in addition to PEVA and PBMA. Additionally, a drug-free topcoat of PBMA, PLGA, or PLA may be used to alter drug delivery.

K. Nanoporous Layers with Polymer Topcoats

As mentioned previously, the porous zone may further comprise a topcoat or other surface coating to further control the release kinetics of the therapeutic agent(s) contained within the dealloyed porous zone. Typically, the topcoat or surface coating comprises a polymer. Optionally, a cross-linking agent may be included. An optional primer layer can be applied between the dealloyed porous zone to improve the adhesion of the topcoat to the dealloyed porous zone. An optional finishing layer may also be applied over the topcoat layer and can be used for improving the biocompatibility of the underlying layer. The following is a more detailed description of suitable materials or agents and methods useful in producing the topcoats or surface coatings of the invention.

In one embodiment, the topcoat layer or layers are applied to a porous layer already loaded with therapeutic agent, drug, or other substance using the methods described herein. The solvent used for dissolving and applying the topcoat materials are chosen based on their wetting, solubility properties for the therapeutic material, drying time, viscosity, and other properties to control the amount of drug that mixes within the top coat, to regulate penetration of the top coat materials into the coating and to give desired release kinetics as well as to promote polymer anchoring to the nanoporous coating. In this manner, one skilled in the art can create a wide range of end products with varying elution properties, as well as enhanced adherence to the biomedical device by virtue of rooting within the PES. The penetration of the polymer-solvent material into the nanoporous layer may be characterized by any of a variety of measures. In one embodiment, the penetration of the polymer-solvent material may be measured by the amount or percentage of the interstitial space in the nanoporous layer that is filled by the polymer-solvent material, or by the depth of penetration across the nanoporous layer. The interstitial space may be filled by any amount from about 1% to about 100%. In other embodiments, to further increase rooting or anchoring of the topcoat or bonded polymer layer, the interstitial space may be filled up to at least about 30% or about 60%. Similarly, when penetration of the polymer-solvent mixture is measured as a depth of penetration of the porous layer, the percent of penetration may be anywhere from about 1% to about 100%. In other embodiments, to further increase rooting or anchoring of the topcoat or bonded polymer layer, the interstitial space may be penetrated to a depth of at least about 30% or about 60%. In another embodiment of the invention, it is recognized that the degree of penetration of the polymer-solvent mixture may be affected by the average pore diameter of the nanoporous layer. In such embodiments, the degree of penetration may be characterized as a ratio of the distance of penetration to the average pore diameter of the nanoporous layer. This ratio may range anywhere from about 0.1 to about 500 or more. In some embodiments, the ratio is at least about 10, while in other embodiments, the ratio may be at least about 50 or about 100. One or measures of polymer-solvent penetration may be more appropriate, depending on the characteristics of the polymer-solvent material and/or the nanoporous layer. For example, if the filling of the nanoporous structure along the pore pathways by the polymer-solvent mixture is incomplete, measures of penetration depth may be more accurate than estimated measures of filling percentage. In one embodiment, a top coat solvent with high solubility, low viscosity, slow drying/curing rates, and high wetting characteristics is used to create a final product with significant drug contained within the top coat, but also significant top coat materials embedded within the porous coating. Alternatively, one could use a top coat solvent with low solubility for the therapeutic agent, fast drying/curing time, and low wetting properties to create a top coat that is largely devoid of drug and where there is relatively less polymer material embedded into the porous coating. This latter product would be expected to show delayed release kinetics. These are merely two examples of an infinite range of possibilities whereby selection of specific solvents, application methods, therapeutic agents, and other related parameters can be varying to create a final combination porous layer with top coats that display different elution rates and/or adherence properties.

In one embodiment of the invention, the polymer material is sprayed onto the surface of the PES, the polymer material comprising therapeutic agent(s) and polymer solvent(s) chosen with specific properties including but not limited to viscosity, drug solubility, wetting, vapor pressures, and drying times to precisely control both mixing of drug within and on the nanoporous coating within the polymer coating, as well as to control penetration of the polymer into the nanoporous coating to improve rooting and anchoring. For example, if it is desired to have extensive mixing of rapamycin with polymer and extensive penetration of the mixture into the nanoporous coating, one could use ethanol as the polymer solvent of choice since it has an extremely high rapamycin solubility (>90 mg/ml) but also low viscosity and a relatively long drying time relative to other solvent choices such as acetone (bp=56.2 vs 78.3 for ethanol). That is, use of acetone would result in reduced mixing of drug and polymer as well as reduced penetration of the mixture of polymer and drug into the PES or nanoporous coating because of its lower rapamycin solubility and faster drying time. In another embodiment, one could use ethyl acetate as the polymer solvent of choice. This solvent has a boiling point (bp) approximately the same as ethanol (77.1 C) but with a lower rapamycin solubility. As such, one could achieve a topcoat that has excellent penetration and adherence to the nanoporous coating, but much less drug within the coating itself. One can also vary the conditions for applying the polymer-solvent mixture to control the extent of drug-polymer intermixing and penetration into the nanoporous coating. For example, one can vary the spray distance (generally between about 1 mm and about 20 cm but more preferably between about 0.5 cm and about 5 cm using a Sono-tek MicroMist Stent Coating System (Milton, N.Y.)), the initial polymer:solvent ratio (between about 0.1 and about 100% but preferably between about 0.5 and about 3%), and spray velocity (generally between about 0.001 and about 1.0 ml/min but preferably between about 0.010 and about 0.075 ml/min) in such a manner to control the "wetness" or solvent/polymer ratio at the instant it reaches the nanoporous coating. Generally, the wetter the mixture is at the moment of deposition or contact with the nanoporous surface, the greater the mixing with drug within and on the nanoporous coating, which typically results in greater penetration of (or wicking into) the nanoporous structure. In an extreme example, conditions are varied such that the solvent:polymer composition and application conditions are selected such that it is nearly completely "dried" at the time of deposition on the nanoporous device, such that virtually no drug solvent mixing occurs, or penetration of the coating into the nanoporous coating. These few examples are by no means inclusive, and there are a wide range of different drug solvents, and application methods (i.e. spraying conditions, dipping methods, etc.) that can be varied to control drug-polymer mixing and penetration into the nanoporous coating. Note that these principles apply irrespective of the method used to generate the nanoporous coating and are applicable to any drug, compound, or other therapeutic agent or combination thereof. Although not inclusive, additional solvents to consider for application of rapamycin are listed in Table 1 of Simamora et al Int J Pharmaceutics 213: 25-29, 2001. Each solvent has distinct physical and solubility properties to allow selective control of drug-polymer mixing and penetration into nanoporous coatings. Solvents include but are not limited to the following solvents or solvent classes: ethanol, methanol, acetone, chloroform, ethyl acetate, THF, benzyl alcohol, ethyl lactate, polyethyethylene glycol, propylene dlycol, dlycerin triacetin, diacetin, acetyl triethyl citrate, ethyl lactate N-methyl-2-pyrrolidinone, buyrolactone, dimethyl isosorbide, tryethylene glycol dimethyl ether, ethoxy diglycol, glycerol, glycerol formal, dimethyl formamide, dimethyl acetamide, dimethyl solfoxide, CHCL3, ketones, or alcohols.

The net consequences of these topcoat deposition methods are to alter drug release kinetics, payload capacity, and adhesion to the biomedical device. For example, in the case of promoting mixing, one can achieve more rapid onset of release because of the absence of a drug free top coat. Alternatively, one may achieve slower release kinetics by depositing a relatively drug free polymeric top coat without drug. In addition, one may vary the coating thickness and/or density to alter the release kinetics of a therapeutic agent. For example, a thicker and/or denser polymeric coating may be used to slow the release kinetics. An additional embodiment of the invention, is to include a drug, compound, or other therapeutic agent within the solvent:polymer mixture prior to application. In this manner, one can vary the drug concentration within the final polymeric topcoat and achieve differing release properties. Still another embodiment, is to perform polymeric top coat applications under conditions described elsewhere in this application (e.g. use of low vacuum, pressure, and temperature cycles, solvent prewetting steps, etc.) that facilitate removal of trapped gas from within nanoporous coatings and improved penetration of polymer-drug mixtures. For example, the entire process can be done under vacuum at pressures just exceeding the solvent vapor pressures/boiling points. The principle is that the more extensive the drug-polymer mixing and the deeper the penetration of this mixture, the slower the release kinetics and the more robust the polymer adherence is to the biomedical device. Moreover, these parameters can be carefully controlled by appropriate selection and matching of solvents, drugs, nanoporous coating morphological characteristics, and application methods just to name a few of the control variables possible to achieve the desired end product.

The polymer(s) useful for forming the coating should be ones that are biocompatible and avoids irritation to body tissue. In one preferred embodiment, the polymers are biostable ones, such as polyurethanes, silicones, and polyesters. Other polymers which can be used include ones that can be dissolved and cured or polymerized on the medical device. In another preferred embodiment, a bioerodable or biodegradable material may be used in the topcoat provide control of the release kinetics from the dealloyed porous zone that diminishes over time so that permanent or long-term trapping of a therapeutic agent in the dealloyed porous zone may be reduced while prolonging the initial release profile after implantation. Suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as NYLON 66 and polycaprolactone, alkyd resins, polycarbonates, polyoxymethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Other coating materials may include lactone-based copolyesters, polyanhydrides, polyaminoacids, polysaccharides, polyphosphazenes, poly (ether-ester) copolymers, and blends of such polymers, poly (ethylene) vinylacetate, poly(hydroxy)ethylmethylmethacrylate, polyvinal pyrrolidone; polytetrafluoroethylene, and cellulose esters.

More preferably for medical devices which undergo mechanical challenges, e.g. expansion and contraction, the polymers are selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the topcoat better adheres to the surface of the porous zone when the medical device is subjected to forces or stress.

Poly(ethylene-co-vinyl alcohol) (EVAL) is one example of a polymer that can be included in the optional primer layer, the topcoat layer and the finishing coat layer. EVAL has the general formula —[CH2-CH2]m-[CH2-CH(OH)]n-. EVAL is a product of hydrolysis of ethylene-vinyl acetate copolymers and may also be a terpolymer including up to 5 molar % of units derived from styrene, propylene and other suitable unsaturated monomers. A brand of copolymer of ethylene and vinyl alcohol distributed commercially under the trade name EVAL by Aldrich Chemical Co. of Milwaukee, Wis., and manufactured by EVAL Company of America of Lisle, Ill., can be used.

Other suitable polymers can also be used for making the optional primer layer, the topcoat layer and the finishing coat layer. Representative examples include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydride, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinylidene halides (such as polyvinylidene fluoride and polyvinylidene chloride), polyvinyl ethers (such as polyvinyl methyl-ether), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as NYLON 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellulose nitrate, cellulose propionate, cellulose ethers, carboxymethyl cellulose, CELLOPHANE and mixtures thereof.

Poly(ethylene glycol) (PEG) is one example of a polymer that can be included in the topcoat layer and/or the finishing coat layer. PEG is a biologically compatible product having the formula H—[O—CH2-CH2-O—CH2-CH2]n-OH, and can have a molecular weight within a range of between about 1,000 and about 100,000 Daltons, for example, between 2,000 and 10,000 Daltons, such as 5,000 Daltons. The value of the integer "n" in the formula of PEG is about 56 for PEG having molecular weight of about 5,000.

Other suitable polymers can also be used to form in the topcoat layer and/or the finishing coat layer. Representative examples include heparin, hyaluronic acid, and silk-elastin protein block-copolymer. Heparin comprises a mixture of sulfated polysaccharide chains based on D-glucosamine and D-glucoronic or L-iduronic acid. A brand of heparin known under the trade name DURAFLO can be used. DURAFLO can be obtained from Baxter Healthcare Corporation of Deerfield, Ill. Hyaluronic acid is a linear polysaccharide composed of disaccharide units of N-acetylglucosamine and D-glucoronic acid. In hyaluronic acid, uronic acid and the aminosugar are linked by alternating β-1,4 and β-1,3 glucosidic bonds. Silk-elastin protein block-copolymers combine the repeating blocks of amino acids thus providing the copolymer with the, mechanical strength characterizing silk and the flexibility characterizing elastin. Silk-elastin block-copolymer can be obtained from Protein Polymer Technologies, Inc. of San Diego, Calif.

Although the invention can be practiced by using a single type of polymer to form the topcoat layer, various combinations of polymers can be employed.

According to an embodiment of the present invention, the polymeric coating can comprise interpenetrating polymer networks (IPN). For the purposes of the present invention, a definition of the IPN used by the International Union of Pure and Applied Chemistry (IUPAC) is adopted. The IUPAC describes the IPN as a polymer comprising two or more networks which are at least partially interlaced on a molecular scale, but not covalently bonded to each other and cannot be separated unless chemical bonds are broken. In other words, an IPN structure represents two or more polymer networks that are physically entangled. One example of an IPN that can be used is a surface hydrogel.

One example of a product that can be used for forming the IPN is a PEG-based unsaturated product, for example, pre-polymer of PEG-acrylate or methacrylate having a general formula $CH_2=CX-COO-[CH_2-CH_2-O]_n-H$, where X is hydrogen (acrylates) or methyl (methacrylates). Weight average molecular weight of PEG-acrylate or methacrylate can be within a range of about 10,000 to 100,00 Daltons. PEG-acrylate prepolymer can be applied on the surface of the drug-polymer or topcoat layer and cured, for example, using a radical initiator which is activated by UV radiation (UV initiators), light (light initiators), or heat (thermal initiators). Examples of appropriate initiators include acetophenone, 2,2-dimethoxy-2-phenol-acetophenone (UV initiators), camproquinone, ethyl-4-N,N-dimethyl aminobenzoate (light initiators), and benzoyl peroxide (thermal initiator). As a result of the curing process, PEG-acrylate will partially cross-link and partially physically entangle with the polymer of the underlying layer thus forming the outermost coat layer which includes an IPN. PEG-acrylate or methacrylate is intended to broadly include poly(ethylene glycol)-diacrylate (PEG-diacrylate) and poly(ethylene glycol)-dimethacrylate (PEG-dimethacrylate). PEG-acrylate or methacrylate and PEG-diacrylate or dimethacrylate can be optionally terminated, for example, with stearic acid, to form PEG-acrylate-stearate PEG-methacrylate-stearate, respectively.

Examples of other products that can be used for forming the IPN include such unsaturated reactive products as N-vinylpyrrolidone, heparin and its derivatives, hyaluronic acid and its derivatives, some hydrogel-forming products such as poly(butyleneterephthalate-co ethylene glycol) (PBT-PEG), and mixtures of any of these products with each other or with PEG-acrylate or methacrylate.

Suitable derivatives of heparin include sodium heparin (Na-Hep), heparin benzalkonium chloride (HBAC), and heparin tridodecyl methyl ammonium chloride (HTDMAC). Derivatives of heparin can also include heparin modified by introduction of photoactivatable groups in the heparin molecule (the groups that are inactive under ambient conditions but become reactive when irradiated by UV-light, for example, at the frequency of about 360 nm). Examples of photoactivatable groups include groups derived from benzophenone or dithiocarbonate. Methods of introducing the photoactivatable groups into the molecules of heparin are known to those having ordinary skill in the art. Other derivatives of heparin can include heparin containing a moiety that tends to bind to albumin, for example a the —(CH2)18- moiety.

Embodiments of the present invention can be further illustrated by the following examples.

EXAMPLE 1

A first composition can be prepared by mixing the following components:
  (a) between about 0.1 mass % and about 15 mass %, for example, about 2.0 mass % of EVAL; and
  (b) the balance of DMAC solvent.

The first composition can be applied onto a dealloyed porous layer, for example, by spraying or dipping, to form the topcoat layer. The topcoat layer can have, for example, a total solids weight of about 250 μg.

A second composition can be prepared by mixing the following components:
  (c) between about 0.1 mass % and about 15 mass %, for example, about 2.0 mass % of EVAL;
  (d) between about 0.1 mass % and about 5 mass %, for example, about 1.0 mass % of DURAFLO;
  (e) between about 25 mass % and about 30 mass %, for example, 27.85 mass % of dimethylsulfoxide (DMSO) solvent;
  (f) between about 5 mass % and about 6 mass %, for example, 5.65 mass % of tethrahydrofurane (THF) solvent; and
  (g) the balance, DMAC solvent.

The second composition can be applied onto the dried topcoat layer, for example, by spraying or dipping, to form the finishing coat layer having a total solids weight of about 200 μg.

EXAMPLE 2

A first composition can be prepared by mixing the following components:
  (a) between about 0.1 mass % and about 15 mass %, for example, about 2 mass % of EVAL; and
  (b) the balance, DMAC solvent.

The first composition can be applied onto the dealloyed porous layer, for example, by spraying, to form the topcoat layer having a total solids weight of about 300 μg.

A second composition can be prepared by mixing the following components:
  (c) between about 0.1 mass % and about 15 mass %, for example, about 2.0 mass % of EVAL;
  (d) between about 0.1 mass % and about 5 mass %, for example, about 1.0 mass % of poly(ethylene glycol) having molecular weight of about 5,000 Daltons (PEG5000); and
  (e) the balance, DMAC solvent.

The second composition can be applied onto the dried topcoat layer, for example, by spraying or dipping, to form the finishing coat layer having a total solids weight of about 200 µg.

EXAMPLE 3

A first composition can be prepared by mixing the following components:
(a) between about 0.1 mass % and about 15 mass %, for example, about 2 mass % of EVAL; and
(b) the balance, DMAC solvent.

The first composition can be applied onto the dried drug-polymer layer, for example, by spraying, to form the topcoat layer having a total solids weight of about 300 µg.

A second composition can be prepared by mixing the following components:
(c) between about 0.1 mass % and about 15 mass %, for example, about 1.3 mass % of EVAL;
(d) between about 0.1 mass % and about 5 mass %, for example, about 0.7 mass % of PEG5000; and
(e) the balance, DMAC solvent.

The second composition can be applied onto the dried topcoat layer, for example, by spraying or dipping, to form the finishing coat layer having a total solids weight of about 200 µg.

EXAMPLE 4

A stent can be coated as described in Example 3, except the finishing coat layer can have a total solids weight of about 150 µg.

EXAMPLE 5

A first composition can be prepared by mixing the following components:
(a) between about 0.1 mass % and about 15 mass %, for example, about 2 mass % of EVAL; and
(b) the balance, DMAC solvent.

The first composition can be applied onto the dealloyed porous layer, for example, by spraying, to form the topcoat layer having a total solids weight of about 300 µg.

A second composition can be prepared by mixing the following components:
(c) between about 0.1 mass % and about 15 mass %, for example, about 1.3 mass % of EVAL;
(d) between about 0.1 mass % and about 5 mass %, for example, about 0.7 mass % of PEG5000; and
(e) the balance, DMAC solvent.

The second composition can be applied onto the dried topcoat layer, for example, by spraying or dipping, to form the finishing coat layer having a total solids weight of about 150 µg.

EXAMPLE 6

A first composition can be prepared by mixing the following components:
(a) between about 0.1 mass % and about 15 mass %, for example, about 2 mass % of EVAL; and
(b) the balance, DMAC solvent.

The first composition can be applied onto the dealloyed porous layer, for example, by spraying, to form the topcoat layer having a total solids weight of about 250 µg.

A second composition can be prepared by mixing the following components:
(c) between about 0.1 mass % and about 15 mass %, for example, about 1.3 mass % of EVAL;
(d) between about 0.1 mass % and about 5 mass %, for example, about 0.7 mass % of PEG5000; and
(e) the balance, DMAC solvent.

The second composition can be applied onto the dried topcoat layer, for example, by spraying or dipping, to form the finishing coat layer having a total solids weight of about 150 µg.

EXAMPLE 7

A first composition can be prepared by mixing the following components:
(a) between about 0.1 mass % and about 15 mass %, for example, about 2 mass % of EVAL; and
(b) the balance, DMAC solvent.

The first composition can be applied onto the dealloyed porous layer, for example, by spraying, to form the topcoat layer having a total solids weight of about 250 µg.

A second composition can be prepared by mixing the following components:
(c) between about 0.1 mass % and about 15 mass %, for example, about 1.3 mass % of EVAL;
(d) between about 0.1 mass % and about 5 mass %, for example, about 0.7 mass % of PEG5000; and
(e) the balance, DMAC solvent.

The second composition can be applied onto the dried topcoat layer, for example, by spraying or dipping, to form the finishing coat layer having a total solids weight of about 150 µg.

EXAMPLE 8

A first composition can be prepared by mixing the following components:
(a) between about 0.1 mass % and about 15 mass %, for example, about 2 mass % of EVAL; and
(b) the balance, DMAC solvent.

The first composition can be applied onto the dealloyed porous layer, for example, by spraying, to form the topcoat layer having a total solids weight of about 200 µg.

A second composition can be prepared by mixing the following components:
(c) between about 0.1 mass % and about 15 mass %, for example, about 0.5 mass % of EVAL;
(d) between about 0.1 mass % and about 5 mass %, for example, about 0.25 mass % of hyaluronic acid; and
(e) the balance, DMSO solvent.

The second composition can be applied onto the dried topcoat layer, for example, by centrifugation, to form the finishing coat layer having a total solids weight of about 150 µg. The method of coating by centrifugation is known to those having ordinary skill in the art.

EXAMPLE 9

A dealloyed porous layer can be coated as described in Example 8, except the topcoat layer can have a total solids weight of about 100 µg.

EXAMPLE 10

A first composition can be prepared by mixing the following components:
(a) between about 0.1 mass % and about 15 mass %, for example, about 2 mass % of EVAL; and
(b) the balance, DMAC solvent.

The first composition can be applied onto the dealloyed porous layer, for example, by spraying, to form the topcoat layer having a total solids weight of about 200 µg.

A second composition can be prepared by mixing the following components:
- (c) between about 0.1 mass % and about 15 mass %, for example, about 0.5 mass % of EVAL;
- (d) between about 0.1 mass % and about 5 mass %, for example, about 0.25 mass % of hyaluronic acid; and
- (e) the balance, DMSO solvent.

The second composition can be applied onto the dried topcoat layer, for example, by centrifugation, to form the finishing coat layer having a total solids weight of about 150 µg.

EXAMPLE 11

A first composition can be prepared by mixing the following components:
- (c) between about 0.1 mass % and about 15 mass %, for example, about 0.5 mass % of silk elastin product;
- (d) between about 0.1 mass % and about 5 mass %, for example, about 0.5 mass % of hyaluronic acid; and
- (e) the balance, distilled water.

The first composition can be applied onto the dealloyed porous layer, for example, by centrifugation, to form the finishing coat layer having a total solids weight of about 150 µg.

EXAMPLE 12

A dealloyed porous layer can be coated as described in Example 11, except the topcoat layer can have a total solids weight of about 100 µg.

EXAMPLE 13

A first composition can be prepared by mixing the following components:
- (a) between about 0.1 mass % and about 15 mass %, for example, about 2 mass % of EVAL; and
- (b) the balance, DMAC solvent.

The first composition can be applied onto the dried drug-polymer layer, for example, by spraying, to form the topcoat layer having a total solids weight of about 200 µg.

A second composition can be prepared by mixing the following components:
- (c) between about 0.1 mass % and about 15 mass %, for example, about 0.5 mass % of silk elastin product
- (d) between about 0.1 mass % and about 5 mass %, for example, about 0.5 mass % of hyaluronic acid; and
- (e) the balance, distilled water.

The second composition can be applied onto the dried topcoat layer, for example, by centrifugation, to form the finishing coat layer having a total solids weight of about 150 µg.

EXAMPLE 14

A composition can be prepared, the composition including:
- (a) about 3 mass % of PEG-acrylate having M, within a range of about 10,000 and 100,000;
- (b) about 1 mass % of 2,2-dimethoxy-2-phenol-acetophenone; and
- (c) the balance a solvent mixture, the mixture containing de-ionized water and ethanol in a mass ratio of about 4:1.

The composition can be applied on the dealloyed porous layer and irradiated with UV-light at a wavelength of 360 nm for about 10 seconds, followed by drying, to form a topcoat layer comprising an IPN based on poly(PEG-acrylate).

EXAMPLE 15

The dealloyed porous layer can be coated as described in Example 14, except that the same amount of benzoyl peroxide can be used the instead of acetophenone. The topcoat layer-forming IPN can be formed by subjecting the stent to a temperature of about 80° C. for about 5 minutes.

EXAMPLE 16

A composition can be prepared, the composition including:
- (a) about 20 mass % of N-vinylpyrrolidone;
- (b) about 3 mass % of PEG-acrylate having Mw within a range of about 10,000 and 100,000;
- (c) about 1 mass % of 2,2-dimethoxy-2-phenol-acetophenone; and
- (d) the balance of a solvent mixture, the mixture containing de-ionized water and ethanol in a mass ratio of about 4:1.

The composition can be applied on a dealloyed porous layer and a topcoat layer comprising an IPN can be formed as described in Example 14.

EXAMPLE 17

A composition can be prepared, the composition including:
- (a) about 3 mass % of PEG-acrylate having M, within a range of about 10,000 and 100,000;
- (b) about 3 mass % of heparin benzalkonium chloride (HBAC);
- (c) about 1 mass % of acetophenone; and
- (d) the balance a solvent mixture, the mixture containing iso-propanol and dimethylacetamide in a mass ratio of about 14:1.

The composition can be applied on a dealloyed porous layer and a topcoat layer comprising an IPN can be formed as described in Example 14.

EXAMPLE 18

A composition can be prepared, the composition including:
- (a) about 2 mass % of EVAL;
- (b) about 0.7 mass % of PEG having M, of about 17,500 Daltons;
- (c) about 0.7 mass % of PEG-diacrylate having M, of about 10,000 Daltons;
- (d) about 0.7 mass % of HBAC;
- (e) about 0.1 mass % of 2,2-dimethoxy-2-phenol-acetophenone; and
- (f) the balance dimethylacetamide solvent.

The composition can be applied on a dealloyed porous layer and a topcoat layer comprising an IPN can be formed as described in Example 14.

EXAMPLE 19

A composition can be prepared, the composition including:
- (a) about 7 mass % of EVAL;
- (b) about 2 mass % of PEG having M, of about 17,500 Daltons;
- (c) about 2 mass % of PEG-diacrylate having M, of about 10,000 Daltons;
- (d) about 2 mass % of HBAC;
- (e) about 0.5 mass % of 2,2-dimethoxy-2-phenol-acetophenone; and
- (f) the balance dimethylacetamide solvent.

The composition can be applied on a stent by spin coating and a topcoat layer comprising an IPN can be formed.

EXAMPLE 20

A composition can be prepared, the composition including:
- (a) about 2 mass % of EVAL;
- (b) about 0.4 mass % of PEG having Mw of about 17,500 Daltons;
- (c) about 0.2 mass % of HBAC; and
- (d) the balance of dimethylacetamide solvent.

The composition can be applied on a dealloyed porous layer, for example, by spraying, to form a topcoat layer.

EXAMPLE 21

A composition can be prepared, the composition including:
- (a) about 3 mass % of EVAL;
- (b) about 2 mass % of PEG having Mw of about 17,500 Daltons;
- (c) about 2 mass % of sodium heparin (Na-Hep); and
- (d) the balance, a solvent blend, the blend comprising formamide (FA), methanol (MeOH) and dimethylacetamide (DMAC) in a mass ratio FA:MeOH:DMAC of about 1:1.05:3.

To prepare the composition, Na-Hep can be dissolved in FA first at a temperature between about 60° C. and 100° C., to form about 10% Na-Hep/FA solution, followed by adding EVAL, PEG, MeOH and DMAC to the Na-Hep/FA solution. The composition can be applied on a dealloyed porous layer, for example, by spraying while the temperature of the composition is maintained between about 55° C. and 70° C., to form a topcoat layer.

The process of the release of the drug from a coating having both topcoat and finishing coat layers includes at least three distinctive steps. First, the drug is absorbed by the polymer of the topcoat layer on the dealloyed porous layer/topcoat layer interface. Next, the drug diffuses through the topcoat layer using empty spaces between the macromolecules of the topcoat layer polymer as pathways for migration. Next, the drug arrives to the topcoat layer/finishing layer interface. Finally, the drug diffuses through the finishing coat layer in a similar fashion, arrives to the outer surface of the finishing coat layer, and desorbs from the outer surface. At this point, the drug is released into the blood stream or adjacent tissue. Consequently, a combination of the topcoat and finishing coat layers, if used, can serve as a rate limiting barrier.

As mentioned previously, the topcoat or surface coating itself may also contain one or more therapeutic agents that are the same or different from the therapeutic agents contained in the dealloyed porous zone. The appropriate mixture of polymers may be coordinated with biologically active materials contained in the porous zone and/or the topcoat layer to produce desired effects when coated on a medical device in accordance with the invention. The biologically active agents of the topcoat, if any, may be incorporated by diffusion of the agents from the dealloyed polymer layer. If the drugs are suspended in the solution, they should be dispersed as fine particles ranging from about 1 to about 100 microns in average particle size. Alternatively, if a polymer having a relatively low melting point is used, the polymer and biologically active agent can be blended in the molten stage (such as by casting or coextrusion) if the biologically active agent does not degrade at the molten temperature. In one embodiment, the ratio of topcoat thickness to average particle diameter is preferably greater than about 3, and more preferably greater than about 5.

The concentration or loading of the biologically active material in the topcoat layer may be varied according to the therapeutic effects desired. Also, the loading, if any, in terms of the ratio of therapeutic agent to polymer in the topcoat layer, will depend upon the efficacy of the polymer in securing the therapeutic agent onto the medical device and the rate at which the coating is to release the therapeutic agent to the body tissue. Generally, when used with a therapeutic agent, the topcoat layer may contain about 0.1 to about 90% by weight or preferably about 10 to about 45% by weight of the biologically active material. Most preferably, about 25% to about 40% by weight of the drug should be incorporated in the dealloyed layer.

The topcoat layer composition generally may be prepared by adding micronized drug particles into a selected amount of polymer. Solvent and optional crosslinking agents are then added to this mixture which is then stirred until it is homogeneous. Depending on the nature of the biologically active material and the solvent and polymers used, the mixture need not be a solution. The drug particles need not be dissolved into the mixture but may be suspended therein.

In one embodiment, the topcoat layer will generally be prepared to be substantially free of any ionic surfactant. However, small amounts may become present, especially at an interface between a topcoat layer and a porous zone. For instance, small amounts of ionic surfactant may become present as a result of penetration during a topcoat layer spraying process or due to migration from the topcoat layer during shelf storage. The porous zone, apart from the interface with the topcoat layer, will preferably have less than about 0.5 weight percent complex, more preferably less than about 0.4 weight percent complex.

Solvents suitable for forming the topcoat layer composition are ones which can dissolve the polymer into solution and do not alter or adversely impact the therapeutic properties of the biologically active material contained in the either the porous zone or topcoat layer. Examples of useful solvents for silicone include tetrahydrofuran (THF), chloroform and dichloromethane.

To enhance the stability of the topcoat layer and the timed or long-term release of the therapeutic agents, crosslinkers may be incorporated into the topcoat layer. For example, hydridosilane may be used as a crosslinking agent for silicone.

Once prepared, the topcoat mixture is then applied to a porous zone or the surface of the medical device. The topcoat layer composition may be applied by dipping the medical device into the composition or by spraying the composition onto at least a portion of the device. The thickness of the topcoat layer formed may range from about 1 micron to about 100 microns and preferably from about 2 microns to about 15 microns.

Since different topcoat thicknesses can be readily achieved by adjusting the number of spray cycles, spray coating the medical device is preferred. In one embodiment, an airbrush such as a Badger Model 150 (supplied with a source of pressurized air) may be used to coat the device. If a significant amount of surface area is to be coated, it may be preferable to place the device in a rotating fixture to facilitate the coverage of the device's surface. For example, to coat the entire surface of a vascular stent, the ends of the device are fastened to a rotating fixture by resilient retainers, such as alligator clips. The stent is rotated in a substantially horizontal plane around its axis. The spray nozzle of the airbrush may be placed 2-4 inches from the device.

The thickness of the topcoat can be adjusted by the speed of rotation and the flow rate of the spray nozzle. The speed of rotation is usually adjusted at about 30 to about 50 rpm, typically at about 40 rpm. The flow rate of the spray nozzle, which can range from about 4 to about 10 ml coating per minute may also be adjusted. Usually, a number of spray-coats will be required to achieve the desired thickness of a topcoat layer. If a non-spray process is utilized, such as dip coating, casting or coextrusion, then one coat may be sufficient.

Moreover, several topcoat layers of different compositions may be used to further modify the release kinetics from the porous zone, or so that more than one drug and/or polymer may be incorporated into the topcoat. The placement or order of the different layers may also be determined by the diffusion or elution rates of the therapeutic agent involved, the desired rate of delivering the therapeutic agent to the body tissue, as well as the degradation characteristics of the polymer or therapeutic agent.

After application of the topcoat layer, the polymer can be cured to produce a polymer matrix, with the biologically active material as desired in some embodiments, and the solvent evaporated. Certain polymers, such as silicone, can be cured at relatively low temperatures, (e.g. room temperature) in what is known as a room temperature vulcanization (RTV) process. More typically, the curing/evaporation process involves higher temperatures so that the coated device is heated in an oven. Typically, the heating occurs at approximately 90 degrees Celsius or higher for approximately about 1 to about 16 hours when silicone is used. For certain coatings where the polymer used or the therapeutic agent within the topcoat, if any, such as ones containing dexamethasone, can tolerate greater temperatures, the heating may occur at temperatures as high as about 150 Celsius. The time and temperature of heating will of course vary with the particular polymer, drugs, solvents and/or crosslinkers used. One of skill in the art is aware of the necessary adjustments to these parameters. Also, the devices may be cured after the topcoat layer has been applied.

In one embodiment, the topcoat layer contains an ionic surfactant-drug complex that is preferably prepared by dissolving the complex in a solvent or a mixture of solvents. However, it can also be prepared by blending the ionic surfactant drug complex with polymer(s) or polymer(s)/solvent mixtures. Suitable drugs have been described above. Appropriate ionic surfactants include quaternary ammonium compounds such as one of the following: benzalkonium chloride, tridodecylmethylammonium chloride (TDMAC), cetylpyridinium chloride, benzyldimethylstearylammonium chloride, benzylcetyl dimethyl ammonium chloride. An additional example of an appropriate ionic surfactant includes a polymeric surfactant, such as a quaternary ammonium salt of acrylate polymer including 2-(trimethyl amine)-ethyl methacrylate bromide, or a quaternary ammonium salt of cellulose such as JR400 and QUATRISOFT manufactured by Union Carbide. Preferably, the ionic surfactant comprises TDMA.

The surfactant-drug complex can either be purchased on the open market or made in the laboratory. For instance, benzalkonium chloride is made and sold by ALDRICH. TDMA-heparin is made and sold by STS POLYMERS. The skilled artisan is aware of methods for making surfactant-drug complexes.

The concentration or loading of biologically active material in the outer layer, if any, may be varied according to the therapeutic effects desired. Generally, the topcoat layer may contain about 0 to about 100% by weight or sometimes about 30 to about 100% by weight of the complex of the biologically active material. In some embodiments, about 45 to about 100% by weight of the drug complex should be incorporated in the topcoat layer.

The topcoat layer composition is then applied to the medical device. The composition can be applied by such methods as dipping, casting, extruding or spray coating to form a layer in which some of the drug-surfactant complex will penetrate into the very top of pore structure of the porous zone. Typically, spray coating the topcoat layer onto the medical device is preferred since it permits the thickness of the coating to be readily adjusted. The thickness of the topcoat layer can range from about 0.1 to about 10 microns. Preferably, this layer is about 1 to about 5 microns thick. When spray coating, 1-2 spray cycles are preferred, however additional cycles may be applied depending upon the coating thickness desired.

The coating thickness ratio of the outer layer to the dealloyed layer may vary from about 1:2 to 1:100 and is preferably in the range of from about 1:10 to 1:25.

The release rate and release profile of the therapeutic agent(s) from the porous zone and/or topcoat layer may be affected by the thickness of the topcoat layer as well as the concentration of any ionically bound therapeutic in that layer. If a greater amount of the biologically active material is to be delivered initially, thinner topcoat layers may be used.

To prepare the stabilized surface coatings of this invention, the medical devices may be exposed to a low energy, relatively non-penetrating energy source such as gas plasma, electron beam energy, or corona discharge after they are covered with at least a layer of surface coating. The gas used in the gas plasma treatment can be preferably argon or other gases such as nitrogen, helium or hydrogen. Preferably the coated device is first heat cured at about 40° Celsius to about 150° Celsius prior to the exposure to the energy source for about 30 seconds to about 30 minutes. Relatively penetrating energy sources such as gamma radiation are typically but not always avoided.

Also, such treatment can be applied to the device prior to completing the application of the surface coating. For example, after the device is dealloyed to form the porous zone it can be heated and exposed to the low energy, relatively non-penetrating energy source. The treatment can be repeated after other layers have been applied.

In one suitable method, the medical devices are placed in a chamber of a plasma surface treatment system such as a Plasma Science 350 (Himont/Plasma Science, Foster City, Calif.). The system is equipped with a reactor chamber and RF solid-state generator operating at about 13.56 mHz and from about 0 to about 500 watts power output and being equipped with a microprocessor controlled system and a complete vacuum pump package. The reaction chamber contains an unimpeded work volume of about 16.75 inches (42.55 cm) by 13.5 inches (34.3 cm) by about 17.5 inches (44.45 cm) in depth.

In the plasma process, coated medical devices are placed in a reactor chamber and the system is purged with nitrogen and a vacuum applied to about 20 to about 50 mTorr. Thereafter, inert gas (argon, helium or mixture of them) is admitted to the reaction chamber for the plasma treatment. A highly preferred method of operation consists of using argon gas, operating at a power range from about 200 to about 400 watts, a flow rate of about 150 to about 650 standard ml per minute, which is equivalent to about 100 to about 450 mTorr, and an exposure time from about 30 seconds to about 5 minutes. The devices can be removed immediately after the plasma treatment or remain in the argon atmosphere for an additional period of time, typically five minutes.

Moreover, after the medical devices are coated, they are typically sterilized. Methods of sterilization are known in the art. For example, the devices can be sterilized by exposure to gamma radiation at about 2.5 to about 3.5 Mrad or by exposure to ethylene oxide. For sterilization, exposure to gamma radiation is a preferred method, particularly for heparin containing coatings. However, for certain medical devices which undergo mechanical challenges, such as expandable vascular stents, it has been found that subjecting such coated devices to gamma radiation sterilization may reduce their ability to expand. To avoid such reduction, the gas plasma treatment described above should be applied to the coated devices as a pretreatment for gamma sterilization.

Figure 26:
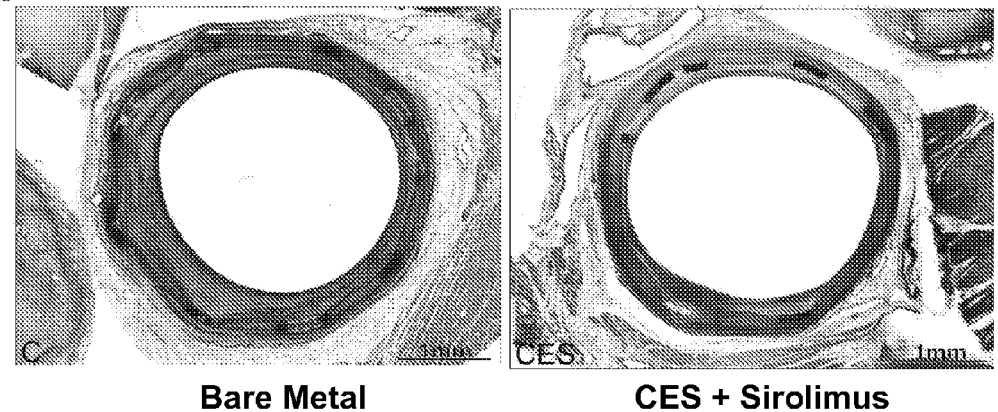
FIG. 26 is set of comparative histopathology cross sections demonstrating the degree of neointimal formation associated with a bare metal stent and stent with a nanoporous surface loaded with sirolimus.
Figure 27:
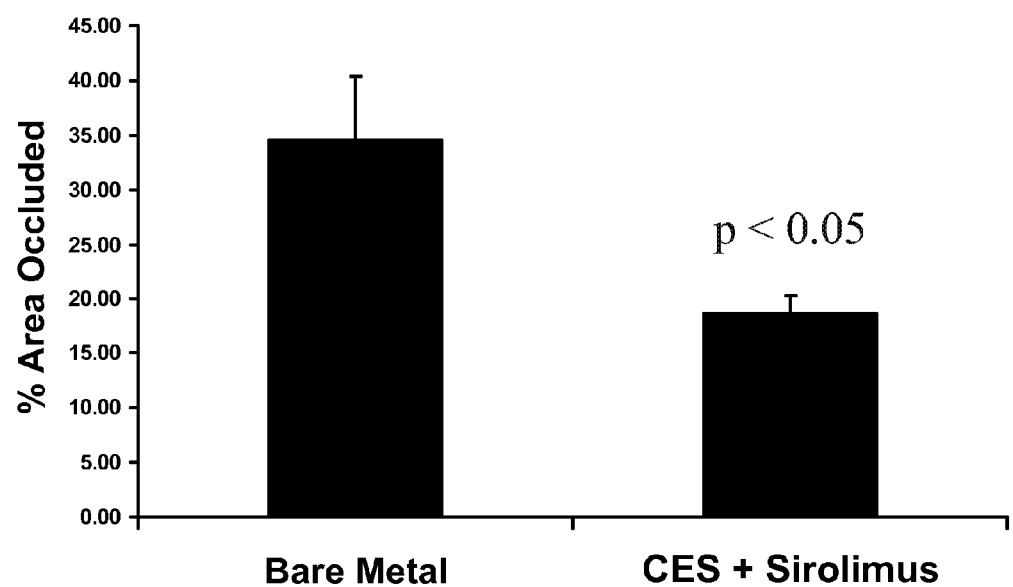
FIG. 27 is a graph showing 28-day area occlusion rates between a commercially available bare metal stent and a stent with a nanoporous surface loaded with sirolimus.
Figure 28:
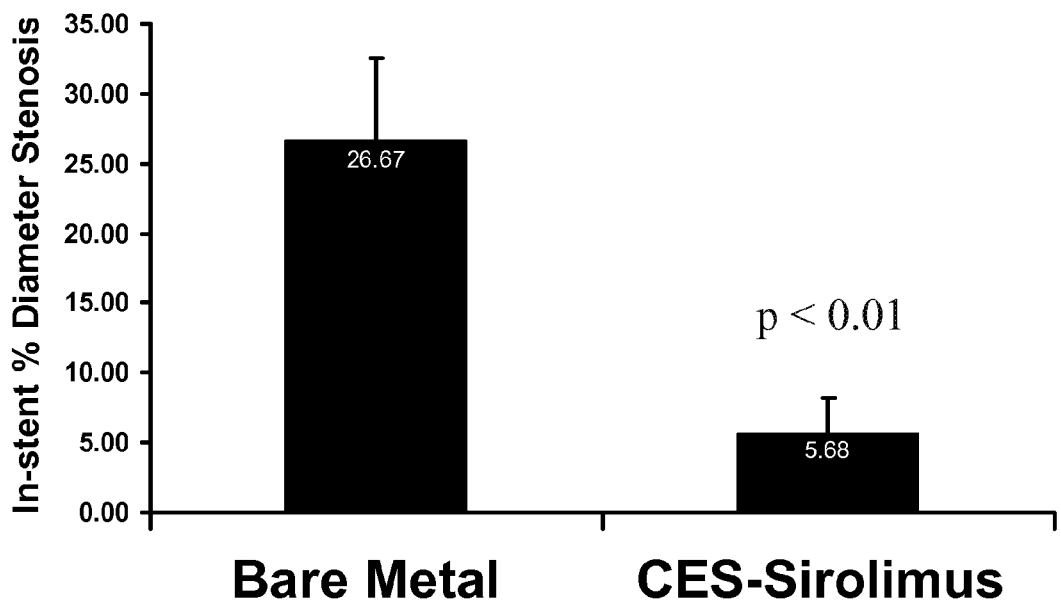
FIG. 28 is a graph showing 28-day in-stent restenosis rates between a commercially available bare metal stent and a stent with a nanoporous surface loaded with sirolimus.

Results of preclinical studies of Guidant Vision stent with a CES layer applied to its surface and loaded with Sirolimus (no topcoat) in a 28-day pig coronary artery injury model showed >70% inhibition of intima formation as compared to bare metal Vision controls. FIG. 26 are representative images illustrating reduced neointima formation in a CES-coated Vision stent loaded with sirolimus compared to a bare Vision stents in pigs at 28 days. CES-coated Vision stents also showed reduced vascular inflammation and improved adhesion of cells-tissues to the stent surface as compared to bare metal control Vision stents based on histological analyses. While the improved histocompatibility properties of a CES-coating may used with bare metal stents, they may also be combined with therapeutic agents loaded into the CES-coating or bonded thereto. In one example, a biodegradable coating comprising an anti-restenosis agent may be bonded to the CES-coating to provide early therapy against stenosis but after the biodegradable coating has substantially degraded, the remaining CES-coating continues to provide a reduced risk of restenosis compared to traditional bare-metal stents. Referring to FIG. 27, a CES-coated, sirolimus-loaded stent demonstrated a statistically significant difference in the percent of intimal area occlusion as determined by histopathology in a 28-day pig model. As depicted in FIG. 28, a statistically significant difference in in-stent percentage diameter stenosis as determined by quantitative coronary angiography (QCA) was also achieved by a CES-coated, sirolimus-loaded in comparison to bare metal controls.

Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. A stent for insertion into a body, the stent comprising a metal stent having a dealloyed porous surface, wherein the stent with only the porous surface and devoid of a therapeutic agent exhibits reduced neointimal formation compared to a bare metal stent having the same configuration as the metal stent and lacking the porous surface.

2. The stent for insertion into a body as in claim 1, wherein the porous surface is a nanoporous surface with an average pore diameter of less than 200 nm.

3. The stent for insertion into a body as in claim 1, wherein the dealloyed surface is a nanoporous surface with an average pore diameter of less than 200 nm.

4. The stent for insertion into a body as in claim 1, wherein the stent is a coronary stent.

5. The stent for insertion into a body as in claim 1, wherein the stent further comprises a biodegradable coating bonded to the porous surface.

6. The stent for insertion into a body as in claim 1, wherein the stent exhibits a reduced percentage area of stenosis compared to the same bare metal stent lacking the porous surface.

7. The stent for insertion into a body as in claim 1, wherein the stent lacks an elutable therapeutic agent.

8. The stent for insertion into a body as in claim 3, wherein the nanoporous surface contains at least one therapeutic agent.

9. The stent for insertion into a body as in claim 8, wherein the at least one therapeutic agent is selected from a group consisting of: actinomycin-D, batimistat, c-myc antisense, dexamethasone, paclitaxel, taxanes, sirolimus, tacrolimus, everolimus, unfractionated heparin, low-molecular weight heparin, enoxaprin, bivalirudin, tyrosine kinase inhibitors, imatinib mesylate, wortmannin, PDGF inhibitors, AG1295 (6,7-Dimethyl-2-phenylquinoxaline), rho kinase inhibitors, Y27632 ((+)-(R)-trans-4-(1-aminoethyl)-N-(4-pyridyl)cyclohexanecarboxamide dihydrochloride), calcium channel blockers, sphingosine phosphate inhibitors, amlodipine, nifedipine, ACE inhibitors, synthetic polysaccharides, ticlopinin, dipyridamole, clopidogrel, fondaparinux, streptokinase, urokinase, r-urokinase, r-prourokinase, rt-PA, APSAC (anisoylated plasminogen streptokinase activator complex), TNK-rt-PA, reteplase, alteplase, monteplase, lanoplase, pamiteplase, staphylokinase, abciximab, tirofiban, orbofiban, xemilofiban, sibrafiban, roxifiban, ABT-578, CCI-779, biolimus-A9, temsirolimus, anti-CD34 antibodies, mycophenolic acid, Vitamin E, omega-3 fatty acids, tempamine, docetaxel, an agent for altering cytochrome P450 function, cyclosporine, an azole antifungal agent, itraconazole, ketoconazole, a macrolide antibiotic, clarithromycin, erythromycin, troleandomycin, an nonnucleoside reverse transcriptase inhibitor, delavirdine, a protease inhibitor, indinavir, ritonavir, saquinavir, ritonavir, grapefruit juice extract, mifepristone, nefazodone, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radio-contrast agent, a radio-isotope, a prodrug, antibody fragments, antibodies, live cells, therapeutic drug delivery microspheres, drug delivery microbeads, gene therapy agents, viral vectors and plasmid DNA vectors.

10. The stent for insertion into a body as in claim 2, wherein the average pore diameter is less than about 5 nm.

11. The stent for insertion into a body as in claim 3, wherein the average pore diameter is less than about 5 nm.

* * * * *